US 7,968,563 B2
Jun. 28, 2011

(12) United States Patent
Kshirsagar et al.

(10) Patent No.: US 7,968,563 B2
(45) Date of Patent: Jun. 28, 2011

(54) OXIME AND HYDROXYLAMINE SUBSTITUTED IMIDAZO[4,5-C] RING COMPOUNDS AND METHODS

(75) Inventors: Tushar A. Kshirsagar, Woodbury, MN (US); Gregory D. Lundquist, Jr., Eagan, MN (US); Joseph F. Dellaria, Woodbury, MN (US); Matthew R. Radmer, North Robbinsdale, MN (US); Bernhard M. Zimmermann, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 582 days.

(21) Appl. No.: 11/884,153

(22) PCT Filed: Feb. 10, 2006

(86) PCT No.: PCT/US2006/004737
§ 371 (c)(1),
(2), (4) Date: Sep. 23, 2008

(87) PCT Pub. No.: WO2006/086634
PCT Pub. Date: Aug. 17, 2006

(65) Prior Publication Data
US 2010/0069427 A9    Mar. 18, 2010

Related U.S. Application Data

(60) Provisional application No. 60/652,209, filed on Feb. 11, 2005.

(51) Int. Cl.
*A61K 31/437* (2006.01)
*C07D 471/04* (2006.01)
*A61P 35/00* (2006.01)

(52) U.S. Cl. .......................................... 514/293; 546/82
(58) Field of Classification Search .................. 514/293; 546/82
See application file for complete search history.

(56) References Cited

U.S. PATENT DOCUMENTS

| | | |
|---|---|---|
| 3,314,941 A | 4/1967 | Lundquist, Jr. et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster et al. |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |

(Continued)

FOREIGN PATENT DOCUMENTS

AU    2004220534 A1    9/2004

(Continued)

OTHER PUBLICATIONS

International Search Report and Written Opinion for PCT/US2006/004737 mailed Jun. 19, 2007.
International Preliminary Report on Patentability for PCT/US2006/004737 mailed Aug. 23, 2007.
[No Author Listed] "Aqueous cream." Wikipedia. Available at http://en.wikipedia.org/wiki/Aqueous_cream. Last accessed Sep. 15, 2010.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.

(Continued)

*Primary Examiner* — D. Margaret Seaman
*Assistant Examiner* — Niloofar Rahmani

(57) ABSTRACT

Imidazo[4,5-c] ring compounds, (e.g. imidazo[4,5-c]pyridines, imidazo[4,5-c]quinolines, 6,7,8,9-tetrahydro imidazo[4,5-c]quinolines, imidazo[4,5-c]naphthyridine, and 6,7,8,9-tetrahydro imidazo[4,5-c]naphthyridine compounds) having an oxime or hydroxylamine substituent at the 2-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

23 Claims, No Drawings

U.S. PATENT DOCUMENTS

| | | | |
|---|---|---|---|
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,556,785 A | 9/1996 | Kishida |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |

| | | |
|---|---|---|
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |

| | | | |
|---|---|---|---|
| 2009/0318435 A1 | 12/2009 | Hays et al. | |
| 2010/0113565 A1 | 5/2010 | Gorden et al. | |
| 2010/0240693 A1 | 9/2010 | Lundquist, Jr. et al. | |
| 2010/0317684 A1 | 12/2010 | Kshirsagar et al. | |

FOREIGN PATENT DOCUMENTS

| | | |
|---|---|---|
| AU | 2004229478 A1 | 10/2004 |
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 A1 | 10/1990 |
| EP | 0 425 306 A2 | 5/1991 |
| EP | 0 510 260 A2 | 10/1992 |
| EP | 0 556 008 A1 | 8/1993 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 A1 | 6/2001 |
| EP | 1 145 340 A2 | 10/2001 |
| EP | 1 256 582 A1 | 11/2002 |
| EP | 1 341 791 B1 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 1180156 A | 7/1989 |
| JP | 4066571 A | 3/1992 |
| JP | 4327587 A | 11/1992 |
| JP | 5286973 A | 11/1993 |
| JP | 9208584 A | 8/1997 |
| JP | 11222432 A | 8/1999 |
| JP | 2000247884 A | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO-02/36592 A1 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121-AI | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | 2004058759 * | 7/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO-2005/018551 A2 | 3/2005 |
| WO | WO-2005/018555 A2 | 3/2005 |
| WO | WO 2005/018556 A2 | 3/2005 |
| WO | WO-2005/020999 A1 | 3/2005 |
| WO | WO-2005/023190 A2 | 3/2005 |
| WO | WO-2005/025614 A3 | 3/2005 |
| WO | WO-2005/029037 A2 | 3/2005 |
| WO | WO-2005/032484 A3 | 4/2005 |
| WO | WO-2005/041891 A2 | 5/2005 |
| WO | WO-2005/048933 A2 | 6/2005 |
| WO | WO 2005/048945 A2 | 6/2005 |
| WO | WO-2005/049076 A1 | 6/2005 |
| WO | WO 2005/051317 A2 | 6/2005 |
| WO | WO 2005/051324 A3 | 6/2005 |
| WO | WO-2005/054237 A1 | 6/2005 |
| WO | WO-2005/054238 A1 | 6/2005 |
| WO | WO-2005/065678 A1 | 7/2005 |
| WO | WO-2005/066169 A2 | 7/2005 |
| WO | WO-2005/066170 A1 | 7/2005 |
| WO | WO-2005/066172 A1 | 7/2005 |
| WO | WO-2005/067500 A2 | 7/2005 |

| WO | WO-2005/076783 A2 | 8/2005 |
| WO | WO-2005/079195 A2 | 9/2005 |
| WO | WO-2005/094531 A2 | 10/2005 |
| WO | WO-2005/110013 A2 | 11/2005 |
| WO | WO-2005/123079 A2 | 12/2005 |
| WO | WO-2005/123080 A2 | 12/2005 |
| WO | WO-2006/004737 A2 | 1/2006 |
| WO | WO-2006/009826 A1 | 1/2006 |
| WO | WO-2006/009832 A1 | 1/2006 |
| WO | WO-2006/026760 A2 | 3/2006 |
| WO | WO-2006/028451 A1 | 3/2006 |
| WO | WO-2006/028545 A2 | 3/2006 |
| WO | WO-2006/028962 A2 | 3/2006 |
| WO | WO-2006/029115 A2 | 3/2006 |
| WO | WO-2006/031878 A2 | 3/2006 |
| WO | WO-2006/038923 A2 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/002646 A2 | 1/2008 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Bachman et al., Synthesis of substituted quinolylamines. Derivatives of 4-amino-7-chloroquinoline. J Org Chem. 1950;15(6):1278-84.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Baranov et al., Imidazo[4-5c]quinolines. In Chemical Abstracts. 1976;85:637. Abstract 94362z.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (−)-Methadone from D-(−)-Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Berenyi et al., Ring transformation of condensed dihyrdo-astriazines. J Heterocyclic Chem. 1981;18:1537-40.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.
Borkan et al., An outbreak of venomous spider bites in a citrus grove. Am J Trop Med Hyg. Mar. 1995;52(3):228-30.
Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Brennan et al., Automated bioassay of interferons in microtest plates. Biotechniques. Jun./Jul. 1983(1):78-82.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chollet et al., Development of a topically active imiquimod formulation. Pharm Dev Technol. Jan. 1999;4(1):35-43.

Chuang et al., Toll-like receptor 9 mediates CpG-DNA signaling. J Leukoc Biol. Mar. 2002,71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1): S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson at al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Cutting edge: activation of murine TLR8 by a combination of imidazoquinoline immune response modifiers and polyT oligodeoxynucleotides. J Immunol. Nov. 15, 2006;177(10):6584-7.

Gorden et al., Oligodeoxynucleotides differentially modulate activation of TLR7 and TLR8 by imidazoquinolines. J Immunol. Dec. 1, 2006;177(11):8164-70.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al, Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Izumi et al., 1H-Imidazo[4,5-c]quinoline derivatives as novel potent TNF-alpha suppressors: synthesis and structure-activity relationship of 1-, 2-and 4-substituted 1H-imidazo[4,5-c]quinolines or 1H-imidazo[4,5-c]pyridines. Bioorg Med Chem. Jun. 12, 2003;11(12):2541-50.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jain et al., Chemical and pharmacological investigations of some omega-substituted alkylamino-3-aminopyridines. J Med Chem. Jan. 1968;11(1):87-92.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some ò-nitrokenes. J Am Chem Soc. 1947;69:2271-2275.

Kornman, Host modulation as a-therapeutic strategy in the treatment of periodontal disease. Clin Infect Dis. Mar. 1999;28(3):520-6.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γδ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. 1997 American Association of Pharmaceutical Scientists Annual Meeting. Poster Presentation, Boston, MA, Nov. 2-6. Pharma Res. 1997;14(11):S475. Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of *Lactococcus lactis*. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (*Loxosceles reclusa*) on human neutrophils. Toxicon. 1977;15(5):423-7.

Makarenkova et al., Identification of delta- and mu-type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of N$^\alpha$-Benzyloxycarbonyl-$_L$-Ornithine and of N$^\alpha$-(9-Fluorenylmethoxy)Carbonyl-$_L$-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998;52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, *Loxosceles reclusa*. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A,Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. 1997 American Association of Pharmaceutical Scientists Annual Meeting. Poster Presentation, Boston, MA, Nov. 2-6. Pharma Res. 1997;14(11):S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Testerman et al., Cytokine induction by the immunomodulators imiquimod and S-27609. J Leukoc Biol. Sep. 1995;58(3):365-72.

Thesing et al., [Darstellung and Eigenschaften des $\Delta^1$-Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells—the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Trav Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

\* cited by examiner

OXIME AND HYDROXYLAMINE SUBSTITUTED IMIDAZO[4,5-C] RING COMPOUNDS AND METHODS

CROSS REFERENCE TO RELATED APPLICATIONS

This application is a national stage filing under 35 U.S.C. §371 of PCT International application PCT/US2006/004737 designating the United States of America, and filed Feb. 10, 2006. This application claims the benefit under 35 U.S.C. §119(e) of U.S. provisional application Ser. No. 60/652,209, filed Feb. 11, 2005.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds that are useful in inducing cytokine biosynthesis in animals. Such compounds are of the following Formula I:

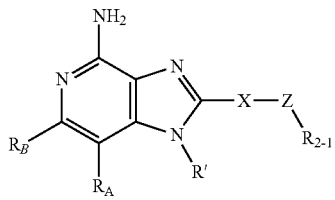

wherein $R_A$, $R_B$, X, Z, R', and $R_{2-1}$ are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic F disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I, I, III, IV, V, VI, and VII:

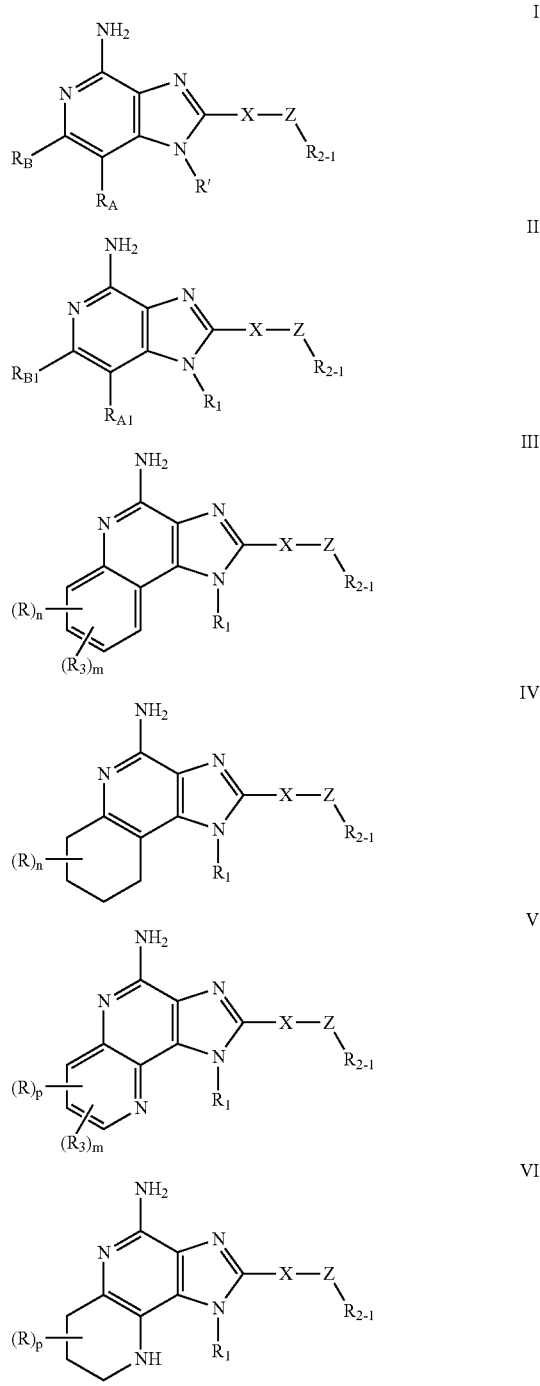

-continued

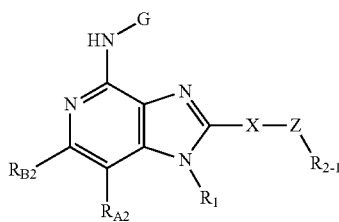

as well as certain intermediates of the following Formula VIII:

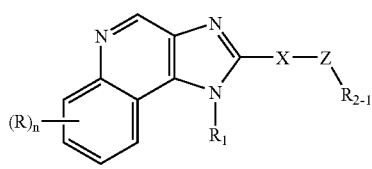

wherein $R_A$, $R_B$, $R_{A1}$, $R_{B1}$, $R_{A2}$, $R_{B2}$, R, R', $R_1$, $R_{2-1}$, $R_3$, m, n, p, G, X, and Z are as defined below; and pharmaceutically acceptable salts thereof.

In one embodiment, the present invention provides a compound of Formula I:

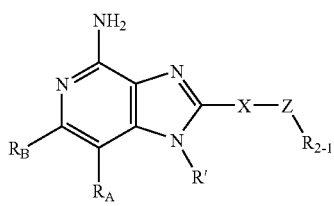

wherein:
Z is selected from the group consisting of:
—C(—N—O—$R_{2-2}$)— and
—C($R_{2-4}$)(—N(—OR$_{2-2}$)—Y—$R_{2-3}$)—;
X is selected from the group consisting of a bond, $C_{1-4}$ alkylene and $C_{2-4}$ alkenylene;
$R_2$—, $R_{2-2}$, and $R_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—$R_{2-5}$,
—NH—S(O)$_2$—$R_{2-5}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N($R_8$)$_2$,
—N($R_8$)—C(O)—$R_{2-5}$,
—NH—C(O)—NH—$R_{2-5}$,
—NH—C(O)—NH$_2$
—O—(CO)-alkyl, and
—C(O)-alkyl;
with the proviso that $R_{2-2}$ is other than alkenyl wherein the carbon atom bonded to —O— is doubly bonded to another carbon atom;
$R_{2-4}$ is selected from the group consisting of hydrogen, $C_{1-4}$alkyl, and phenyl;
$R_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;
Y is selected from the group consisting of:
a bond,
—C($R_6$)—,
—S(O)$_2$—,
—S(O)$_2$—N($R_8$)—,

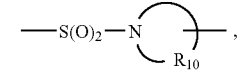

—C(O)—O—,
—C($R_6$)—N($R_8$)—,
—C(O)—N($R_9$)—S(O)$_2$—,
—C($R_6$)—N($R_8$)—C(O)—,

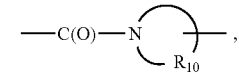

—C(O)—C(O)—,
—C(O)—C(O)—O—, and
—C(=NH)—N($R_8$)—;
$R_A$ and $R_B$ are each independently selected from the group consisting of:
hydrogen,
halogen,
alkyl,
alkenyl,
alkoxy,
alkylthio, and
—N($R_9$)$_2$;
or when taken together, $R_A$ and $R_B$ form a fused benzene ring or fused pyridine ring wherein the fused benzene ring or fused pyridine ring is unsubstituted or substituted by one or more R'" groups;

or when taken together, $R_A$ and $R_B$ form a fused cyclohexene ring or a fused tetrahydropyridine ring, wherein the fused cyclohexene or tetrahydropyridine ring is unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

R' is hydrogen or a non-interfering substituent;
R''' is a non-interfering substitutent;
$R_6$ is selected from the group consisting of =O and =S;
$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl; and
$R_{10}$ is $C_{3-8}$ alkylene; or a pharmaceutically acceptable salt thereof.

In another embodiment, the present invention provides a compound of Formula II:

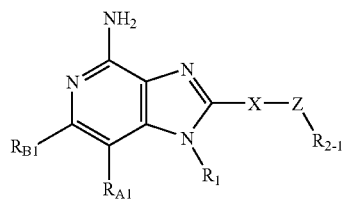

II wherein:
Z is selected from the group consisting of:
—C(=N—O—$R_{2-2}$)— and
—C($R_{2-4}$)(—N(—O$R_{2-2}$)—Y—$R_{2-3}$)—;
X is selected from the group consisting of a bond, $C_{1-4}$ alkylene and $C_{2-4}$ alkenylene;
$R_{2-1}$, $R_{2-2}$, and $R_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—$R_{2-5}$,
—NH—S(O)$_2$—$R_{2-5}$,
haloalkoxy,
halogen,
cyano,
nitro,
—$N_3$,
aryl,
heteroaryl,
heterocyclyl,
aryloxy,
arylalkyleneoxy,
—C(O)—O-alkyl,
—C(O)—N($R_8$)$_2$,
—N($R_8$)—C(O)—$R_{2-5}$,
—NH—C(O)—NH—$R_{2-5}$,
—NH—C(O)—NH$_2$
—O—(CO)-alkyl, and
—C(O)-alkyl;
with the proviso that $R_{2-2}$ is other than alkenyl wherein the carbon atom bonded to —O— is doubly bonded to another carbon atom;
$R_{2-4}$ is selected from the group consisting of hydrogen, $C_{1-4}$alkyl, and phenyl;
$R_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —$N_3$;
Y is selected from the group consisting of:
a bond,
—C($R_6$)—,
—S(O)$_2$—,
—S(O)$_2$—N($R_8$)—,

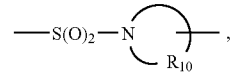

—C(O)—O—,
—C($R_6$)—N($R_8$)—,
—C(O)—N($R_8$)—S(O)$_2$—,
—C($R_6$)—N($R_8$)—C(O)—,

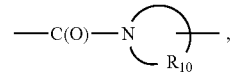

—C(O)—C(O)—,
—C(O)—C(O)—O—, and
—C(=NH)—N($R_8$)—;
$R_{A1}$ and $R_{B1}$ are each independently selected from the group consisting of:
hydrogen,
halogen,
alkyl,
alkenyl,
alkoxy,
alkylthio, and
—N($R_9$)$_2$;
$R_1$ is selected from the group consisting of:
—$R_4$,
—X'—$R_4$,
—X'—Y'—$R_4$, —X'—Y'—X'—Y'—R₄, and
—X'—R₅;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—O—,
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,
—O—N(R₈)-Q-,
—O—N=C(R₄)—,
—C(=N—O—R₈)—,
—CH(—N(—O—R₈)-Q-R₄)—,

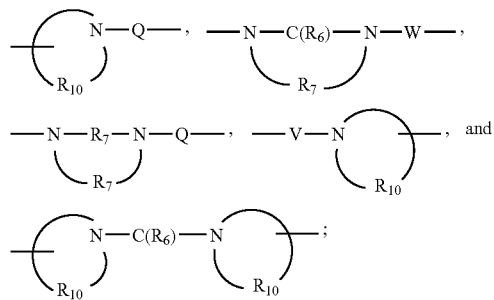

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

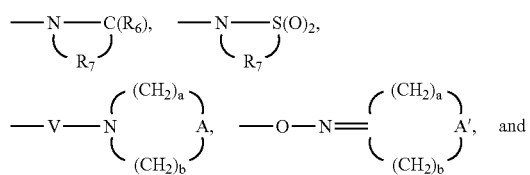

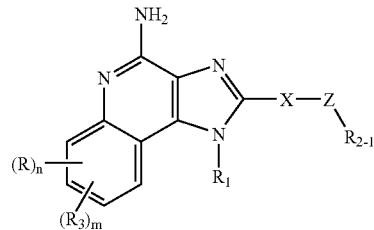

R₆ is selected from the group consisting of =O and =S;
R₇ is C₂₋₇ alkylene;
R₈ is selected from the group consisting of hydrogen, C₁₋₁₀ alkyl, C₂₋₁₀ alkenyl, C₁₋₁₀ alkoxy-C₁₋₁₀ alkylenyl, hydroxy-C₁₋₁₀ alkylenyl, heteroaryl-C₁₋₁₀ alkylenyl, and aryl-C₁₋₁₀ alkylenyl;
R₉ is selected from the group consisting of hydrogen and alkyl;
R₁₀ is C₃₋₈ alkylene;
A is selected from the group consisting of —O—, —C(O)—, —S(O)₀₋₂—, —CH₂—, and —N(-Q-R₄)—;
A' is selected from the group consisting of —O—, —S(O)₀₋₂—, —N(-Q-R₄)—, and —CH₂—;
Q is selected from the group consisting of a bond, —C(R₆)—, —C(R₆)—C(R₆)—, —S(O)₂—, —C(R₆)—N(R₈)—W—, —S(O)—NR₈)—, —C(R₆)—O—, —C(R₆)—S—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—; and
a and b are independently integers from 1 to 6 with the proviso that a+b is ≦7; or a pharmaceutically acceptable salt thereof.

In another embodiment, the present invention provides a compound of Formula III:

III

[structure of Formula III with NH₂ group, fused ring system, substituents (R)ₙ, (R₃)ₘ, R₁, and X—Z—R₂₋₁]

wherein:
Z is selected from the group consisting of:
—C(=N—O—R₂₋₂)— and
—C(R₂₋₄)(—N(—OR₂₋₂)—Y—R₂₋₃)—;
X is selected from the group consisting of a bond, C₁₋₄ alkylene and C₂₋₄ alkenylene;
R₂₋₁, R₂₋₂, and R₂₋₃ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:

hydroxy,
alkyl,
haloalkyl,
hydroxyalkyl,
alkoxy,
dialkylamino,
—S(O)$_{0-2}$—R$_{2-5}$,
—NH—S(O)$_2$—R$_{2-5}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)—R$_{2-5}$,
—NH—C(O)—NH—R$_{2-5}$,
—NH—C(O)—NH$_2$
—O—(CO)-alkyl, and
—C(O)-alkyl;
with the proviso that R$_{2-2}$ is other than alkenyl wherein the carbon atom bonded to —O— is doubly bonded to another carbon atom;
R$_{2-4}$ is selected from the group consisting of hydrogen, C$_{1-4}$alkyl, and phenyl;
R$_{2-5}$ is selected from the group consisting of alkyl, aryl, arylalkylenyl, heteroaryl, and heteroarylalkylenyl, each of which is substituted or substituted by one or more substituents selected from the group consisting of halogen, cyano, nitro, alkoxy, dialkylamino, alkylthio, haloalkyl, haloalkoxy, alkyl, and —N$_3$;
Y is selected from the group consisting of:
a bond,
—C(R$_6$)—,
—S(O)$_2$—,
—S(O)$_2$—N(R$_8$)—,

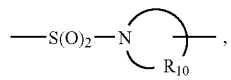

—C(O)—O—,
—C(R$_6$)—N(R$_8$)—,
—C(O)—N(R$_8$)—S(O)$_2$—,
—C(R$_6$)—N(R$_8$)—C(O)—,

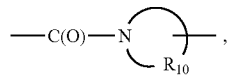

—C(O)—C(O)—,
—C(O)—C(O)—O—, and
—C(=NH)—N(R$_8$)—;
R is selected from the group consisting of:
halogen,
hydroxy,
alkyl,
alkenyl,
haloalkyl,
alkoxy,
alkylthio, and
—N(R$_9$)$_2$;
n is an integer from 0 to 4;
R$_1$ is selected from the group consisting of:
—R$_4$,
—X'—R$_4$,
—X'—Y'—R$_4$,
—X'—Y'—X'—Y'—R$_4$, and
—X'—R$_5$;
R$_3$ is selected from the group consisting of:
—Z'—R$_4$,
—Z'—X'—R$_4$,
—Z'—X'—Y'—R$_4$,
—Z'—X'—Y'—X'—Y'—R$_4$, and
—Z'—X'—R$_5$;
m is 0 or 1, with the proviso that when m is 1 then n is 0 or 1;
X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;
Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

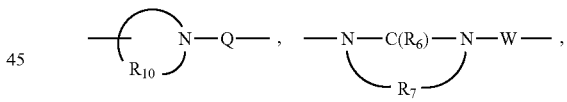

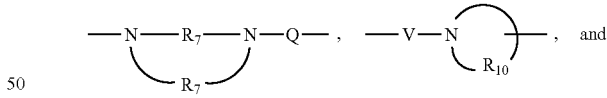

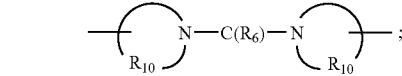

Z' is a bond or —O—;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

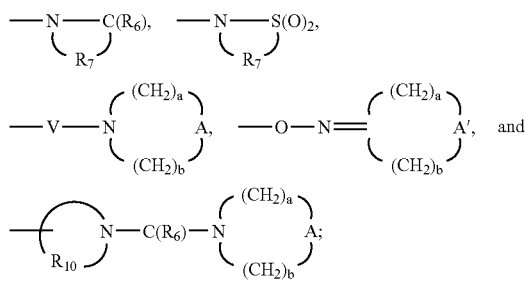

$R_6$ is selected from the group consisting of =O and =S;
$R_7$ is $C_{2-7}$ allylene;
$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

In another embodiment, the present invention provides a compound of Formula IV:

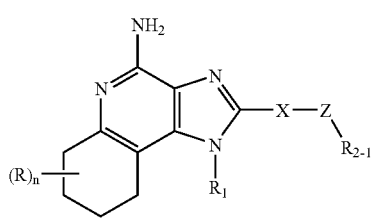

wherein:
Z is selected from the group consisting of:
—C(=N—O—R$_{2-2}$)— and
—C(R$_{2-4}$)(—N(—OR$_{2-2}$)—Y—R$_{2-3}$)—;
X is selected from the group consisting of a bond, $C_{1-4}$ alkylene and $C_{2-4}$ alkenylene;
$R_{2-1}$, $R_{2-2}$, and $R_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—R$_{2-5}$,
—NH—S(O)$_2$—R$_{2-5}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)—R$_{2-5}$,
—NH—C(O)—NH—R$_{2-5}$,
NH—C(O)—NH$_2$
—O—(CO)-alkyl, and
—C(O)-alkyl;
with the proviso that $R_{2-2}$ is other than alkenyl wherein the carbon atom bonded to —O— is doubly bonded to another carbon atom;
$R_{2-4}$ is selected from the group consisting of hydrogen, $C_{1-4}$alkyl, and phenyl;
$R_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;
Y is selected from the group consisting of:
a bond,
—C(R$_6$)—,
—S(O)$_2$—,
—S(O)$_2$—N(R$_8$)—,

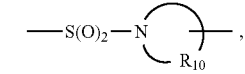

—C(O)—O—,
—C(R$_6$)—N(R$_8$)—,
—C(O)—N(R$_8$)—S(O)$_2$—,
—C(R$_6$)—N(R$_8$)—C(O)—,

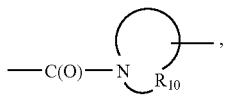

—C(O)—C(O)—,
—C(O)—C(O)—O—, and
—C(=NH)—N($R_8$)—;

R is selected from the group consisting of:
halogen,
hydroxy,
alkyl,
alkenyl,
haloalkyl,
alkoxy,
alkylthio, and
—N($R_9$)$_2$;

n is an integer from 0 to 4;

$R_1$ is selected from the group consisting of:
—$R_4$,
—X'—$R_4$,
—X'Y'—$R_4$,
—X'Y'—X'—Y'—$R_4$, and
—X'—$R_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

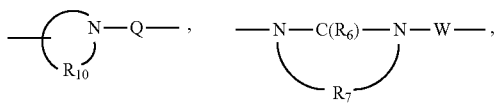

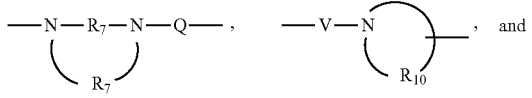

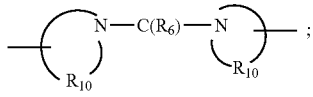

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

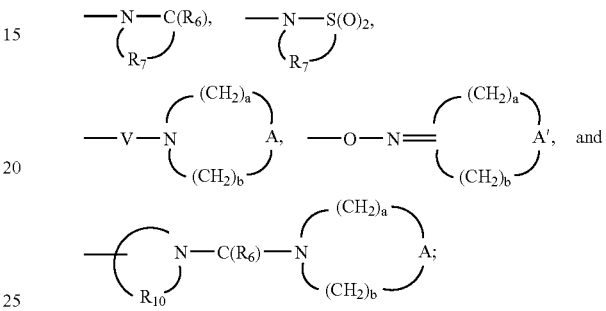

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(-Q-$R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

In another embodiment, the present invention provides a compound of Formula V:

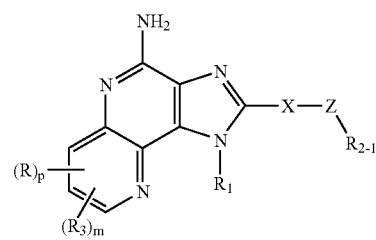

V wherein:

Z is selected from the group consisting of:
—C(=N—O—R$_{2-2}$)— and
—C(R$_{2-4}$)(—N(—OR$_{2-2}$)—Y—R$_{2-3}$)—;

X is selected from the group consisting of a bond, C$_{1-4}$ alkylene and C$_{2-4}$ alkenylene;

R$_{2-1}$, R$_{2-2}$, and R$_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—R$_{2-5}$,
—NH—S(O)$_2$—R$_{25}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)—R$_{2-5}$,
—NH—C(O)—NH—R$_{2-5}$,
—NH—C(O)—NH$_2$
O—(CO)-alkyl, and
—C(O)-alkyl;
with the proviso that R$_{2-2}$ is other than alkenyl wherein the carbon atom bonded to —O— is doubly bonded to another carbon atom;

R$_{2-4}$ is selected from the group consisting of hydrogen, C$_{1-4}$alkyl, and phenyl;

R$_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;

Y is selected from the group consisting of:
a bond,
—S(O)$_2$—,
—S(O)$_2$—N(R$_8$)—,

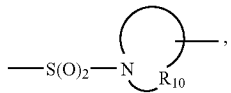

—C(O)—O—,
—C(R$_6$)—N(R$_8$)—,
—C(O)—N(R$_8$)—S(O)$_2$—,
—C(R$_6$)—N(R$_8$)—C(O)—,

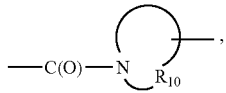

—C(O)—C(O)—,
—C(O)—C(O)—O—, and
—C(=NH)—N(R$_8$)—,

R is selected from the group consisting of:
halogen,
hydroxy,
alkyl,
alkenyl,
haloalkyl,
alkoxy,
alkylthio, and
—N(R$_9$)$_2$;

p is an integer from 0 to 3;

R$_1$ is selected from the group consisting of:
—R$_4$,
—X'—R$_4$,
—X'—Y'—R$_4$,
—X'—Y'—X'—Y'—R$_4$, and
—X'—R$_5$;

R$_3$ is selected from the group consisting of:
—Z'—R$_4$,
—Z'—X'—R$_4$,
—Z'—X'—Y'—X'—Y'—R$_4$, and
—Z'—X'—R$_5$;

m is 0 or 1, with the proviso that when m is 1 then p is 0 or 1;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

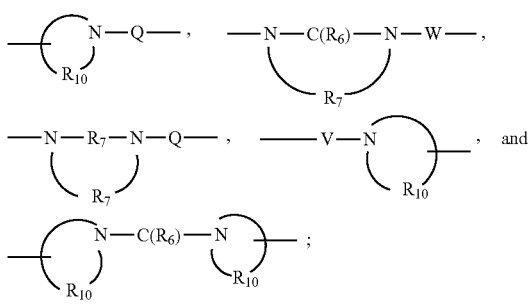

Z' is a bond or —O—;

$R_4$ is selected from the group consisting of hydrogen, alkyl, alkenyl, alkynyl, aryl, arylalkylenyl, aryloxyalkylenyl, alkylaryl-enyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

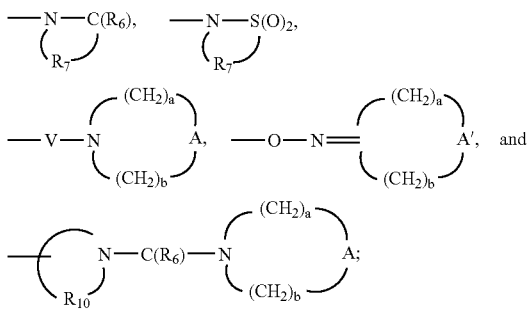

$R_6$ is selected from the group consisting of =O and =S;
$R_7$ is $C_{2-7}$ alkylene;
$R_8$ is selected from the group consisting of hydrogen, $C_{1-10}$ allyl, $C_{2-10}$ alkenyl, $Cl_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and a and b are independently integers from 1 to 6 with the proviso that a+b is ≦7; or a pharmaceutically acceptable salt thereof.

In another embodiment, the present invention provides a compound of Formula VI:

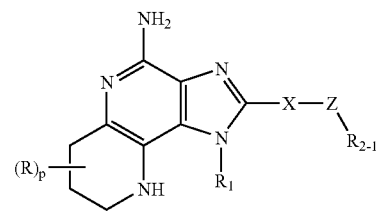

VI wherein:
Z is selected from the group consisting of:
—C(=N—O—R$_{2-2}$)— and
C(R$_{2-4}$)(—N(—OR$_{2-2}$)—Y—R$_{2-3}$)—;
X is selected from the group consisting of a bond, $C_{1-4}$ allylene and $C_{2-4}$ alkenylene;
$R_{2-1}$, $R_{2-2}$, and $R_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$—R$_{2-5}$,
—NH—S(O)$_2$—R$_{2-5}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)—R$_{2-5}$,
—NH—C(O)—NH—R$_{2-5}$,
—NH—C(O)—NH$_2$
—O—(CO)-alkyl, and
—C(O)-alkyl;
with the proviso that R$_{2-2}$ is other than alkenyl wherein the carbon atom bonded to —O— is doubly bonded to another carbon atom;

R$_{2-4}$ is selected from the group consisting of hydrogen, C$_{1-4}$alkyl, and phenyl;

R$_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;

Y is selected from the group consisting of:
a bond,
—C(R)—,
—S(O)$_2$—,
—S(O)$_2$—N(R$_8$)—,

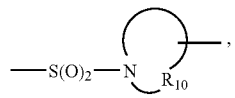

—C(O)—O—,
—C(R$_6$)—N(R$_8$)—,
—C(O)—N(R$_8$)—S(O)$_2$—,
—C(R$_6$)—N(R$_8$)—C(O)—,

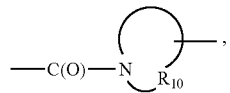

—C(O)—C(O)—,
—C(O)—C(O)—O—, and
C(=NH)—N(R$_8$)—;

R is selected from the group consisting of:
halogen,
hydroxy,
alkyl,
alkenyl,
haloalkyl,
alkoxy,
alkylthio, and
—N(R$_9$)$_2$;

p is an integer from 0 to 3;

R$_1$ is selected from the group consisting of:
—R$_4$,
—X'—R$_4$,
—X'—Y'—R$_4$,
—X'—Y'—X'—Y'—R$_4$, and
—X'—R$_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—, —O—C(R$_6$)—N(R$_8$)—,
C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

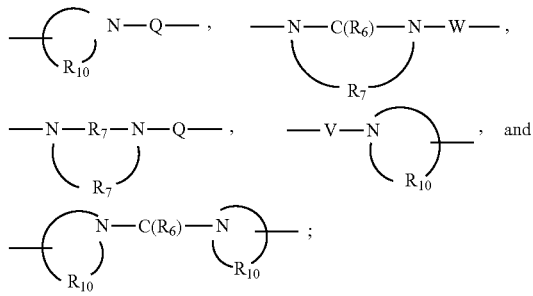

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

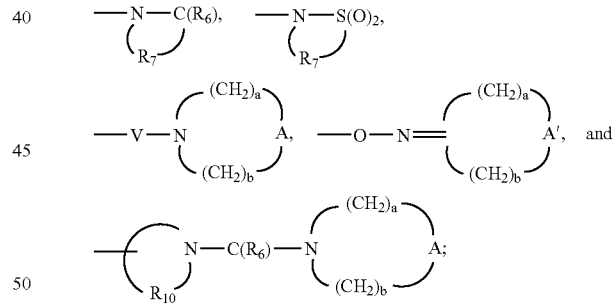

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, hydroxy-C$_{1-10}$ alkylenyl, heteroaryl-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N $(R_8)-W-$, $-S(O)_2-N(R_8)-$, $-C(R_6)-O-$, $-C(R_6)-S-$, and $-C(R_6)-N(OR_9)-$;

V is selected from the group consisting of $-C(R_6)-$, $-O-C(R_6)-$, $-N(R_8)-C(R_6)-$, and $-S(O)_2-$;

W is selected from the group consisting of a bond, $-C(O)-$, and $-S(O)_2-$; and a and b are independently integers from 1 to 6 with the proviso that a+b is $\leq 7$; or a pharmaceutically acceptable salt thereof.

In another embodiment, the present invention provides a compound of Formula VII, which is a prodrug:

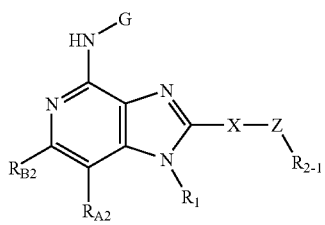

VII wherein:
G is selected from the group consisting of:
C(O)—R'',
α-aminoacyl,
α-aminoacyl-α-aminoacyl,
—C(O)—O—R'',
—C(O)—N(R'''')R''',
—C(=NY$_1$)—R'',
—CH(OH)—C(O)—OY$_1$,
—CH(OC$_{1-4}$ alkyl)Y$_0$,
—CH$_2$Y$_2$, and
—CH(CH$_3$)Y$_2$;

R'' and R'''' are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-CIA alkylenyl, halo-$C_{1-4}$ alkoxy, $-O-C(O)-CH_3$, $-C(O)-O-CH_3$, $-C(O)-NH_2$, $-O-CH_2-C(O)-NH_2$, $-NH_2$, and $-S(O-NH_2$, with the proviso that R'''' can also be hydrogen;

α-aminoacyl is an α-aminoacyl group derived from an α-amino acid selected from the group consisting of racemic, D-, and L-amino acids;

Y$_1$ is selected from the group consisting of hydrogen, $C_{1-6}$ alkyl, and benzyl;

Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N-$C_{1-6}$ alkylamino-$C_{1-4}$ alkylenyl;

Y$_2$ is selected from the group consisting of mono-N—$C_{1-6}$ alkylamino, di-N,N-$C_{1-6}$ alkylamino, morpholin-4-yl, piperidin-1-yl, pyrrolidin-1-yl, and 4-C 4 alkylpiperazin-1-yl;

$R_{A2}$ and $R_{B2}$ are each independently selected from the group consisting of:
hydrogen,
halogen,
alkyl,
alkenyl,
alkoxy,
alkylthio, and
$-N(R_9)_2$;

or when taken together, $R_{A2}$ and $R_{B2}$ form a fused benzene ring or fused pyridine ring wherein the fused benzene ring or fused pyridine ring is unsubstituted or substituted by one $R_3$ group, or one $R_3$ group and one R group, or one, two, three, or four R groups when on the fused benzene ring, or one, two, or three R groups when on the fused pyridine ring;

or when taken together, $R_{A2}$ and $R_{B2}$ form a fused cyclohexene ring or a fused tetrahydropyridine ring, wherein the fused cyclohexene or tetrahydropyridine ring is unsubstituted or substituted by one or more R groups; and X, Z, $R_{2-1}$, $R_1$, R, and $R_3$ are defined as in Formula III above; or a pharmaceutically acceptable salt thereof.

In one embodiment, the present invention provides an intermediate compound of Formula VIII:

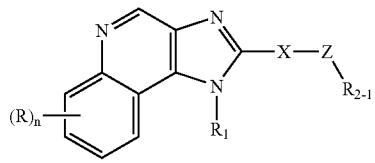

VIII wherein X, Z, $R_{2-1}$, $R_1$, R, and n are defined as in Formula III above; or a pharmaceutically acceptable salt thereof.

In one embodiment of Formula VIII, $R_1$ is preferably tetrahydro-2H-pyran-4-ylmethyl as shown in Formula VIIIa:

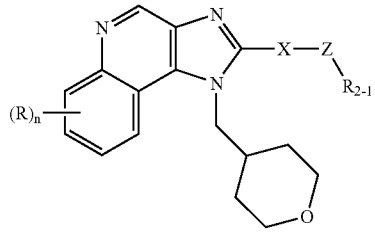

VIIIa which compound or pharmaceutically acceptable salt thereof has been found to induce cytokine biosynthesis as described herein for compounds or salts of Formulas I-VII.

Herein, "non-interfering" means that the ability of the compound or salt, which includes a non-interfering substituent, to modulate the biosynthesis of one or more cytokines is not destroyed by the non-interfering substituent. For certain embodiments, R''' is a non-interfering substituent. Illustrative non-interfering R' groups include those described above for $R_1$. Illustrative non-interfering R''' groups include those described above for R and $R_3$.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected. In another example, when an $R_1$ and an $R_3$ group both contain an $R_4$ group, each $R_4$ group is independently selected. In a further example, when more than one Y' group is present and each Y' group contains one or more $R_8$ groups, then each Y' group is independently selected, and each $R_8$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Z, X, Y, Y', $R_{A1}$, $R_{B1}$, R, $R_1$, $R_{2-1}$, $R_3$, Q, G, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, R''' is a non-interfering substituent.

For certain embodiments of Formula I, the one or more R''' groups are one $R_3$ group, or one $R_3$ group and one R group, or one, two, three, or four R groups when on the fused benzene ring, or one, two, or three R groups when on the fused pyridine ring; wherein $R_3$ is selected from the group consisting of —Z'—$R_4$, —Z'—X'—$R_4$, —Z'—X'—Y'—$R_4$, —Z'—X'—Y'—X'—Y'—$R_4$, and —Z'—X'—$R_5$.

For certain embodiments of Formula I or VII, $R_A$ and $R_B$ or $R_{A2}$ and $R_{B2}$, respectively, are each independently selected from the group consisting of hydrogen, halogen, alkyl, alkenyl, alkoxy, alkylthio, and —N($R_9$)$_2$. For certain embodiments, $R_A$ and $R_B$ or $R_{A2}$ and $R_{B2}$ are each independently selected from the group consisting of hydrogen and alkyl. For certain embodiments, $R_A$ and $R_B$ or $R_{A2}$ and $R_{B2}$ are both methyl.

For certain embodiments of Formula I, $R_A$ and $R_B$ are taken together to form a fused benzene ring wherein the benzene ring is unsubstituted or substituted by one or more R''' groups. In certain of these embodiments, the fused benzene ring is substituted by one or two R''' groups. In certain of these embodiments, the one or two R''' groups are one $R_3$ group, or one $R_3$ group and one R group. In certain of these embodiments, the fused benzene ring is unsubstituted.

For certain embodiments of Formula VII, $R_{A2}$ and $R_{B2}$ are taken together to form a fused benzene ring wherein the benzene ring is unsubstituted or substituted by one $R_3$ group, or one $R_3$ group and one R group. In certain of these embodiments, the fused benzene ring is unsubstituted.

For certain embodiments of Formula I, $R_A$ and $R_B$ are taken together to form a fused pyridine ring wherein the pyridine ring is unsubstituted or substituted by one or more R''' groups. In certain of these embodiments, the fused pyridine ring is substituted by one or two R''' groups. In certain of these embodiments, the one or two R''' groups are one $R_3$ group, or one $R_3$ group and one R group. In certain of these embodiments, the fused pyridine ring is

wherein the highlighted bond is the position where the ring is fused. In certain of these embodiments, the fused pyridine ring is unsubstituted.

For certain embodiments of Formula VII, $R_{A2}$ and $R_{B2}$ are taken together to form a fused pyridine ring wherein the pyridine ring is unsubstituted or substituted by one $R_3$ group, or one $R_3$ group and one R group. In certain of these embodiments, the fused pyridine ring is

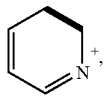

wherein the highlighted bond is the position where the ring is fused. In certain of these embodiments, the fused pyridine ring is unsubstituted.

For certain embodiments of Formula I or VII, $R_A$ and $R_B$ or $R_{A2}$ and $R_{B2}$, respectively, are taken together to form a fused cyclohexene ring wherein the fused cyclohexene ring is unsubstituted or substituted by one or more R groups. The double bond in the cyclohexene ring is the position where the ring is fused. In certain of these embodiments, the fused cyclohexene ring is unsubstituted.

For certain embodiments of Formula I or VII, $R_A$ and $R_B$ or $R_{A2}$ and $R_{B2}$, respectively, are taken together to form a fused tetrahydropyridine ring, wherein the fused tetrahydropyridine ring is unsubstituted or substituted by one or more R groups. The double bond in the tetrahydropyridine ring is the position where the ring is fused. In certain of these embodiments, the tetrahydropyridine ring is

wherein the highlighted bond indicates the position where the ring is fused. In certain of these embodiments, the fused tetrahydropyridine ring is unsubstituted.

For certain embodiments of Formula I, R' is hydrogen or a non-interfering substituent.

For certain embodiments of Formula I, R' is a non-interfering substituent.

For certain embodiments of Formula I, R' is $R_1$; wherein $R_1$ is selected from the group consisting of $—R_4$, $—X'—R_4$, $—X'—Y'—R_4$, $—X'—Y'—X'—Y'—R_4$, and $—X'—R_5$.

For certain embodiments of Formula II, $R_{A1}$ and $R_{B1}$ are each independently selected from the group consisting of hydrogen, halogen, alkyl, alkenyl, alkoxy, alkylthio, and $—N(R_9)_2$.

For certain embodiments of Formula II, $R_{A1}$ and $R_{B1}$ are each independently selected from the group consisting of hydrogen and alkyl. For certain of these embodiments, $R_{A1}$ and $R_{B1}$ are both methyl.

For certain embodiments of Formulas I, III VI, V, VI, VII, or VIII, R is halogen or hydroxy.

For certain embodiments of Formulas III, V, or VIII, R is bromine.

For certain embodiments of Formulas III, IV or VIII, n is 0.

For certain embodiments of Formula V or VI, p is 0.

For certain embodiments, including any one of the above embodiments wherein $R_3$ is present, $R_3$ is benzyloxy.

For certain embodiments, including any one of the above embodiments wherein $R_3$ is present, except where $R_3$ is benzyloxy, $R_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(N,N-dimethylaminocarbonyl)phenyl.

For certain embodiments, including any one of the above embodiments of Formulas III or V wherein this definition is not excluded, m is 0.

For certain embodiments, including any one of the above embodiments, Z is selected from the group consisting of $—C(=N—O—R_{2-2})—$ and $—C(R_{2-4})(—N(—OR_{2-2})—Y—R_{2-3})—$.

For certain embodiments, including any one of the above embodiments, Z is $—C(=N—O—R_{2-2})—$.

For certain embodiments, including any one of the above embodiments except where Z is $—C(=N—O—R_{2-2})—$, Z is $—C(R_{2-4})(—N(—OR_{2-2})—Y—R_{2-3})—$. For certain of these embodiments, $R_{2-4}$ is hydrogen. For certain of these embodiments, Y is a bond. For certain of these embodiments, $R_{2-3}$ is selected from the group consisting of hydrogen and alkyl. Alternatively, Y is selected from the group consisting of $—C(O)—$, $—S(O)_2—$, and $—C(O)—NH—$. For certain of these embodiments, $R_{2-3}$ is alkyl.

For certain embodiments, including any one of the above embodiments, $R_{2-2}$ is selected from the group consisting of hydrogen, alkyl, arylalkylenyl, and heteroarylalkylenyl. For certain of these embodiments, $R_{2-2}$ is hydrogen, $C_{1-4}$ alkyl, benzyl, or pyridin-2-ylmethyl.

For certain embodiments, including any one of the above embodiments, $R_{2-1}$ is selected from the group consisting of hydrogen, alkyl, and aryl. For certain of these embodiments, $R_{2-1}$ is hydrogen, $C_{1-4}$ alkyl, or phenyl.

For certain embodiments, including any one of the above embodiments, X is a bond or $C_{1-4}$ alkylene. For certain of these embodiments, X is a bond, methylene, or ethylene.

For certain embodiments, including any one of the above embodiments wherein $R_1$ is present, $R_1$ is selected from the group consisting of $—R_4$, $—X'—R_4$, $—X'—Y'—R_4$, $—X'—Y'—X'—Y'—R_4$, and $—X'—R_5$.

For certain embodiments, including any one of the above embodiments wherein $R_1$ is present, $R_1$ is selected from the group consisting of alkyl, arylalkylenyl, aryloxyalkylenyl, hydroxyalkyl, dihydroxyalkyl, alkylsulfonylalkylenyl, $—X'—Y'—R_4$, and $—X'—R_5$, and heterocyclylalkylenyl; wherein the heterocyclyl of the heterocyclylalkylenyl group is optionally substituted by one or more alkyl groups; wherein X' is alkylene; Y' is —N(R$_8$)—C(O)—, —N(R$_8$)—S(O)$_2$—, —N(R$_8$)—C(O)—N(R$_8$)—, or

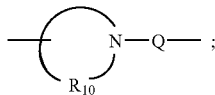

R$_4$ is alkyl, aryl, or heteroaryl; and R$_5$ is

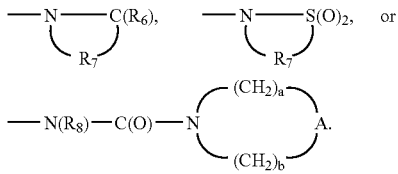

For certain embodiments, including any one of the above embodiments, R$_1$ is selected from the group consisting of 2-hydroxy-2-methylpropyl, 2-methylpropyl, propyl, ethyl, methyl, 2,3-dihydroxypropyl, 2-phenoxyethyl, 4-[(methylsulfonyl)amino]butyl, 2-methyl-2-[(methylsulfonyl)amino]propyl, 2-(acetylamino)-2-methylpropyl, 2-{[(isopropylamino)carbonyl]amino}-2-methylpropyl, 4-{[(isopropylamino)carbonyl]amino}butyl, 4-(1,1-dioxidoisothiazolidin-2-yl)butyl, tetrahydro-2H-pyran-4-ylmethyl, and (2,2-dimethyl-1,3-dioxolan-4-yl)methyl. For certain of these embodiments, R$_1$ is tetrahydro-2H-pyran-4-ylmethyl.

For certain embodiments, including any one of the above embodiments, except where this definition is excluded, R$_1$ is selected from the group consisting of (1-hydroxycyclobutyl)methyl, (1-hydroxycyclopentyl)methyl, and (1-hydroxycyclohexyl)methyl. For certain of these embodiments, R$_1$ is (1-hydroxycyclobutyl)methyl.

For certain embodiments, R is selected from the group consisting of halogen, hydroxy, alkyl, alkenyl, haloalkyl, alkoxy, alkylthio, and —N(R$_9$)$_2$.

For certain embodiments, R is selected from the group consisting of alkyl, alkoxy, hydroxy, halogen, and trifluoromethyl.

For certain embodiments, R is halogen or hydroxy.

For certain embodiments, R is bromine.

For certain embodiments, R$_{2-1}$, R$_{2-2}$, and R$_{2-3}$ are independently selected from the group consisting of hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$—R$_{2-5}$, —NH—S(O)$_2$—R$_{2-5}$, haloalkoxy, halogen, cyano, nitro, —N$_3$, aryl, heteroaryl, heterocyclyl, aryloxy, arylalkyleneoxy, —C(O)—O-alkyl, —C(O)—N(R$_8$)$_2$, —N(R)—C(O)—R$_{2-5}$, —NH—C(O)—NH—R$_{2-5}$, —NH—C(O)—NH$_2$, —O—(CO)-alkyl, and —C(O)-alkyl; with the proviso that R$_{2-2}$ is other than alkenyl wherein the carbon atom bonded to —O— is doubly bonded to another carbon atom;

For certain embodiments, R$_{2-1}$ is selected from the group consisting of hydrogen, alkyl, and aryl.

For certain embodiments, R$_{2-1}$ is hydrogen, C$_{1-4}$ alkyl, or phenyl.

For certain embodiments, R$_{2-1}$ is hydrogen.

For certain embodiments, R$_{2-2}$ is selected from the group consisting of hydrogen, alkyl, arylalkylenyl, and heteroarylalkylenyl.

For certain embodiments, R$_{2-2}$ is hydrogen, C$_{1-4}$ alkyl, benzyl, or pyridin-2-ylmethyl.

For certain embodiments, R$_{2-2}$ is C$_{1-10}$ alkyl.

For certain embodiments, R$_{2-2}$ is methyl.

For certain embodiments, R$_{2-2}$ is hydrogen.

For certain embodiments, R$_{2-3}$ is selected from the group consisting of hydrogen and alkyl.

For certain embodiments, R$_{2-3}$ is alkyl.

For certain embodiments, R$_{2-3}$ is hydrogen or methyl.

For certain embodiments, R$_{2-4}$ is selected from the group consisting of hydrogen, C$_{1-4}$alkyl, and phenyl.

For certain embodiments, R$_{2-4}$ is hydrogen.

For certain embodiments, R$_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$.

For certain embodiments, R$_{2-5}$ is hydrogen or alkyl.

For certain embodiments, R$_{2-5}$ is hydrogen or C$_{1-4}$ alkyl.

For certain embodiments, R$_3$ is selected from the group consisting of —Z'—R$_4$, —Z'—X'—R$_4$, —Z'—X'—Y'—R$_4$, —Z'—X'—Y'—X'—Y'—R$_4$, and —Z'—X'—R$_5$.

For certain embodiments, R$_3$ is selected from the group consisting of —Z'—R$_4$, —Z'—X'—Y'—R$_4$, and —Z'—X'—R$_5$.

For certain embodiments, R$_3$ is —Z'—R$_4$.

For certain embodiments, R$_3$ is —Z'—X'—Y'—R$_4$.

For certain embodiments, R$_3$ is —Z'—X'—R$_5$.

For certain embodiments, R$_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(NAN-dimethylaminocarbonyl)phenyl.

For certain embodiments, including any of the above embodiments where R$_3$ is present, —R$_3$ is at the 7-position.

For certain embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, R$_4$ is alkyl, aryl, or heteroaryl.

For certain embodiments, R$_4$ is hydrogen or alkyl.

For certain embodiments, R$_4$ is C$_{1-4}$ alkyl.

For certain embodiments, R$_5$ is selected from the group consisting of:

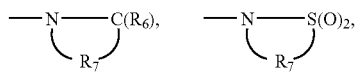

-continued

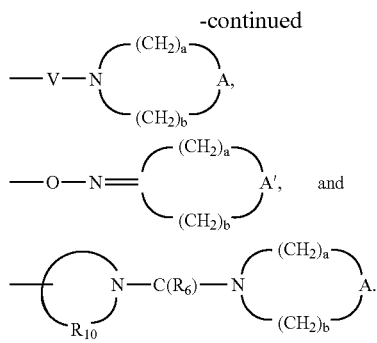

For certain embodiments, $R_5$ is selected from the group consisting of:

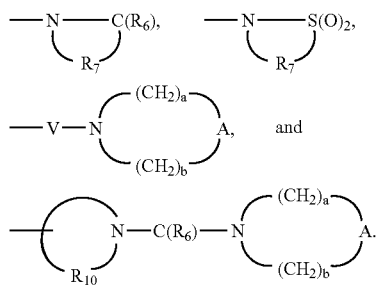

For certain embodiments, $R_5$ is

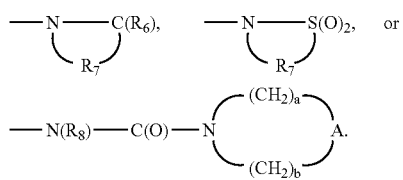

For certain embodiments, $R_5$ is

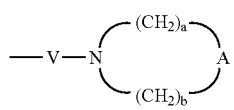

wherein V is —C(O)—, and A is —O—.

For certain embodiments, $R_6$ is selected from the group consisting of =O and —S.

For certain embodiments, $R_6$ is =O.

For certain embodiments, $R_7$ is $C_{2-7}$ alkylene.

For certain embodiments, $R_7$ is $C_{2-4}$ alkylene.

For certain embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, hydroxy-$C_{1-10}$ alkylenyl, heteroaryl-$C_{1-10}$ alkylenyl, and aryl-$C_{1-10}$ alkylenyl.

For certain embodiments, $R_8$ is selected from the group consisting of hydrogen, $C_{1-4}$ alkyl, and $C_{1-4}$ alkoxy-$C_{1-4}$ alkylenyl.

For certain embodiments, $R_8$ is hydrogen or $C_{1-4}$ alkyl.

For certain embodiments, $R_8$ is hydrogen.

For certain embodiments, $R_9$ is selected from the group consisting of hydrogen and alkyl.

For certain embodiments, $R_{10}$ is $C_{3-48}$ alkylene.

For certain embodiments, $R_{10}$ is $C_{4-4}$ alkylene.

For certain embodiments, A is selected from the group consisting of —O—, —C(O)—, —S(O)$_{0-2}$—, —CH$_2$—, and —N(-Q-R$_4$)—.

For certain embodiments, A is —O—, —CH$_2$—, or —S(O)$_2$—.

For certain embodiments, A is —O— or —S(O)$_2$—.

For certain embodiments, A is —O—.

For certain embodiments, A' is selected from the group consisting of —O—, —S(O)$_{0-2}$—, —N(-Q-R$_4$)—, and —CH$_2$—.

In certain embodiments, A' is selected from the group consisting of —CH$_2$—, —S(O)$_2$—, and —O—.

In certain embodiments, A' is —N(-Q-R$_4$)—.

In certain embodiments, A' is —CH$_2$—.

In certain embodiments, A' is —O—.

For certain embodiments, including any one of the above embodiments of Formula VII, G is selected from the group consisting of —C(O)—R″, α-aminoacyl, α-aminoacyl-α-aminoacyl, —C(O)—O—R″, —C(O)—N(R‴)R″, —C(=NY$_1$)—R″, —CH(OH)—C(O)—OY$_1$, —CH(OC$_{1-4}$ alkyl)Y$_0$, —CH$_2$Y$_2$, and —CH(CH$_3$)Y$_2$. For certain of these embodiments, R″ and R‴ are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R‴ can also be hydrogen; α-aminoacyl is an α-aminoacyl group derived from an α-amino acid selected from the group consisting of racemic, D-, and L-amino acids; $Y_1$ is selected from the group consisting of hydrogen, $C_{1-6}$ alkyl, and benzyl; $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-CIA alkylenyl, and di-N,N-$C_{1-6}$ alkylamino-$C_{1-4}$ alkylenyl; and $Y_2$ is selected from the group consisting of mono-N—$C_{1-6}$ alkylamino, di-N,N-$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula VII, G is selected from the group consisting of —C(O)—R″, α-aminoacyl, and —C(O)—O—R″.

For certain embodiments, including any one of the above embodiments of Formula VII, G is selected from the group consisting of —C(O)—R″, α-amino-$C_{2-11}$ acyl, and —C(O)—O—R″. α-Amino-$C_{2-11}$ acyl includes α-amino acids containing a total of at least 2 carbon atoms and a total of up to 11 carbon atoms, and may also include one or more heteroatoms selected from the group consisting of O, S, and N. For certain of these embodiments, R″ contains one to ten carbon atoms.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the α-amino acid is selected from the group consisting of racemic, D-, and L-amino acids.

In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—.

In certain embodiments, Q is selected from the group consisting of a bond, —C(O)—, —S(O)$_2$—, and —C(R$_6$)—N(R$_8$)—.

In certain embodiments, Q is —C(O)—.

In certain embodiments, V is selected from the group consisting of —C(R$_6$)—, —O—C(R$_6$)—, —N(R$_8$)—C(R$_6$)—, and —S(O)$_2$—.

In certain embodiments, V is selected from the group consisting of —C(O)— and —N(R$_8$)—C(O)—.

In certain embodiments, V is —C(O)—.

In certain embodiments, W is selected from the group consisting of a bond, —C(O)—, and —S(O)$_2$—.

In certain embodiments, W is a bond.

For certain embodiments, X is selected from the group consisting of a bond, C$_{1-4}$ alkylene and C$_{2-4}$ alkenylene.

For certain embodiments, X is a bond or C$_{1-4}$ alkylene.

For certain embodiments, X is a bond, methylene, or ethylene.

In certain embodiments, X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups.

In certain embodiments, X' is alkylene.

In certain embodiments, X' is phenylene.

In certain embodiments, Y is selected from the group consisting of a bond, —C(R$_6$)—, —S(O)$_2$—, —S(O)$_2$—N(R$_8$)—,

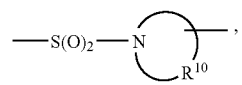

—C(O)—O—, —C(R$_6$)—N(R$_8$)—, —C(O)—N(R$_8$)—S(O)$_2$—, —C(R$_6$)—N(R$_8$)—C(O)—,

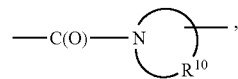

—C(O)—C(O)—, —C(O)—C(O)—O—, and —C(=NH)—N(R$_8$)—.

In certain embodiments, Y is selected from the group consisting of —C(O)—, —S(O)$_2$—, —S(O)$_2$—N(R$_8$)—, —C(O)—O—, and —C(O)—N(R$_8$)—.

In certain embodiments, Y is selected from the group consisting of —C(O)—, —S(O)$_2$—, and —C(O)—N(H)—.

In certain embodiments, Y is a bond.

In certain embodiments, Y' is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

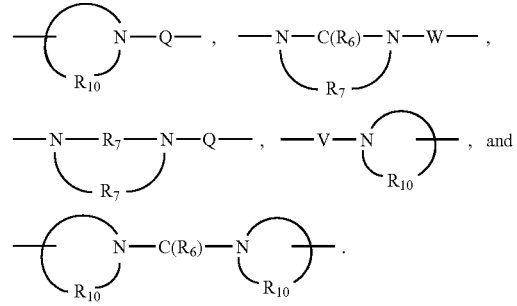

In certain embodiments, Y' is —N(R$_8$)—C(O)—, —N(R$_8$)—S(O)$_2$—, —N(R$_8$)—C(O)—N(R$_8$)—, or

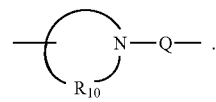

In certain embodiments, Z' is a bond or —O—.

In certain embodiments, Z' is a bond.

In certain embodiments, Z' is —O—.

In certain embodiments, a and b are independently integers from 1 to 6 with the proviso that a+b is ≦7.

In certain embodiments, a and b are each 2.

In certain embodiments, n is an integer form 0 to 4.

In certain embodiments, n is 0 or 1.

In certain embodiments, n is 0.

In certain embodiments, p is an integer form 0 to 3.

In certain embodiments, p is 0 or 1.

In certain embodiments, p is 0.

In certain embodiments, m is 0 or 1; with the proviso that when m is 1, then n is 0 or 1.

In certain embodiments, m is 0 or 1; with the proviso that when m is 1, then p is 0 or 1.

In certain embodiments, m is 0.

In certain embodiments, m is 1.

For certain embodiments, the present invention provides a pharmaceutical composition comprising a therapeutically effective amount of a compound or salt of any one of the above embodiments of Formulas I, II, III, IV, V, VI, VII, and VIIIa, and a pharmaceutically acceptable carrier.

For certain embodiments, the present invention provides a method of inducing cytokine biosynthesis in an animal comprising administering an effective amount of a compound or salt of any one of the above embodiments of Formulas I, II, III, IV, V, VI, VII, and VIIIa, or a pharmaceutical composition comprising an effective amount of a compound or salt of any one of the above embodiments of Formulas I, II, III, IV, V, VI, VII, and VIIIa to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

For certain embodiments, the present invention provides a method of treating a viral disease in an animal comprising administering a therapeutically effective amount of a compound or salt of any one of the above embodiments of Formulas I, II, III, IV, V, VI, VII, and VIIIa, or a pharmaceutical composition comprising a therapeutically effective amount of a compound or salt of any one of the above embodiments of Formulas I, II, III, IV, V, VI, VII, and VIIIa to the animal.

For certain embodiments, the present invention provides a method of treating a neoplastic disease in an animal comprising administering a therapeutically effective amount of a compound or salt of any one of the above embodiments of Formulas I, II, III, IV, V, VI, VII, and VIIIa, or a pharmaceutical composition comprising a therapeutically effective amount of a compound or salt of any one of the above embodiments of Formulas I, II, III, IV, V, VI, VII, and VIIIa to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I where R, $R_1$, $R_{2-2}$, $R_{2-3}$, X, Y, and n are as defined above, and Hal is chloro, bromo, or iodo. In step (1) of Reaction Scheme I, a quinoline-3,4-diamine of Formula X is reacted with a carboxylic acid equivalent, which is selected such that it will provide the desired —X—$CH_2$-Hal substituent in a 1H-imidazo[4,5-c]quinoline of Formula XI. Suitable carboxylic acid equivalents include ortho esters, acid halides, and imidates or salts thereof. Many compounds of Formula X are known and can be readily prepared using known synthetic routes; see for example, U.S. Pat. Nos. 4,689,338 (Gerster), 4,929,624 (Gerster et al.), 5,268,376 (Gerster), 5,389,640 (Gerster et al.), 6,331,539 (Crooks et al.), 6,451,810 (Coleman et al.), 6,541,485 (Crooks et al.), 6,660,747 (Crooks et al.), 6,670,372 (Charles et al.), 6,683,088 (Crooks et al.), 6,656,938 (Crooks et al.), 6,664,264 (Dellaria et al.), 6,677,349 (Griesgraber); and U.S. Patent Publication Application No. US 2004/0147543 (Hays et al.).

When the carboxylic acid equivalent used in step (1) is an imidate of formula Hal-$CH_2$—X—C(=NH)—O-alkyl or a salt thereof, the reaction is conveniently carried out by combining a quinoline-3,4-diamine of Formula X with the imidate in a suitable solvent such 1,2-dichloroethane or chloroform. The reaction can be carried out at an elevated temperature such as 80° C. or the reflux temperature of the solvent. The product can be isolated by conventional methods. Some imidates of formula Hal-$CH_2$—X—C(=NH)—O-alkyl are known; others can be prepared by known methods. Ethyl chloroacetimidate hydrochloride, which can be used to provide a compound of Formula XI in which X is a bond, is a known compound that can be prepared according to the literature procedure: Stillings, M. R. et al., *J. Med. Chem.*, 29, pp. 2280-2284 (1986).

When the carboxylic acid equivalent is an acid halide of formula Hal-$CH_2$—X—C(O)Cl or Hal-$CH_2$—X—C(O)Br, the reaction is conveniently carried out by adding the acid halide to a solution of a quinoline-3,4-diamine of Formula X in a suitable solvent such as dichloromethane or 1,2-dichloroethane in the presence of a tertiary amine such as triethylamine. The reaction can be carried out at ambient temperature or at a sub-ambient temperature. The product can be isolated by conventional methods.

The reaction with an acid halide of formula Hal-$CH_2$—X—C(O)Cl or Hal-$CH_2$—X—C(O)Br may be carried out in two parts, which include (i) adding the acid halide to a solution of a quinoline-3,4-diamine of Formula X in a suitable solvent such as dichloromethane or 1,2-dichloroethane optionally in the presence of a tertiary amine such as triethylamine to afford an amide intermediate and (ii) cyclizing to provide a 1H-imidazo[4,5-c]quinoline of Formula XI. The amide intermediate from part (i) can be optionally isolated using conventional techniques. The cyclization in part (ii) may be carried out by heating the amide intermediate from part (i) in a suitable solvent such as toluene. The cyclization in part (ii) can also be carried out in the presence of a base such as triethylamine.

In step (2) of Reaction Scheme I a 1H-imidazo[4,5-c]quinoline of Formula XI is oxidized to provide an N-oxide of Formula XII using a conventional oxidizing agent that is capable of forming N-oxides. The reaction can be carried out by treating a solution of a compound of Formula XI in a suitable solvent such as chloroform or dichloromethane with 3-chloroperoxybenzoic acid at room temperature, and the product can be isolated by conventional methods.

In step (3) of Reaction Scheme I, a 1H-imidazo[4,5-c]quinoline-5N-oxide of Formula XII is aminated to provide a 1H-imidazo[4,5-c]quinolin-4-amine of Formula XIII. Step (3) involves the activation of an N-oxide of Formula XII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XII in a suitable solvent such as dichloromethane or chloroform and then adding p-toluenesulfonyl chloride. The reaction can be carried out at room temperature, and the product or a pharmaceutically acceptable salt thereof can be isolated from the reaction mixture using conventional methods.

Alternatively, the oxidation and amination can be carried out as a one-pot procedure without isolating the N-oxide of Formula XII by adding 3-chloroperoxybenzoic acid to a solution of a compound of Formula XI in a solvent such as dichloromethane or chloroform and then adding ammonium hydroxide and p-toluenesulfonyl chloride. The product of Formula XIII or a pharmaceutically acceptable salt thereof can be isolated by conventional methods. Some compounds of Formula XIII are known, see for example, International Publication Nos. WO2005/048933 and WO2005/048945.

In step (4) of Reaction Scheme I, the Hal group of a 1H-imidazo[4,5-c]quinolin-4-amine of Formula XIII is displaced with a hydroxylamine of formula $HN(Y—R_{2-3})OR_{2-2}$ or a salt thereof. The reaction is conveniently carried out by combining a hydroxylamine salt of the formula $HN(Y—R_{2-3})OR_{2-2} \cdot HCl$ with a compound of Formula XIII in a suitable solvent, such as N,N-dimethylformamide (DMF), in the presence of a base such as triethylamine. The reaction can be carried out at room temperature or at an elevated temperature such as 50° C. Some hydroxylamine salts of the formula $HN(Y—R_{2-3})OR_{22} \cdot HCl$ can be obtained commercially. For example N,O-dimethylhydroxylamine hydrochloride, methoxylamine hydrochloride, and N-methylhydroxylamine hydrochloride are commercially available compounds that can be used to make preferred compounds of Formula XIV, wherein Y is a bond. Other hydroxylamine salts of the formula $HN(Y—R_{2-3})OR_{2-2} \cdot HCl$ can be prepared using conventional synthetic methods. The product of Formula XIV, a subgenus of Formulas I and III, or a pharmaceutically acceptable salt thereof can be isolated using conventional methods.

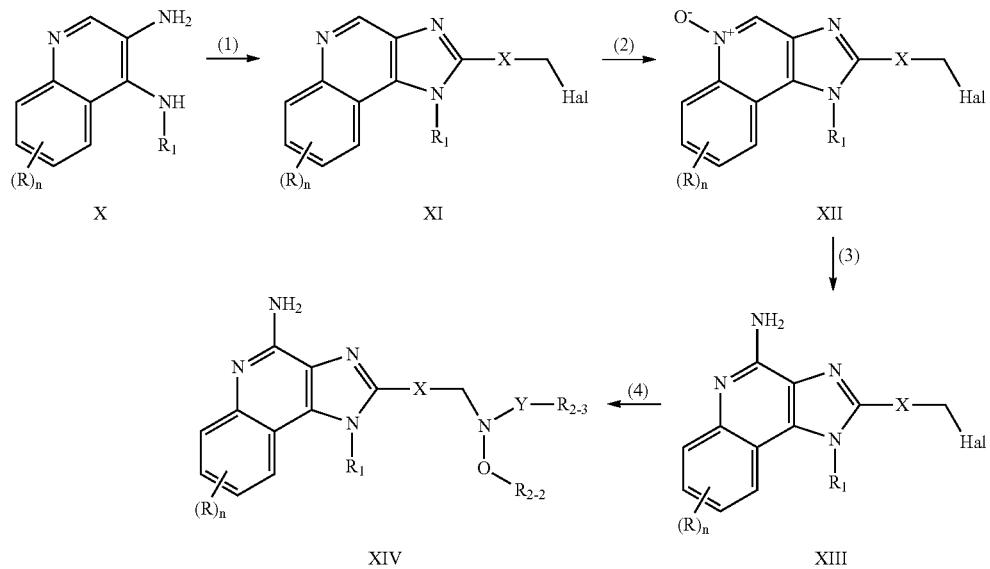

Reaction Scheme I

Compounds of the invention can be prepared according to Reaction Scheme II where R, $R_1$, $R_{2-1}$, $R_{2-2}$, $R_{2-3}$, X, Y, and n are as defined above, and P is a hydroxy protecting group. In step (1) of Reaction Scheme II, a compound of Formula X or a salt thereof is reacted with a carboxylic acid or an equivalent thereof to provide a compound of Formula XV. Suitable equivalents to carboxylic acid include acid anhydrides of Formula $O[C(O)—X—CH_2—O—P]_2$ and acid chlorides of Formula $Cl—C(O)—X—CH_2—O—P$. The reaction is conveniently carried out by using the conditions described in step (1) of Reaction Scheme I for the reaction with acid chlorides. Some compounds of Formula $Cl—C(O)—X—O—P$, such as acetoxyacetyl chloride, methoxyacetyl chloride, and 2-methoxypropionyl chloride, are commercially available. Others can be prepared by known synthetic methods.

In step (2) of Reaction Scheme II, the protecting group of a 1H-imidazo[4,5-c]quinoline of Formula XV is removed to provide a hydroxyalkyl-substituted 1H-imidazo[4,5-c]quinoline of Formula XVI. The deprotection can be carried out using a variety of methods depending on which P group is present. When P is $—C(O)—CH_3$, the reaction is conveniently carried out by adding lithium hydroxide monohydrate to a solution or suspension of the compound of Formula XV in a suitable solvent or solvent system such as tetrahydrofuran:methanol:water. The reaction can be carried out at room temperature, and the product can be isolated by conventional methods.

In step (3) of Reaction Scheme II, a hydroxyalkyl-substituted 1H-imidazo[4,5-c]quinoline of Formula XVI is oxidized to an aldehyde-substituted 1H-imidazo[4,5-c]quinoline of Formula XVII using one of many conventional methods. The oxidation is conveniently carried out by adding Dess-Martin periodinane, [1,1,1-tris(acetyloxy)-1,1-dihydro-1,2-benziodoxol-3(1H)-one], to a solution or suspension of a hydroxyalkyl-substituted 1H-imidazo[4,5-c]quinoline of Formula XVI in a suitable solvent such as dichloromethane.

The reaction can be carried out at room temperature, and the product can be isolated by conventional methods.

Alternatively, certain aldehyde-substituted 1H-imidazo[4,5-c]quinolines of Formula XVII in which X is a bond can be prepared from 1H-imidazo[4,5-c]quinolines with a hydrogen at the 2-position, many of which are known; see, for example, U.S. Pat. Nos. 4,689,338 (Gerster) and 5,268,376 (Gerster). The hydrogen at the 2-position of a 1H-imidazo[4,5-c]quinoline may undergo lithiation with butyllithium, and subsequent substitution with DMF provides a compound of Formula XVII in which X is a bond. The reaction is conveniently carried out in a suitable solvent such as THF at a subambient temperature such as −78° C. The product or a pharmaceutically acceptable salt thereof can be isolated by conventional methods.

In step (4) of Reaction Scheme II, an aldehyde-substituted 1H-imidazo[4,5-c]quinoline of Formula XVII is converted to an aldoxime of Formula XVIII. The reaction is conveniently carried out by adding a hydroxylamine salt of the formula $NH_2OR_{2-2} \cdot HCl$, optionally in a suitable solvent such as water, to a solution or suspension of a compound of Formula XVII, in a suitable solvent, such as ethanol or methanol. Optionally a base such as aqueous sodium hydroxide can be added. The reaction can be carried out at room temperature or at an elevated temperature such as the reflux temperature of the solvent. Hydroxylamine salts of the formula $NH_2OR_{2-2} \cdot HCl$ can be obtained commercially or they can be prepared using conventional synthetic methods. The product or a pharmaceutically acceptable salt thereof is obtained as a mixture of E and Z isomers and can be isolated using conventional methods.

In steps (5) and (6) of Reaction Scheme II, an aldoxime-substituted 1H-imidazo[4,5-c]quinoline of Formula XVIII is first oxidized to an N-oxide of Formula XIX, which is then aminated to provide a compound of Formula XX, which is a subgenus of Formulas I and III. Steps (5) and (6) of Reaction Scheme II can be carried out according to the methods described in steps (2) and (3) of Reaction Scheme I, and the product can be isolated by conventional methods.

In step (7) of Reaction Scheme II, an aldoxime-substituted 1H-imidazo[4,5-c]quinolin-4-amine of Formula XX is treated with a Grignard reagent of the formula $R_{2-1}MgHalide$ to form a hydroxylamine of Formula XXI, a subgenus of Formulas I and III. Several Grignard reagents are commercially available; others can be prepared using known synthetic methods. The reaction is conveniently carried out by adding a solution of two equivalents of the Grignard reagent to a solution of the compound of Formula XX in a suitable solvent such as THF. The reaction can be carried out at room temperature, and the product can be isolated using conventional methods. Alternatively, to prepare a compound of Formula XXI wherein $R_{2-1}$ is hydrogen, an oxime of Formula XX can be treated with a hydride reducing agent. The reduction is conveniently carried out by treating an oxime of Formula XX with excess sodium cyanoborohydride in a suitable solvent or solvent mixture such as methanol/acetic acid. The reaction can be carried out at ambient temperature. The product or a pharmaceutically acceptable salt thereof can be isolated using conventional methods.

In step (8) of Reaction Scheme II, a hydroxylamine of Formula XXI is converted to a compound of Formula XXII, a subgenus of Formulas I and III. Step (8) is carried out using conventional methods. For example, sulfonamides of Formula XII (Y is $-S(O)_2-$) can be prepared by reacting a compound of Formula XXI with a sulfonyl chloride of formula $R_{2-3}S(O)_2Cl$ or a sulfonic anhydride of Formula $[R_{2-3}S(O)_2]_2O$. The reaction can be carried out at room temperature in an inert solvent such as chloroform, dichloromethane, or N,N-dimethylacetamide (DMA) by adding the sulfonyl chloride or sulfonic anhydride to a compound of Formula XI in the presence of a base such as N,N-diisopropylethylamine, triethylamine, or pyridine.

Sulfamides of Formula XXII (Y is $-S(O)_2-N(R)-$ or

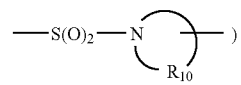
)

can be prepared by reacting a compound of Formula XXI with sulfuryl chloride to generate a sulfamoyl chloride in situ, and then reacting the sulfamoyl chloride with an amine of formula $HN(R_8)R_{2-3}$, or

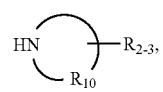

or by reacting a compound of Formula XXI with a sulfamoyl chloride of formula $R_{2-3}(R_8)NS(O)_2Cl$ or

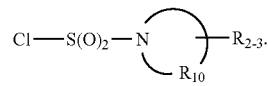

The product or a pharmaceutically acceptable salt thereof can be isolated using conventional methods. Many sulfonyl chlorides of formula $R_{2-3}S(O)_2Cl$, amines of formulas $HN(R_8)R_{2-3}$, and

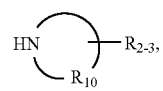

and some sulfamoyl chlorides of formulas $R_{2-3}(R_8)NS(O)_2Cl$ and

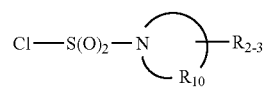

are commercially available; others can be prepared using known synthetic methods.

Amides of Formula XXII (Y is $-C(O)-$) can be prepared from hydroxylamines of Formula XXI using conventional methods. For example, a compound of Formula XXI can be reacted with an acid chloride of formula $R_{2-3}C(O)Cl$. The reaction can be carried out by adding the acid chloride to a solution of a compound of Formula XXI in a suitable solvent such as chloroform or DMA, optionally in the presence of a base such as N,N-diisopropylethylamine, triethylamine, or pyridine, at ambient temperature. The product or a pharmaceutically acceptable salt thereof can be isolated using conventional methods.

Ureas and thioureas of Formula XXII (Y is $-C(O)-N(R_8)-$, $-C(S)-N(R_8)-$, $-C(O)-N(R_8)-S(O)_2-$, $-C(O)-N(R_8)-C(O)-$, $-C(S)-N(R_8)-C(O)-$, or

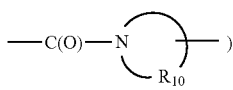

can be prepared from hydroxylamines of Formula XXI using conventional methods. For example, a compound of Formula VI can be reacted with an isocyanate of formula $R_{2-3}N=C=O$. The reaction can be carried out by adding the isocyanate to a solution of a compound of Formula XXI in a suitable solvent such as chloroform or DMA, optionally in the presence of a base such as N,N-diisopropylethylamine, or triethylamine, at room temperature. Alternatively, a compound of Formula XXI can be reacted with a thioisocyanate of formula $R_{2-3}N=C=S$, a sulfonyl isocyanate of formula $R_{2-3}S(O)_2N=C=O$ or a carbamoyl chloride of formula $R_{2-3}NC(O)Cl$ or

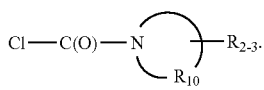

The product or a pharmaceutically acceptable salt thereof can be isolated using conventional methods.

Reaction Scheme II can be modified after step (3) to introduce a $R_{2-4}$ group that is other than hydrogen. In this modification, an aldehyde-substituted 1H-imidazo[4,5-c]quinoline of Formula XVII is treated with a Grignard reagent of the formula $R_{2-4}MgHalide$, which adds to the aldehyde to form a secondary alcohol. Several Grignard reagents are commercially available; others can be prepared using known synthetic methods. The reaction is conveniently carried out by adding a solution of the Grignard reagent to a solution of the compound of Formula XVII in a suitable solvent such as THF. The reaction can be carried out at room temperature, and the product can be isolated using conventional methods. The secondary alcohol is then oxidized to a ketone using conventional methods. The reaction is conveniently carried out using Dess-Martin periodinane under the conditions described in step (3) of Reaction Scheme II. The reaction may also be carried out under Swern conditions by adding the secondary alcohol followed by triethylamine to a mixture of oxalyl chloride and dimethylsulfoxide in a suitable solvent such as dichloromethane. The reaction can be carried out at a sub-ambient temperature, and the product can be isolated by conventional methods. Steps (4) through (8) of Reaction Scheme II can then be carried out to provide a hydroxylamine of the invention with an $R_{2-4}$ group that is other than hydrogen.

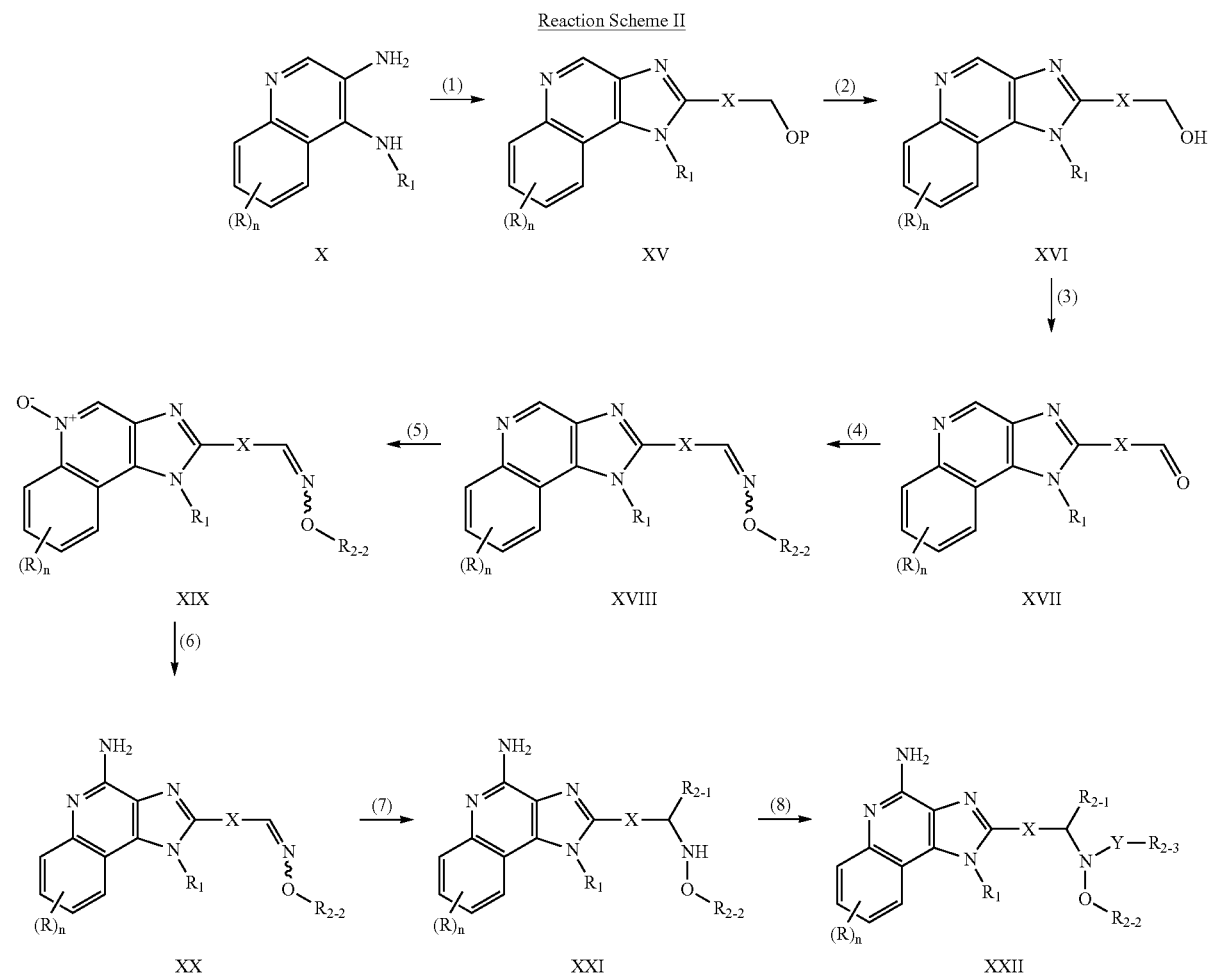

Reaction Scheme II

Compounds of the invention can be prepared according to Reaction Scheme III, wherein R, $R_1$, $R_{2-1}$, $R_{2-2}$, X, and n are as defined above. In step (1) of Reaction Scheme III, a quinoline-3,4-diamine of Formula X is reacted with a ketal-substituted carboxylic acid or equivalent thereof of the formula

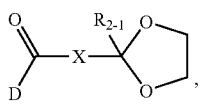

wherein D can be —OH, —Cl, Br, or a leaving group prepared using conventional hydroxy activation chemistry, such as employing N-hydroxysuccinimide as an activating agent. Ketals of this formula are readily prepared from esters of formula alkyl-O—C(O)—X—C(O)—$R_{2-1}$ using conventional methods. For example, the ketone can be converted to a ketal by heating with ethylene glycol in the presence of pyridinium p-toluenesulfonate in a suitable solvent such as toluene. The carboxyl group can then be activated by first hydrolyzing the ester under basic conditions, for example with sodium hydroxide in water and a lower alcohol, and then reacting with N-hydroxysuccinimide in the presence of 4-methylmorpholine and 1-(3-dimethylaminopropyl)-3-ethylcarbodiimide hydrochloride in a suitable solvent such as dichloromethane. The reaction shown in step (1) of Reaction Scheme III can be carried out according to the methods described for reaction with acid chlorides in step (1) of Reaction Scheme I, or it can be conveniently carried out by heating a quinoline-3,4-diamine of Formula X with a ketal shown above in a suitable solvent such as pyridine. The reaction can be run at the reflux temperature of the solvent, and the product of Formula XXIII can be isolated by conventional methods.

In step (2) of Reaction Scheme III, a 1H-imidazo[4,5-c]quinoline of Formula XXIII is converted to the N-oxide of Formula XXIV using the method described in step (2) of Reaction Scheme I.

In step (3) of Reaction Scheme III, the N-oxide of Formula XXIV is aminated to afford the compound of Formula XXV using one of the methods described in step (3) of Reaction Scheme I.

In step (4) of Reaction Scheme III, a ketal of Formula XXV is converted to a ketone of Formula XXVI by acid-catalyzed hydrolysis. The reaction is conveniently carried out by adding a strong acid, such as hydrochloric acid, to a ketal of Formula XXV. The reaction may be carried out at room temperature in a suitable solvent such as water, and the product can be isolated by conventional methods.

In step (5) of Reaction Scheme III, a ketone-substituted 1H-imidazo[4,5-c]quinolin-4-amine of Formula XXVI is converted to an oxime of Formula XXVII. The reaction is conveniently carried out as described in step (4) of Reaction Scheme II, and the product or a pharmaceutically acceptable salt thereof can be isolated by conventional methods.

Reaction Scheme III

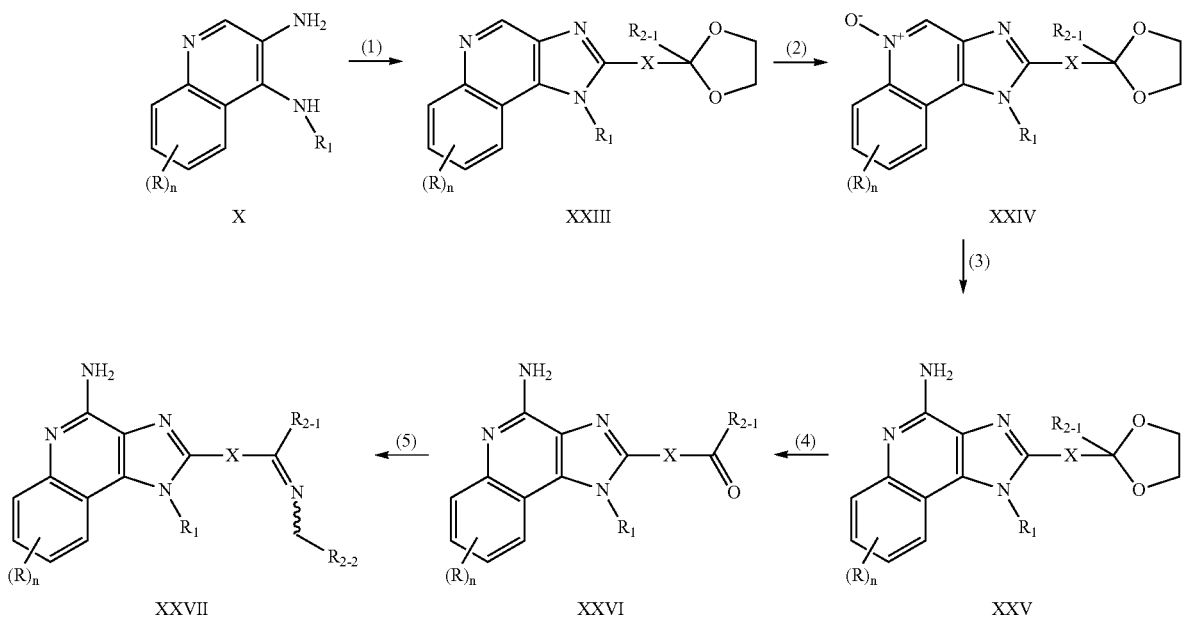

Any of Reaction Schemes I through III may be carried out using a [1,5]naphthyridine-3,4-diamine instead of a quinoline-3,4-diamine of Formula X as the starting material to prepare 1H-imidazo[4,5-c][1,5]naphthyridines of the invention. Several [1,5]naphthyridine-3,4-diamines and their preparation are known; see, for example, U.S. Pat. Nos. 6,194,425 (Gerster) and 6,518,280 (Gerster).

Compounds of the invention can be prepared according to Reaction Scheme IV, wherein $R_{2-1}$, and Z are as defined above; $X_b$ is selected from the group consisting of a bond and $C_{1-4}$ alkylene; $R_b$ is selected from the group consisting of hydroxy, alkyl, alkoxy, —$N(R_9)_2$; n is 0 to 4; and $R_{1b}$ is a subset of $R_1$ as defined above that does not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents. Compounds of Formula XXVIII can be prepared by the oxidation and amination of a compound of Formula XVI according to steps (2) and (3) of Reaction Scheme I. In step (1) of Reaction Scheme IV, a compound of Formula XXVIII is reduced to a 6,7,8,9-tetrahydro compound of Formula XXIX. The reaction is conveniently carried out under heteroegeneous hydrogenation conditions by adding platinum (IV) oxide to a solution of the compound of Formula XXVIII in trifluoroacetic acid and placing the reaction under hydrogen pressure. The reaction can be carried out on a Parr apparatus at room temperature. The product or a pharmaceutically acceptable salt thereof can be isolated by conventional methods. Steps (2) through (6) of Reaction Scheme IV can then be used to convert a compound of Formula XXIX to a compound of Formula IVb, a subgenus of Formulas I and IV. Steps (2) through (6) can be carried out, for example, according to steps (3), (4), (7), and (8) of Reaction Scheme II. Compounds of Formula IVb can also be made by treating a compound of Formula XXIX with thionyl chloride under conventional conditions to provide a chloroalkyl-substituted 6,7,8,9-tetrahydro compound, which can then be treated according to step (4) of Reaction Scheme I. The product of Formula IVb or a pharmaceutically acceptable salt thereof can be isolated by conventional methods. 6,7,8,9-Tetrahydro-1H-imidazo[4,5-c][1,5]naphthyridin-4-amines can also be prepared using this Reaction Scheme.

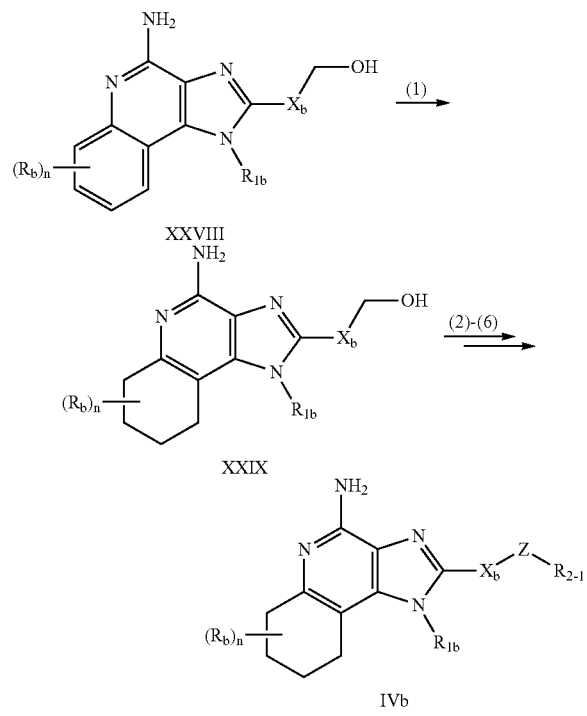

Reaction Scheme IV

Compounds of the invention can be prepared according to Reaction Scheme V, wherein R, $R_1$, $R_{2-1}$, X, and Z are as defined above; n is 0 or 1; hal is —Br or —I; and $R_{3a}$ and $R_{3b}$ are as defined below. Compounds of Formula XXX, a subgenus of Formulas I and III, can be prepared according to the methods described in Reaction Scheme I, II, or III beginning with a compound of Formula X, wherein one of the R groups is —Br, or —I. These halogen-substituted quinolines are known or can be prepared by known methods; see, for example, U.S. Patent Application Publication No. US 2004/0147543 (Hays et al.) and the references cited therein.

In step (1) of Reaction Scheme V, a halogen-substituted 1H-imidazo[4,5-c]quinolin-4-amine of Formula X) can undergo known palladium-catalyzed coupling reactions such as the Suzuki coupling and the Heck reaction. For example, a halogen-substituted compound of Formula XXX undergoes Suzuki coupling with a boronic acid of Formula $R_{3a}$—B (OH)$_2$, an anhydride thereof, or a boronic acid ester of Formula $R_{3a}$—B(O-alkyl)$_2$, wherein $R_{3a}$ is —$R_{4b}$, —X'$_a$—$R_4$, —X'$_b$—Y'—$R_4$, or —X'$_b$—$R_5$; where X'$_a$ is alkenylene; X'$_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y' are as defined above. The Suzuki coupling is conveniently carried out by combining a compound of Formula XXX with a boronic acid or an ester or anhydride thereof in the presence of palladium (II) acetate, triphenylphosphine, and a base such as sodium carbonate in a suitable solvent such as n-propanol or solvent mixture such as n-propanol/water. The reaction can be carried out at an elevated temperature (e.g., 80-100° C.). Many boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods. See, for example, Li, W. et al, *J. Org. Chem.*, 67, 5394-5397 (2002). The product of Formula IIIb, a subgenus of Formulas I and III, or a pharmaceutically acceptable salt thereof can be isolated by conventional methods.

The Heck reaction can also be used in step (1) of Reaction Scheme V to provide compounds of Formula IIIb, wherein $R_{3a}$ is —X'$_a$—$R_{4b}$ or —X'$_a$—Y'—$R_4$, wherein X'$_a$, Y', $R_{4b}$, and $R_4$ are as defined above. The Heck reaction is carried out by coupling a compound of Formula XXX with a compound of the Formula $H_2C$=$C(H)$—$R_{4b}$ or $H_2C$=$C(H)$—Y'—$R_4$. Several of these vinyl-substituted compounds are commercially available; others can be prepared by known methods. The reaction is conveniently carried out by combining the compound of Formula XXX and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100° C.-120° C. under an inert atmosphere. The product of Formula IIIb or a pharmaceutically acceptable salt thereof can be isolated using conventional methods.

Compounds of Formula IIIb, wherein $R_{3a}$ is —X'$_c$—$R_4$, X'$_c$ is alkynylene, and $R_4$ is as defined above, can also be prepared by palladium catalyzed coupling reactions such as the Stille coupling or Sonogashira coupling. These reactions are carried out by coupling a compound of Formula XXX with a compound of the Formula (alkyl)$_3$Sn—C≡C—$R_4$, (alkyl)$_3$Si—C≡C—$R_4$, or H—C≡C—$R_4$.

Some compounds of Formula IIIb prepared as described above by palladium-mediated coupling reactions, wherein $R_{3a}$ is —X'$_a$—$R_4$, —X'$_a$—Y'—$R_4$, —X'$_{b2}$—Y'—$R_4$, —X'$_{b2}$—$R_5$, or —X'$_c$—$R_4$, where X'$_{b2}$ is alkenylene interrupted or terminated by arylene or heteroarylene, and X'$_a$, X'$_c$, Y', $R_4$, and $R_5$ are as defined above, can undergo reduction of the alkenylene or alkynylene group present in step (2) of Reaction Scheme V to provide compounds of Formula IIIc wherein $R_{3b}$ is —X'$_d$—$R_4$, —X'$_d$—Y'—$R_4$, —X'$_e$—Y'—$R_4$, or —X'$_e$—$R_5$, where X'$_d$ is alkylene; X'$_e$ is alkylene interrupted or terminated by arylene or heteroarylene; and $R_4$, $R_5$, and Y' are as defined above. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product of Formula IIIc, a subgenus of Formulas I and III, or a pharmaceutically acceptable salt thereof can be isolated using conventional methods.

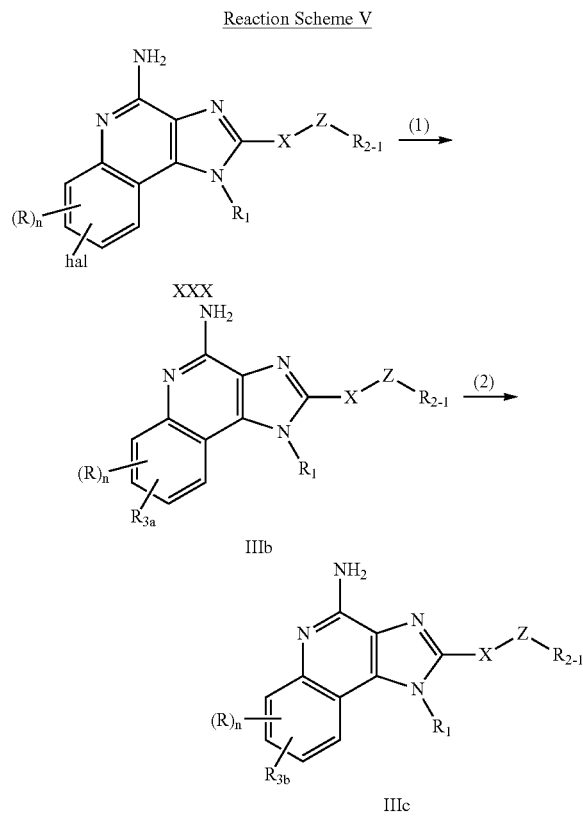

For some embodiments, compounds of the invention are prepared according to Reaction Scheme VI, where $R_1$, $R_{2-1}$, $R_{2-2}$, $R_{A1}$, $R_{B1}$, and X are as defined above, and $Z_a$ is —C($R_{2-4}$)(—N(—O$R_{2-2}$)—Y—$R_{2-3}$)— and Ph is phenyl. Steps (1) through (4) of Reaction Scheme VI can be carried out as described in steps (1) through (4) of Reaction Scheme II starting with a compound of Formula XXI. Many tetrazolo[1,5-a]pyridines of Formula XXXI are known; others can be prepared by known methods. See, for example, PCT Publication Nos. WO 2004/110991 (Lindstrom et al.), WO 2004/110992 (Lindstrom et al.), and U.S. Pat. No. 6,797,718 (Dellaria et al.).

In step (5) of Reaction Scheme VI, the tetrazolo ring is removed from a 7H-imidazo[4,5-c]tetrazolo[1,5-a]pyridine of Formula XXII by reaction with triphenylphosphine to form an N-triphenylphosphinyl intermediate of Formula XIII. The reaction with triphenylphosphine can be run in a suitable solvent such as toluene or 1,2-dichlorobenzene under an atmosphere of nitrogen with heating, for example at the reflux temperature.

In step (6) of Reaction Scheme VI, an N-triphenylphosphinyl intermediate of Formula XXXIII is hydrolyzed to provide an oxime-substituted 1H-imidazo[4,5-c]pyridin-4-amine of Formula XXXIV, a subgenus of Formulas I and II. The hydrolysis can be carried out by general methods well known to those skilled in the art, for example, by heating in a lower alkanol or an alkanol/water solution in the presence of an acid such as trifluoroacetic acid, acetic acid, or hydrochloric acid. The product can be isolated from the reaction mixture using conventional methods as the compound of Formula XXXIV or as a pharmaceutically acceptable salt thereof.

When appropriate, the methods shown in steps (7) and (8) of Reaction Scheme II may be used to convert a compound of Formula XXIV to a compound of Formula IIb using steps (7) and (8) of Reaction Scheme VI. The product or a pharmaceutically acceptable salt thereof can be isolated by conventional methods.

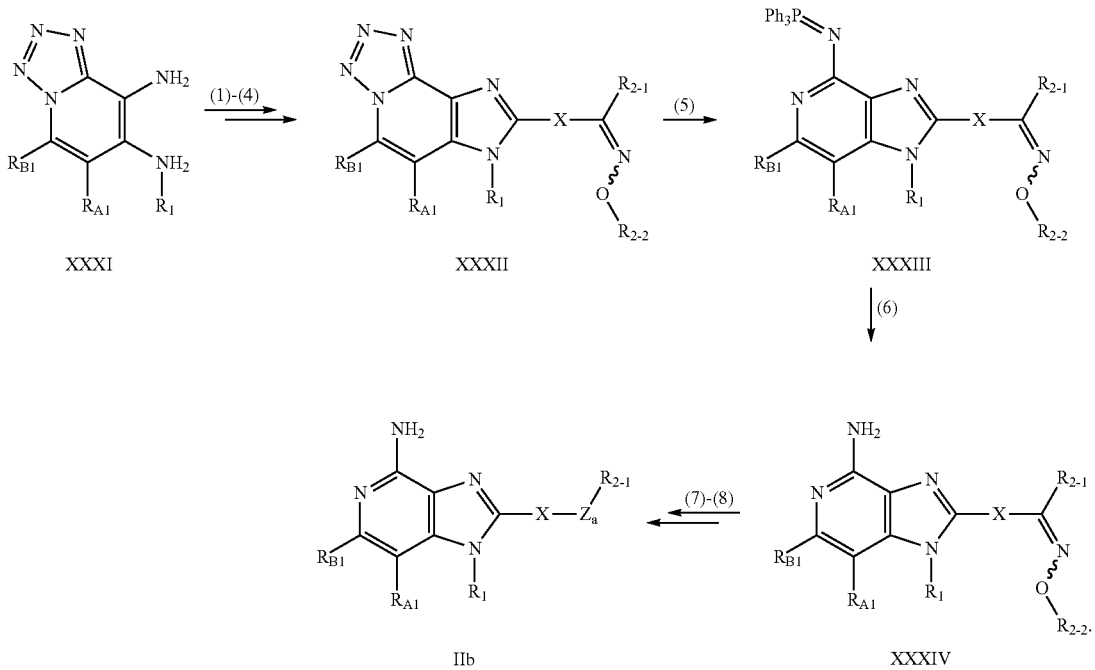

Compounds of the invention can be prepared according to Reaction Scheme VII where $R_1$, $R_{2-1}$, $R_{2-2}$, R, X, and $Z_a$ are as defined above; E is carbon (imidazoquinoline ring) or nitrogen (imidazonaphthyridine ring); n is 0 or 1; Bn is benzyl; and $R_{3c}$ is —O—$R_4$, —O—X'—$R_4$, —O—X'—Y'—$R_4$, —O—X'—Y'—X'—Y'—$R_4$, or —O—X'—$R_5$, where $R_4$, X', Y', and $R_5$ are as defined above. In step (1) of Reaction Scheme VII, an aniline or aminopyridine of Formula XXXV is treated with the condensation product generated from 2,2-dimethyl-1,3-dioxane-4,6-dione (Meldrum's acid) and triethyl orthoformate to provide an imine of Formula XXXVI. The reaction is conveniently carried out by adding a solution of an aniline or aminopyridine of Formula XXXV to a heated mixture of Meldrum's acid and triethyl orthoformate and heating the reaction at an elevated temperature. The product can be isolated using conventional methods. Many anilines and aminopyridines of Formula XXXV are commercially available; others can be prepared by known synthetic methods. For example, benzyloxypyridines of Formula XXXV can be prepared using the method of Holladay et al., *Biorg. Med. Chem. Lett.*, 8, pp. 2797-2802, (1998).

In step (2) of Reaction Scheme VII, an imine of Formula XVI undergoes thermolysis and cyclization to provide a compound of Formula XXXVII. The reaction is conveniently carried out in a medium such as DOWTHERM A heat transfer fluid at a temperature in the range of 200 to 250° C. The product can be isolated using conventional methods. Isomers of the compound of Formula XV or Formula XXVII, wherein E is nitrogen and at a different position in the ring, can also be synthesized and can be used to prepare compounds of the invention.

In step (3) of Reaction Scheme VII, a compound of Formula XXXVII is nitrated under conventional nitration conditions to provide a compound of Formula XXVIII. The reaction is conveniently carried out by adding nitric acid to the compound of Formula XXXVII in a suitable solvent such as propionic acid and heating the mixture at an elevated temperature. The product can be isolated using conventional methods.

In step (4) of Reaction Scheme VII, a 3-nitro[1,5]naphthyridin-4-ol or 3-nitroquinolin-4-ol of Formula XXVIII is chlorinated using conventional chlorination chemistry to provide a 4-chloro-3-nitro[1,5]naphthyridine or 4-chloro-3-nitroquinoline of Formula XXXIX. The reaction is conveniently carried out by treating the compound of Formula XXXVIII with phosphorous oxychloride in a suitable solvent such as DMF. The reaction can be carried out at ambient temperature or at an elevated temperature such as 100° C., and the product can be isolated using conventional methods.

In step (5) of Reaction Scheme VII, a 4-chloro-3-nitro[1,5]naphthyridine or 4-chloro-3-nitroquinoline of Formula XXI is treated with an amine of Formula $R_1$—$NH_2$ to provide a compound of Formula XL. Several amines of Formula $R_1$—$NH_2$ are commercially available; others can be prepared by known synthetic methods. The reaction is conveniently carried out by adding the amine of Formula $R_1$—$NH_2$ to a solution of the 4-chloro-3-nitro[1,5]naphthyridine or 4-chloro-3-nitroquinoline of Formula XXXIX in a suitable solvent such as dichloromethane in the presence of a tertiary amine such as triethylamine. The reaction can be carried out at ambient temperature or at a sub-ambient temperature such as, for example, 0° C. The reaction product can be isolated using conventional methods.

In step (6) of Reaction Scheme VII, a compound of Formula XL is reduced to provide a diamine of Formula XLI. The reaction can be carried out by hydrogenation using a heterogeneous hydrogenation catalyst such as platinum on carbon. The hydrogenation is conveniently carried out in a Parr apparatus in a suitable solvent such as toluene, methanol, acetonitrile, or ethyl acetate. The reaction can be carried out at ambient temperature, and the product can be isolated using conventional methods.

Alternatively, the reduction in step (6) can be carried out using nickel boride, prepared in situ from sodium borohydride and nickel(II) chloride. The reduction is conveniently carried out by adding a solution of a compound of Formula XL in a suitable solvent or solvent mixture such as dichloromethane/methanol to a mixture of excess sodium borohydride and catalytic nickel(II) chloride in methanol. The reaction can be carried out at ambient temperature. The product can be isolated using conventional methods.

Steps (7) through (12) of Reaction Scheme VII are analogous to steps (1) through (6) of Reaction Scheme II and can be carried out using the same methods.

In step (13) of Reaction Scheme VII, the benzyl group in an oxime of Formula XLII is cleaved to provide a hydroxy group. The cleavage is conveniently carried out on a Parr apparatus under hydrogenolysis conditions using a suitable heterogeneous catalyst such as palladium or platinum on carbon in a solvent such as ethanol. Alternatively, the cleavage can be carried out with an acid such as hydrogen bromide in a suitable solvent such as acetic acid at an elevated temperature, such as 65° C. The product of Formula XLIII, prepared by any of these methods, or a pharmaceutically acceptable salt thereof can be isolated using conventional methods.

In step (14) of Reaction Scheme VII, a hydroxy-substituted oxime of Formula XLIII is converted to a compound of Formula XLIV, a subgenus of Formula I, using a Williamson-type ether synthesis. The reaction is effected by treating a hydroxy-substituted compound of Formula XLIII with an aryl, alkyl, or arylalkylenyl halide of Formula Halide-$R_{4b}$, Halide-alkylene-$R_4$, Halide-alkylene-Y'—$R_4$, or Halide-alkylene-$R_5$, where $R_{4b}$ is as defined above, in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, and substituted fluorobenzenes. Other halides of these formulas can be prepared using conventional synthetic methods. The reaction is conveniently carried out by combining an alkyl, arylalkylenyl, or aryl halide with the hydroxy-substituted compound of Formula XLIII in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the halide reagent. Alternatively, step (14) may be carried out using the Ullmann ether synthesis, in which an alkali metal aryloxide prepared from the hydroxy-substituted compound of Formula XLIII reacts with an aryl halide in the presence of copper salts, to provide a compound of Formula XLIV, where $R_{3b}$ is —O—$R_{4b}$, —O—$X'_f$—$R_4$, or —O—$X'_f$—Y'—$R_4$, wherein $X'_f$ is an arylene or heteroarylene, and $R_{4b}$ is as defined above. Numerous substituted and unsubstituted aryl halides are commercially available; others can be prepared using conventional methods. The product of Formula XLIV, prepared by either of these methods, or a pharmaceutically acceptable salt thereof can be isolated using conventional methods.

When appropriate, the methods shown in steps (7) and (8) of Reaction Scheme II may be used to convert a compound of Formula XLIV to a compound of Formula XLV using steps (15) and (16) of Reaction Scheme VII. The product or pharmaceutically acceptable salt thereof can be isolated by conventional methods.

Reaction Scheme VII
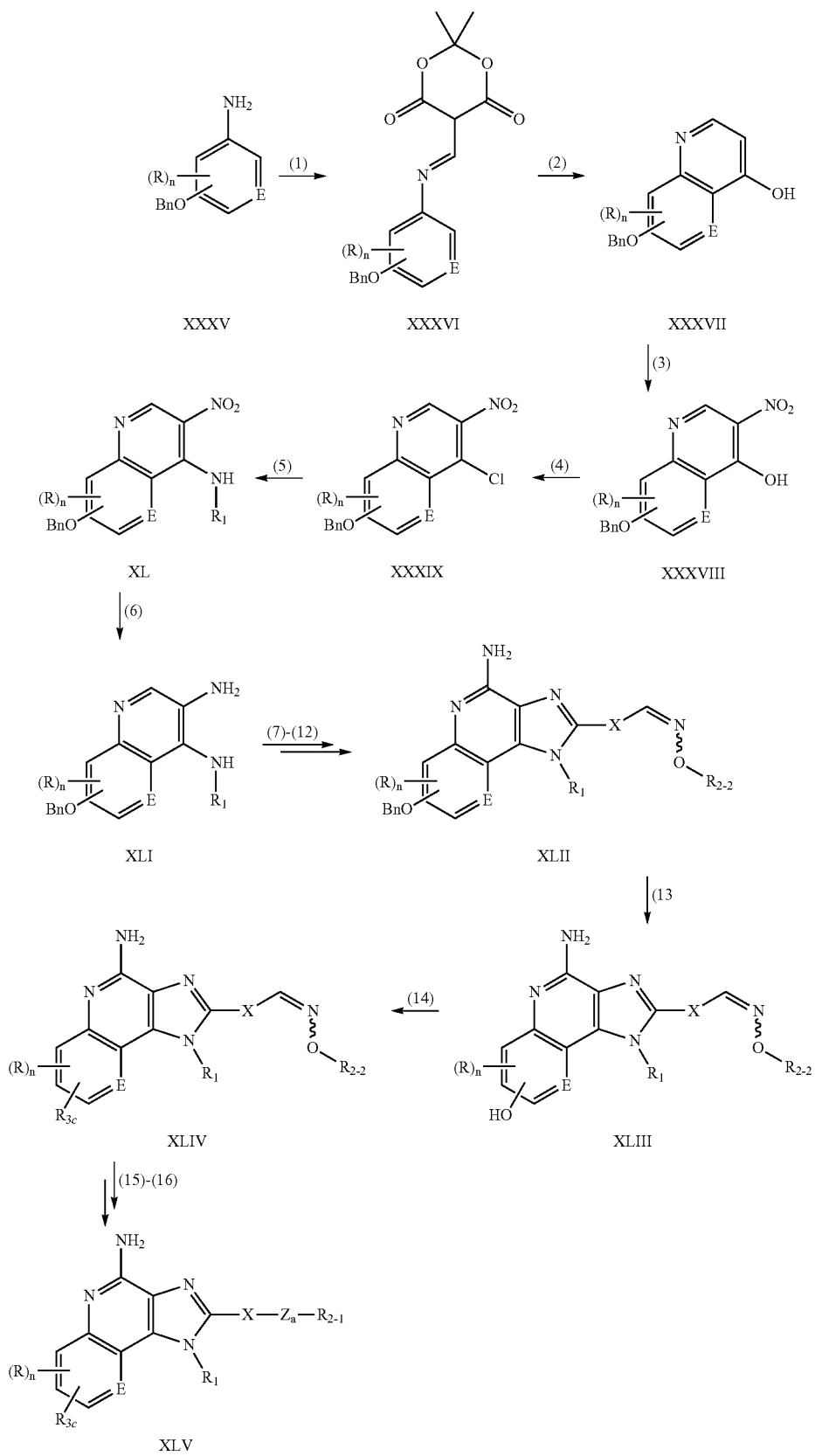

For some embodiments, naphthyridines of the invention are prepared from tetrazolo compounds of Formulas XLVI and L according to Reaction Schemes VIII and IX, wherein $R_1$, $R_{2-1}$, $R_{2-2}$, R, n, $Z_a$, and X are as defined above. Compounds of Formula XLVI and L and synthetic routes to these compounds are known; see, for example, U.S. Pat. No. 6,194,425 (Gerster).

Steps (1) through (4) of Reaction Schemes VIII and IX are analogous to steps (1) through (4) of Reaction Scheme II and can be carried out using the same methods.

The tetrazolo group of a compound of Formula XLVII or LI can then be removed in step (5) of Reaction Scheme IX or X to provide a 1H-imidazo[4,5-c]naphthyridin-4-amine of Formula XLVIII or LII, each of which is a subgenus of Formula I. The removal of the tetrazolo group can be carried out as described in steps (5) and (6) of Reaction Scheme VI or by using methods described in U.S. Pat. No. 6,194,425 (Gerster). The product or a pharmaceutically acceptable salt thereof can be isolated by conventional methods.

When appropriate, the methods shown in steps (7) and (8) of Reaction Scheme II may be used to convert a compound of Formula XLVIII or LII to a compound of Formula XLIX or LIII using steps (6) and (7) of Reaction Scheme VIII or IX, respectively. The product of Formula XLIX or LIII, each of which is a subgenus of Formula I, or a pharmaceutically acceptable salt thereof can be isolated by conventional methods.

Reaction Scheme VIII

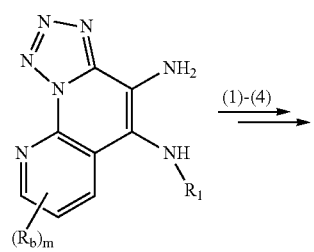

XLVI

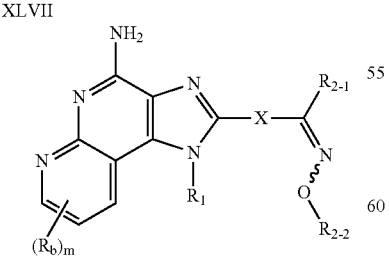

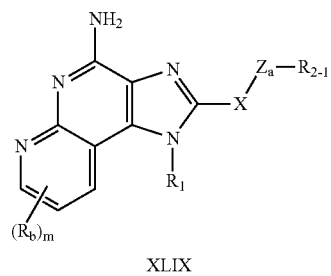

XLIX

Reaction Scheme IX

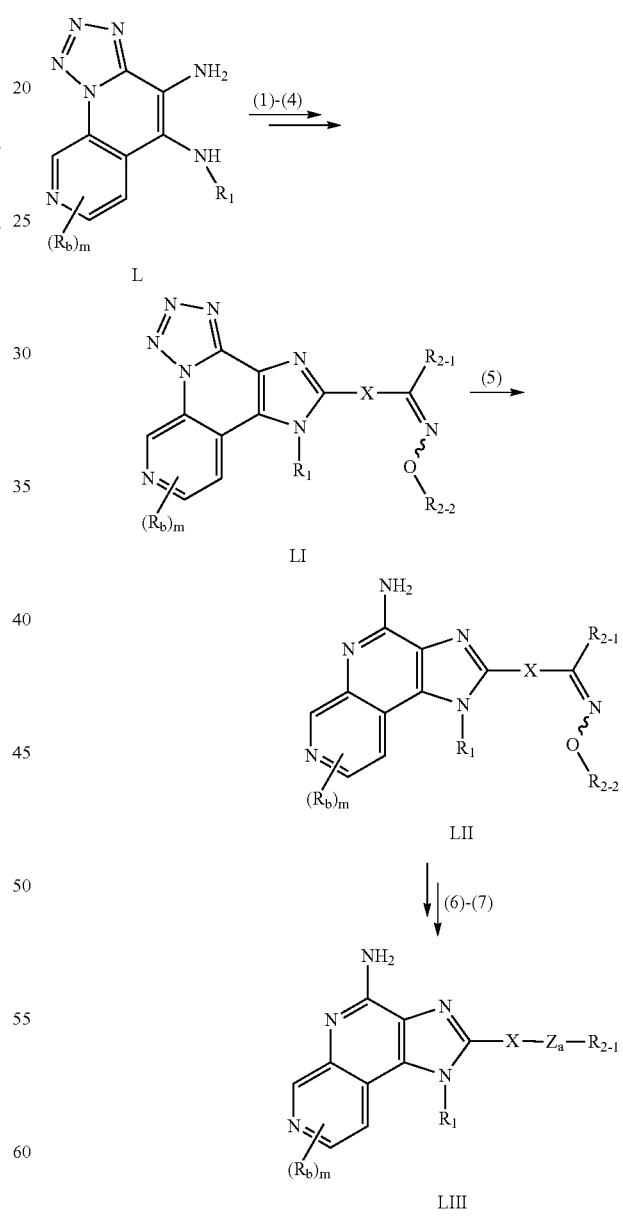

Compounds of the invention can be prepared according to Reaction Scheme X where $R_{A1}$, $R_{B1}$, $R_1$, $R_{2-2}$, $R_{2-3}$, Y, and P are as defined above and PMB is para-methoxybenzyl.

In step (1) of Reaction Scheme X, a 2,4-dichloro-3-nitropyridine of Formula LIV is reacted with an amine of formula $R_1$—$NH_2$ to provide a 2-chloro-3-nitropyridin-4-amine of Formula LV. The reaction can be carried out using the method described in step (5) of Reaction Scheme VII. Some 2,4-dichloro-3-nitropyridines of Formula LIV are known; others can be prepared using known synthetic methods. See, for example, U.S. Pat. No. 6,525,064 (Dellaria) and the references cited therein.

In step (2) of Reaction Scheme X, a 2-chloro-3-nitropyridin-4-amine of Formula LV is reduced to provide a 2-chloropyridine-3,4-diamine of Formula LVI. The reduction can be carried out using the methods described in step (6) of Reaction Scheme VII.

In step (3) of Reaction Scheme X, a 2-chloropyridine-3,4-diamine of Formula LVI is reacted with a carboxylic acid or an equivalent thereof to provide a 4-chloro-1H-imidazo[4,5-c]pyridine of Formula LVII. The reaction can be carried out using the method described in step (1) of Reaction Scheme II.

In step (4) of Reaction Scheme X, the protecting group of a 4-chloro-1H-imidazo[4,5-c]pyridine of Formula LVII is removed to provide a hydroxyalkyl-substituted 4-chloro-1H-imidazo[4,5-c]pyridine of Formula LVIII. The deprotection can be carried out using a variety of methods depending on which P group is present. When P is an ethyl group, the reaction can be carried out by adding a solution of boron tribromide in a suitable solvent to a solution or suspension of a compound of Formula LVII in a suitable solvent such as dichloromethane. The reaction can be carried out at a sub-ambient temperature such as 0° C.

In step (5) of Reaction Scheme X, a 4-chloro-1H-imidazo[4,5-c]pyridine of Formula LVIII is reacted with 4-methoxybenzylamine to provide an N-(4-methoxybenzyl)-1H-imidazo[4,5-c]pyridin-4-amine of Formula LIX. The reaction can be carried out by combining a compound of Formula LVIII with excess N-(4-methoxybenzyl)amine and excess pyridine hydrochloride in a suitable solvent such as 2,2,2-trifluoroethanol and heating (150° C.) in a microwave reactor.

In step (6) of Reaction Scheme X, the 4-methoxybenzyl group is removed from an N-(4-methoxybenzyl)-1H-imidazo[4,5-c]pyridin-4-amine of Formula LIX to provide a 1H-imidazo[4,5-c]pyridin-4-amine of Formula LX. The reaction can be carried out by treating a compound of Formula LIX with trifluoroacetic acid at ambient temperature.

In step (7) of Reaction Scheme X, a hydroxyalkyl-substituted 1H-imidazo[4,5-c]pyridin-4-amine of Formula LX is chlorinated to provide a chloroalkyl-substituted 1H-imidazo[4,5-c]pyridin-4-amine of Formula LXI. The reaction can be carried out by treating a solution of a compound of Formula LX in a suitable solvent such as chloroform with thionyl chloride. The reaction can be carried out at an elevated temperature such as the reflux temperature of the solvent.

In step (8) of Reaction Scheme X, the chloro group of a chloroalkyl-substituted 1H-imidazo[4,5-c]pyridin-4-amine of Formula LXI is displaced with a hydroxylamine of formula HN(Y—$R_{2-3}$)O$R_{2-2}$ or a salt thereof to provide a 1H-imidazo[4,5-c]pyridin-4-amine of Formula LXII, which is a subgenus of Formulas I and II. The reaction can be carried out using the methods described in step (4) of Reaction Scheme I.

In step (8a) of Reaction Scheme X, the chloro group of a chloroalkyl-substituted 1H-imidazo[4,5-c]pyridin-4-amine of Formula LXI is displaced with a hydroxylamine of formula $H_2$NO$R_{2-2}$ or a salt thereof to provide a 1H-imidazo[4,5-c]pyridin-4-amine of Formula LXIII, which is a subgenus of Formulas I and II. The reaction can be carried out using the methods described in step (4) of Reaction Scheme I.

In step (9) of Reaction Scheme X, a 1H-imidazo[4,5-c]pyridin-4-amine of Formula LXIII is further derivatized to provide a 1H-imidazo[4,5-c]pyridin-4-amine of Formula LXII, which is a subgenus of Formulas I and II. The reaction can be carried out using the methods described in step (8) of Reaction Scheme II.

Reaction Scheme X

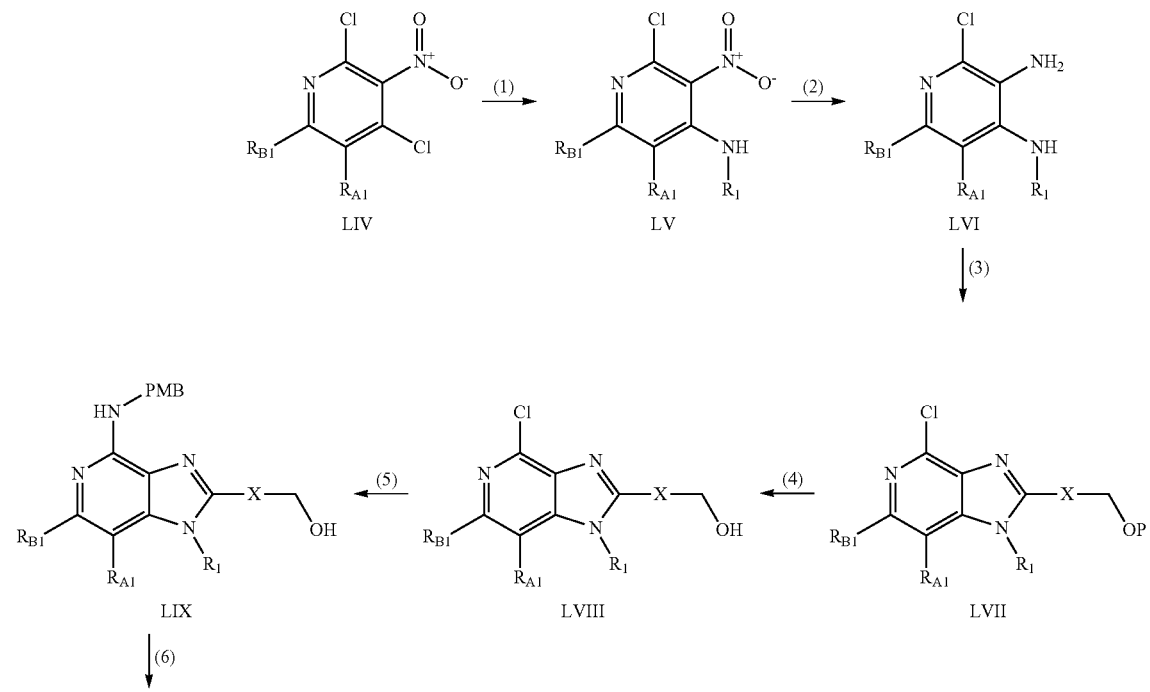

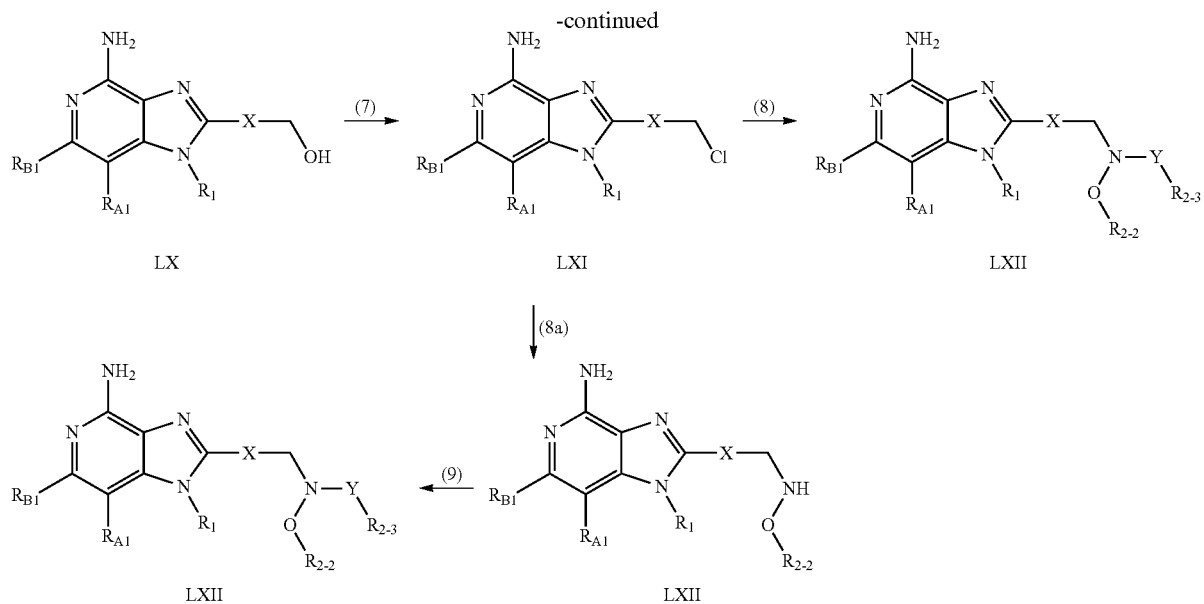

For certain embodiments, compounds of the invention can be prepared according to Reaction Scheme XI, wherein $R_{A2}$, $R_{B2}$, $R_1$, $R_{2-1}$, X, Z, and G are as defined above. Compounds of Formula Ia can be prepared according to the methods described above. The amino group of a compound of Formula Ia can be converted by conventional methods to a functional group such as an amide, carbamate, urea, amidine, or another hydrolyzable group. A compound of this type can be made by the replacement of a hydrogen atom in an amino group with a group such as —C(O)—R", α-aminoacyl, α-aminoacyl-α-aminoacyl, —C(O)—O—R", —C(O)—N(R"")—R", —C(═NY$_1$)—R", —CH(OH)—C(O)—OY$_1$, —CH(OC$_{1-4}$ alkyl)Y$_0$, —CH$_2$Y$_2$, or —CH(CH$_3$)Y$_2$; wherein R" and R"" are each independently C$_{1-10}$ alkyl, C$_{3-7}$ cycloalkyl, phenyl, or benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$;, with the proviso that R"" may also be hydrogen; each α-aminoacyl group is independently selected from racemic, D, or L-amino acids; Y$_1$ is hydrogen, C$_{1-6}$ alkyl, or benzyl; Y$_0$ is C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, or di-N,N-C$_{1-6}$ alkylaminoC$_{1-4}$ alkylenyl; and Y$_2$ is mono-N—C$_{1-6}$ alkylamino, di-N,N-C$_{1-6}$ alkylamino, morpholin-4-yl, piperidin-1-yl, pyrrolidin-1-yl, or 4-C$_{1-4}$ alkylpiperazin-1-yl. Particularly useful compounds of Formula VII are amides derived from carboxylic acids containing one to ten carbon atoms, amides derived from amino acids, and carbamates containing one to ten carbon atoms. The reaction can be carried out, for example, by combining a compound of Formula Ia with a chloroformate or acid chloride, such as ethyl chloroformate or acetyl chloride, in the presence of a base such as triethylamine in a suitable solvent such as dichloromethane at room temperature.

Compounds of the invention can also be prepared using variations of the synthetic routes shown in Reaction Schemes I through X that would be apparent to one of skill in the art. For example, the order of steps may be changed in Reaction Schemes II, III, and VI through IX to prepare compounds of the invention. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m² to about 5.0 mg/m², computed according to the Dubois method, in which the body surface area of a subject (m²) is computed using the subject's body weight: $m^2 = (wt\ kg^{0.425} \times height\ cm^{0.725}) \times 0.007184$, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal.

An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Preparation of 2-Chloromethyl-1-(2-methylpropyl)-1H-imidazo[4,5-c]quinolin-4-amine Part A N$^4$-(2-Methylpropyl)quinoline-3,4-diamine (U.S. Pat. No. 5,389,640 Example 1, 41 g, 0.190 mol), dichloromethane (550 mL), triethylamine (40 mL, 0.286 mol), and chloroacetyl chloride (16.7 mL, 0.210 mol) were combined and then stirred at ambient temperature over the weekend. The reaction mixture was diluted with 1,2-dichloroethane (75 mL) and then washed with saturated aqueous sodium bicarbonate (3×400 mL). The organic layer was dried over magnesium sulfate, filtered through a layer of CELITE filter aid, and then concentrated under reduced pressure to provide 52.81 g of 2-chloromethyl-1-(2-methylpropyl)-1H-imidazo[4,5-c] quinoline as a brown solid.

Part B

3-Chloroperoxybenzoic acid (mCPBA) (32.7 g of 77% pure material, 146 mmol) was added over a period of five minutes to a solution of 2-chloromethyl-1-(2-methylpropyl)-1H-imidazo[4,5-c]quinoline (20.0 g, 73.1 mmol) in chloroform (500 mL); the reaction mixture was stirred at ambient temperature for one hour. Ammonium hydroxide (200 mL) was added, and then p-toluenesulfonyl chloride (16.7 g, 87.7 mmol) was added in portions over a period of 10 minutes. The reaction mixture was stirred at ambient temperature for one hour, and then water (200 mL) was added. The aqueous layer was separated and extracted with dichloromethane (2×200 mL). The combined organic fractions were dried over magnesium sulfate, filtered, and concentrated under reduced pressure to provide 32 g of crude product as a tan solid. The crude product was dissolved in dichloromethane (50 mL), and the resulting solution was divided into two portions. Each portion was purified by column chromatography using a HORIZON HPFC system (an automated, modular high-performance flash purification product available from Biotage, Inc, Charlottesville, Va., USA) using a FLASH 65I silica cartridge (also available from Biotage, Inc.) (eluting with ethyl acetate:methanol in a gradient from 98:2 to 85:15) to provide 11.24 g of 2-chloromethyl-1-(2-methylpropyl)-1H-imidazo[4,5-c]quinolin-4-amine as a tan solid.

Example 1

1-(2-Methylpropyl)-2-{[methoxy(methyl)amino]methyl}-1H-imidazo[4,5-c]quinolin-4-amine

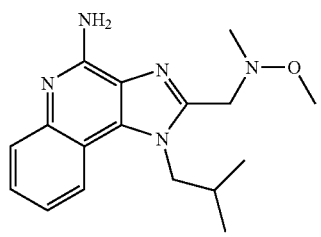

2-Chloromethyl-1-(2-methylpropyl)-1H-imidazo[4,5-c]quinolin-4-amine (0.100 g, 0.346 mmol) and triethylamine (0.105 g, 1.04 mmol) were added to a solution of N,O-dimethylhydroxylamine hydrochloride (0.068 g, 0.69 mmol) in. N,N-dimethylformamide (DMF) (2 mL). A precipitate formed after the addition of triethylamine. The reaction was heated with stirring for three days at 50° C., allowed to cool to ambient temperature, and partitioned between ethyl acetate (5 mL) and water (5 mL). The organic fraction was concentrated under reduced pressure to afford a white solid, which was purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase prep HPLC was performed with non-linear gradient elution from 5-95% B where A is 0.05% trifluoroacetic acid/water and B is 0.05% trifluoroacetic acid/acetonitrile. Fractions were collected by mass-selective triggering. The prep HPLC purification afforded 1-(2-methylpropyl)-2-{[methoxy(methyl)amino]methyl}-1H-imidazo[4,5-c]quinolin-4-amine trifluoroacetate.

HRMS (ESI) m/z 314.1974 (M+H).

Example 2

1-(2-Methylpropyl)-2-[(methoxyamino)methyl]-1H-imidazo[4,5-c]quinolin-4-amine

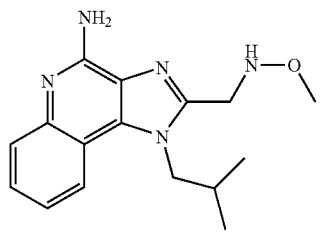

Methoxylamine hydrochloride (145 mg, 1.73 mmol) was added to a solution of 2-chloromethyl-1-(2-methylpropyl)-1H-imidazo[4,5-c]quinolin-4-amine (0.250 g, 0.866 mmol) in DMF (3 mL). A precipitate formed. Triethylamine (0.263 g, 2.60 mmol) was added, and the reaction was heated with stirring overnight at 50° C., allowed to cool to ambient temperature, and partitioned between ethyl acetate (5 mL) and water (5 mL). The aqueous fraction was extracted twice with ethyl acetate, and the combined organic fractions were dried over magnesium sulfate, filtered, and concentrated under reduced pressure. The crude product was purified by radial chromatography on a silica gel plate (2 mm) (eluting sequentially with 2% and 5% methanol in chloroform). The solid was then purified by prep HPLC as described in Example 1 to provide 1-(2-methylpropyl)-2-[(methoxyamino)methyl]-1H-imidazo[4,5-c]quinolin-4-amine trifluoroacetate.

HRMS (ESI) m/z 300.1839 (M+H).

Example 3

2-{[Hydroxy(methyl)amino]methyl}-1-(2-methylpropyl)-1H-imidazo[4,5-c]quinolin-4-amine

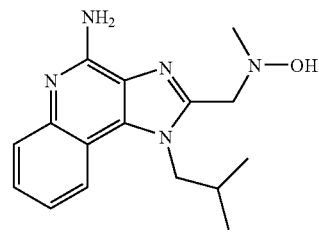

The method described in Example 1 was followed using N-methylhydroxylamine hydrochloride (0.058 g, 0.69 mmol) in lieu of N,O-dimethylhydroxylamine hydrochloride. The product was purified by prep HPLC as described in Example 1 to provide 2-{[hydroxy(methyl)amino]methyl}-1-(2-methylpropyl)-1H-imidazo[4,5-c]quinolin-amine trifluoroacetate.

HRMS (ESI) m/z 300.1826 (M+H).

Example 4

4-Amino-1-(2-methylpropyl)-1H-imidazo[4,5-c]quinoline-2-carbaldehyde O-methyloxime

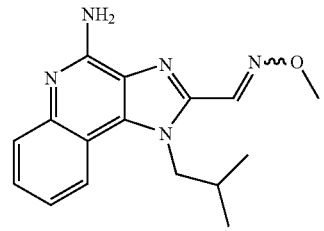

Part A

A solution of 1-(2-methylpropyl)-1H-imidazo[4,5-c]quinoline (U.S. Pat. No. 5,175,296 Example 1 Part C, 25.64 g, 113.8 mmol) in tetrahydrofuran (THF) (450 mL) was cooled to −78° C. Butyllithium (45.5 mL of a 2.5 M solution in hexanes) was added dropwise over a period of ten minutes, and the resulting solution was stirred for ten minutes. DMF (20.1 mL, 274.4 mmol) was added, and the reaction was allowed to warm to room temperature and stirred for one hour. The THF was then removed under reduced pressure, and the residue was dissolved in ethyl acetate (400 mL). The resulting solution was washed with brine (400 mL), dried over magnesium sulfate, filtered, and concentrated under reduced pressure. The crude product was purified by column chromatography on silica gel (eluting sequentially with 0.5% and 1% methanol in dichloromethane) to provide 10.5 g of 1-(2-methylpropyl)-1H-imidazo[4,5-c]quinoline-2-carbaldehyde as a light brown solid.

Part B

Methoxylamine hydrochloride (0.659 g, 7.90 mmol) was added to a stirred suspension of 1-(2-methylpropyl)-1H-imidazo[4,5-c]quinoline-2-carbaldehyde (1.00 g, 3.95 mmol) in methanol (10 mL), and the reaction was stirred at room temperature overnight. The methanol was removed under reduced pressure, and the residue was diluted with saturated aqueous sodium bicarbonate (50 mL). The resulting mixture was extracted with dichloromethane (3×30 mL), and the combined extracts were dried over magnesium sulfate, filtered, and concentrated under reduced pressure to provide 1.16 g of 1-(2-methylpropyl)-1H-imidazo[4,5-c]quinoline-2-carbaldehyde O-methyloxime as a pale yellow oil that solidified upon standing.

Part C mCPBA (1.75 g of 77% pure material, 7.79 mmol) was added in portions over a period of five minutes to a solution of 1-(2-methylpropyl)-1H-imidazo[4,5-c]quinoline-2-carbaldehyde O-methyloxime (1.1 g, 3.9 mmol) in chloroform (40 mL), and the reaction was stirred at room temperature for one hour. Ammonium hydroxide (20 mL) was added, and the resulting mixture was stirred for five minutes before the addition of p-toluenesulfonyl chloride (0.891 g, 4.68 mmol) in portions. The reaction mixture was stirred at room temperature for 1.5 hours. The aqueous layer was then separated and extracted with dichloromethane (3×30 mL). The combined organic fractions were dried over magnesium sulfate, filtered, and concentrated under reduced pressure to provide 2.2 g of crude product as a brown foamy solid. The crude product was dissolved in dichloromethane (15 mL) and purified by chromatography using a HORIZON HPFC system (FLASH 40M silica cartridge available from Biotage, Inc., eluting with 2% to 7% methanol in ethyl acetate). The resulting product (580 mg) was recrystallized from acetonitrile (10 mL), and the crystals were isolated by filtration, washed with diethyl ether, and dried overnight in a vacuum oven at 65° C. to provide 236 mg of 4-amino-1-(2-methylpropyl)-1H-imidazo[4,5-c]quinoline-2-carbaldehyde O-methyloxime as a brown solid, mp 181-183° C.

Anal. Calcd for $C_{16}H_{19}N_5O$: C, 64.63; H, 6.44; N, 23.55. Found: C, 64.37; H, 6.39; N, 23.57.

Example 5

4-[4-Amino-1-(2-hydroxy-2-methylpropyl)-1H-imidazo[4,5-c]quinolin-2-yl]butan-2-one O-methyloxime

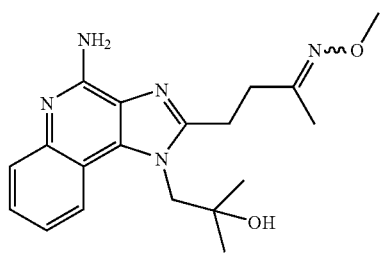

Part A

A mixture of ethyl levulinate (58.35 g, 400.0 mmol), ethylene glycol (75.36 g, 1.21 mol), pyridinium p-toluenesulfonate (100 mg) and toluene (200 mL) was heated at reflux under a Dean Stark trap. The trap was emptied every 15 minutes during the reaction until approximately 200 mL of reaction volatiles had been removed. The remaining toluene was removed under reduced pressure, and the resulting oil was partitioned between ethyl acetate (200 mL) and water (50 mL). The organic layer was separated and washed sequentially with water (2×50 mL), saturated aqueous sodium bicarbonate (50 mL), and brine (50 mL); dried over sodium sulfate, filtered, and concentrated under reduced pressure to provide 68.9 g of ethyl 3-(2-methyl-1,3-dioxolan-2-yl)propanoate as a light yellow oil.

Part B

A solution of ethyl 3-(2-methyl-1,3-dioxolan-2-yl)propanoate (68.9 g, 366 mmol) in methanol (73 mL) was cooled to approximately 0° C. A warm solution of sodium hydroxide (14.63 g, 366 mmol) in water (73 mL) was added dropwise over a period of three hours. The reaction was then allowed to warm to room temperature and stirred for 17 hours. The methanol was removed under reduced pressure, and the resulting aqueous solution was diluted with water (400 mL) and washed with ethyl acetate (150 mL). The aqueous solution was then cooled to approximately 0° C. and adjusted to pH 2 with the addition of sulfuric acid (180 mL of 1 M). The resulting mixture was extracted with ethyl acetate (2×150 mL), and the combined extracts were washed with brine (50 mL), dried over sodium sulfate, filtered, and concentrated under reduced pressure to provide 38.6 g of 3-(2-methyl-1,3-dioxolan-2-yl)propanoic acid as a light yellow oil.

Part C

A solution of 3-(2-methyl-1,3-dioxolan-2-yl)propanoic acid (8.95 g, 55.9 mmol) in dichloromethane (111 mL) was cooled to approximately 0° C. N-hydroxysuccinimide (7.10 g, 61.5 mmol), 4-methylmorpholine (6.22 g, 61.5 mmol), and 1-(3-dimethylaminopropyl)-3-ethylcarbodiimide hydrochloride (11.8 g, 61.5 mmol) were sequentially added with stirring. The reaction was then allowed to warm to room temperature, stirred for 17 hours, and partitioned between dichloromethane (150 mL) and water (50 mL). The organic layer was separated; sequentially washed with water (50 mL), saturated aqueous sodium bicarbonate (2×50 μL), and brine (50 mL); dried over sodium sulfate; filtered; and concentrated under reduced pressure to provide 13 g of 1-{[3-(2-methyl-1,3-dioxolan-2-yl)propanoyl]oxy}pyrrolidine-2,5-dione as a white solid.

Part D

A solution of 3-amino-4-(2-hydroxy-2-methylpropylamino)quinoline (U.S. Pat. No. 5,389,640, 6.00 g, 26.0 mmol) and 1-{[3-(2-methyl-1,3-dioxolan-2-yl)propanoyl]oxy}pyrrolidine-2,5-dione (8.01 g, 31.1 mmol) in pyridine (130 mL) was heated at reflux under a Dean-Stark trap for seven hours, allowed to cool to room temperature, and stirred for 48 hours. The volatiles were removed under reduced pressure, and the residue was dissolved in dichloromethane (200 mL). The resulting solution was washed sequentially with saturated aqueous sodium bicarbonate (2×100 mL) and brine (100 mL), dried over sodium sulfate, filtered, and concentrated under reduced pressure. The resulting dark brown oil was purified by column chromatography on silica gel (eluting with dichloromethane and 5% methanol in dichloromethane) to provide 4.5 g of 2-methyl-1-{(2-[2-(2-methyl-1,3-dioxolan-2-yl)ethyl]-1H-imidazo[4,5-c]quinolin-1-yl}propan-2-ol.

Part E mCPBA (2.2 g of 60% pure material, 7.7 mmol) was added in portions over a period of five minutes to a stirred solution of 2-methyl-1-{2-[2-(2-methyl-1,3-dioxolan-2-yl)ethyl]-1H-imidazo[4,5-c]quinolin-1-yl}propan-2-ol (2.5 g, 7.0 mmol) in chloroform (47 mL), and the reaction was stirred at room temperature for 20 minutes. The reaction mixture was partitioned between dichloromethane (200 mL) and saturated aqueous sodium carbonate (100 mL). The organic layer was separated and washed with saturated aqueous sodium carbonate (100 mL). The combined aqueous fractions were extracted with dichloromethane (50 mL). The combined organic fractions were washed with brine (50 mL), dried over sodium sulfate, filtered, and concentrated under reduced pressure to provide 2-methyl-1-{2-[2-(2-methyl-1,3-dioxolan-2-yl)ethyl]-5-oxido-1H-imidazo[4,5-c]quinolin-1-yl}propan-2-ol as a tan solid.

Part F

Ammonium hydroxide (12 mL of 30%) was added to a stirred solution of the material from Part E in dichloromethane (35 mL). p-Toluenesulfonyl chloride (1.34 g, 7.03 mmol) was added in portions over a period of two minutes with vigorous stirring. The reaction mixture was stirred at room temperature for five hours. A solid was present and was isolated by filtration to provide 2.1 g of white powder, which was recrystallized from ethanol (145 mL). The crystals were isolated by filtration, washed with ethanol, and dried for four hours under vacuum at 65° C. to provide 1.7 g of 1-{4-amino-2-[2-(2-methyl-1,3-dioxolan-2-yl)ethyl]-1H-imidazo[4,5-c]quinolin-1-yl}-2-methylpropan-2-ol as a brown solid, mp 231-233° C.

Anal. Calcd for $C_{20}H_{26}N_4O_3$: C, 64.85; H, 7.07; N, 15.12. Found: C, 64.72; H, 7.40; N, 15.05.

Part G

Concentrated hydrochloric acid (0.98 mL) was added dropwise to a stirred suspension of 1-{4-amino-2-[2-(2-methyl-1,3-dioxolan-2-yl)ethyl]-1H-imidazo[4,5-c]quinolin-1-yl}-2-methylpropan-2-ol (1.45 g, 3.91 mmol) in water (26 mL), and the resulting solution was stirred at room temperature for two hours and then adjusted to pH 11 with the addition of aqueous sodium hydroxide (20% w/w). A precipitate formed, and the suspension was stirred for several minutes. The precipitate was isolated by filtration and washed with water to provide 1.2 g of 4-[4-amino-1-(2-hydroxy-2-methylpropyl)-1H-imidazo[4,5-c]quinolin-2-yl]butan-2-one as a white powder.

Part H

Methoxylamine hydrochloride (0.26 g, 3.1 mmol) was added to a stirred solution of 4-[4-amino-1-(2-hydroxy-2-methylpropyl)-1H-imidazo[4,5-c]quinolin-2-yl]butan-2-one (0.600 g, 1.84 mmol) in pyridine (9 mL), and the reaction was stirred at room temperature for 45 minutes. Water (50 mL) was added. The aqueous layer was separated, extracted with dichloromethane (2×50 mL), adjusted to pH 10 with the addition of saturated aqueous sodium carbonate, and extracted with dichloromethane (2×25 mL). The combined organic fractions were washed sequentially with saturated aqueous sodium bicarbonate (50 mL) and brine (50 mL), dried over sodium sulfate, filtered, and concentrated under reduced pressure. The resulting white powder was stirred with diethyl ether for one hour, isolated by filtration, and washed with diethyl ether. The resulting solid (0.45 g) was recrystallized from acetonitrile (20 mL), and the crystals were isolated by filtration, washed with acetonitrile, and dried for 15 hours under vacuum at 60° C. to provide 0.40 g of 4-[4-amino-1-(2-hydroxy-2-methylpropyl)-1H-imidazo[4,5-c]quinolin-2-yl]butan-2-one O-methyloxime as white needles, mp 182-184° C.

Anal. Calcd for $C_{19}H_{25}N_5O_2$: C, 64.20; H, 7.09; N, 19.70. Found: C, 63.97; H, 7.21; N, 19.84.

Example 6

7-(Benzyloxy)-2-[(methoxyamino)methyl]-1-(tetrahydro-2H-pyran-4-ylmethyl)-1H-imidazo[4,5-c]quinolin-4-amine

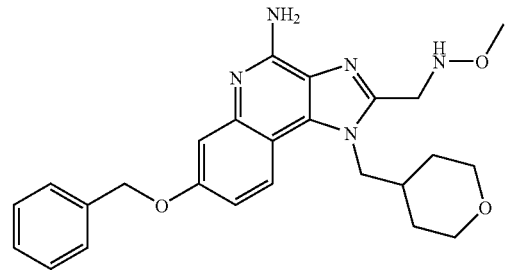

Part A 1-tetrahydro-2H-pyran-4-ylmethanamine (40 g, 0.347 mol) was added to a stirred solution of 7-(benzyloxy)-4-chloro-3-nitroquinoline (55 g, 0.176 mol) and triethylamine (50.96 g, 0.503 mol) in N,N-dimethylformamide (DMF) (250 mL) at 0° C. After complete addition, the ice bath was removed. To consume the remaining starting material, additional (1-tetrahydro-2H-pyran-4-ylmethanamine (11 g, 95.50 mmol) was added. The reaction proceeded at ambient temp for 3 days, then was chilled in an ice-water bath. Water (250 mL) was added drop wise which caused a solid to precipitate out of solution. After stirring for 1 hour, the solid was collected by filtration, washed with diethyl ether (800 mL), and dried under reduced pressure to afford 7-(benzyloxy)-3-nitro-N-(tetrahydro-2H-pyran-4-ylmethyl)quinolin-4-amine (59.3 g) as a bright yellow solid.

Part B

A 2 L glass parr vessel was charged with of 7-(benzyloxy)-3-nitro-N-(tetrahydro-2H-pyran-4-ylmethyl)quinolin-4-amine (59.34 g, 0.151 mol), platinum on carbon (5%, 6.6 g) and acetonitrile (600 mL) to provide a black mixture. The vessel was placed on a shaker and pressurized with hydrogen gas (~50 psi, 3.4×10⁵ Pa). After shaking for 18 hours at ambient temperature, the mixture was filtered through CELITE filter agent, and the filter cake washed with acetonitrile. The filtrate was concentrated under reduced pressure to provide 7-(benzyloxy)-N⁴-(tetrahydro-2H-pyran-4-ylmethyl)quinoline-3,4-diamine (51.2 g) as a viscous oil.

Part C

To a stirred solution of 7-(benzyloxy)-N⁴-(tetrahydro-2H-pyran-4-ylmethyl)quinoline-3,4-diamine (51.2 g, 0.141 mol) and triethylamine (39.94 g, 0.395 mol) in dichloromethane (410 mL) at 0° C. was added a solution of chloroacetyl chloride (8.67 g, 76.80 mmol) in dichloromethane (40 mL) drop wise by addition funnel. The reaction was stirred at ambient temperature for 17 hours then heated to reflux for 6 hours. The crude mixture was cooled to ambient temperature and partitioned between water and dichloromethane (200 mL). The layers were separated and the aqueous layer extracted with dichloromethane (2×300 mL). The organic layers were combined, washed with brine (2×300 mL), dried over magnesium sulfate, filtered and concentrated under reduced pressure to provide 7-(benzyloxy)-2-(chloromethyl)-1-(tetrahydro-2H-pyran-4-ylmethyl)-1H-imidazo[4,5-c]quinoline (61.7 g) as a brown solid.

Part D

3-Chloroperoxybenzoic acid (mCPBA) (1.4 g of 77% pure material, 4.74 mmol) was added over a period of five minutes to a solution of 7-(benzyloxy)-2-(chloromethyl)-1-(tetrahydro-2H-pyran-4-ylmethyl)-1H-imidazo[4,5-c]quinoline (2.0 g, 4.74 mmol) in chloroform (47 mL); the reaction mixture was stirred at ambient temperature for one hour. The reaction solution was partitioned between chloroform (50 mL) and saturated aqueous sodium carbonate (50 mL). The layers were separated and the aqueous layer extracted with chloroform (50 mL). The organic layers were combined, dried over sodium sulfate, filtered, and concentrated under reduced pressure to afford an oil. To the crude N-oxide dissolved in dichloromethane (24 mL) was added ammonium hydroxide (8 mL), and then p-toluenesulfonyl chloride (1.0 g, 3.11 mmol) was added in portions over a period of 2 minutes. The reaction mixture was stirred at ambient temperature for one hour, and then saturated aqueous sodium carbonate (50 mL) and chloroform (50 mL) were added. The aqueous layer was separated and extracted with chloroform (50 mL). The combined organic fractions were dried over sodium sulfate, filtered, and concentrated under reduced pressure to provide 2.1 g of crude product as a tan solid. The crude product was purified by column chromatography using a HORIZON HPFC system (an automated, modular high-performance flash purification product available from Biotage, Inc, Charlottesville, Va., USA) using a FLASH 40+M silica cartridge (also available from Biotage, Inc.) (eluting with dichloromethane:methanol in a gradient from 100:0 to 90:10) to provide 1.8 g of 7-(benzyloxy)-2-(chloromethyl)-1-(tetrahydro-2H-pyran-4-ylmethyl)-1H-imidazo[4,5-c]quinolin-4-amine as a tan solid.

Part E 7-(Benzyloxy)-2-(chloromethyl)-1-(tetrahydro-2H-pyran-4-ylmethyl)-1H-imidazo[4,5-c]quinolin-4-amine (2.3 g, 5.26 mmol) and triethylamine (1.6 g, 15.78 mmol) were added to a solution of methoxylamine hydrochloride (0.88 g, 10.52 mmol) in N,N-dimethylformamide (DMF) (11 mL). The reaction was heated with stirring for 40 hours at 50° C., allowed to cool to ambient temperature, and partitioned between dichloromethane (50 mL) and water (50 mL). The aqueous layer was extracted with another portion of dichloromethane (50 mL). The combined organic layers were dried over sodium sulfate and filtered and concentrated under reduced pressure. The crude material was purified by column chromatography using a HORIZON HPFC system equipped with a FLASH 40+M silica cartridge eluting with dichloromethane:methanol in a gradient from 100:0 to 90:10. The resulting product (1.0 g) was recrystallized from acetonitrile, and the crystals were isolated by filtration, washed with acetonitrile, and dried overnight in a vacuum oven at 65° C. to provide 0.85 g of 7-(benzyloxy)-2-[(methoxyamino)methyl]-1-(tetrahydro-2H-pyran-4-ylmethyl)-1H-imidazo[4,5-c]quinolin-4-amine as a yellow, crystalline solid, mp 190-193° C.

Anal. Calcd for $C_{25}H_{29}N_5O_3$: C, 67.09; H, 6.53; N, 15.65. Found: C, 66.88; H, 6.44; N, 15.55.

Example 7

7-(Benzyloxy)-2-{[methoxy(methyl)amino]methyl}-1-(tetrahydro-2H-pyran-4-ylmethyl)-1H-imidazo[4,5-c]quinolin-4-amine

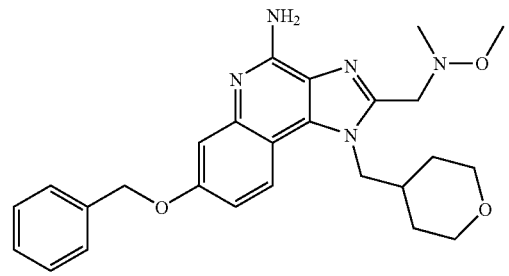

7-(Benzyloxy)-2-(chloromethyl)-1-(tetrahydro-2H-pyran-4-ylmethyl)-1H-imidazo[4,5-c]quinolin-4-amine (0.50 g, 1.14 mmol) and triethylamine (0.34 g, 3.42 mmol) were added to a solution of N, O-dimethylhydroxylamine hydrochloride (0.22 g, 2.29 mmol) in N)N-dimethylformamide (DMF) (2 mL). The resulting suspension was heated with stirring for 40 hours at 50° C., allowed to cool to ambient temperature, and partitioned between dichloromethane (30 mL) and water (20 mL). The aqueous layer was extracted with another portion of dichloromethane (30 mL). The combined organic layers were dried over sodium sulfate, filtered and concentrated under reduced pressure. The crude material was purified by column chromatography using a HORIZON HPFC system equipped with a FLASH 40+M silica cartridge eluting with dichloromethane:methanol in a gradient from 100:0 to 90:10. The resulting product (0.3 g) was recrystallized from acetonitrile (3 mL), and the crystals were isolated by filtration, washed with acetonitrile, and dried overnight in a vacuum oven at 65° C. to provide 0.14 g of 7-(benzyloxy)-2-{[methoxy(methyl)amino]methyl}-1-(tetrahydro-2H-pyran-4-ylmethyl)-1H-imidazo[4,5-c]quinolin-4-amine as a yellow, crystalline solid, mp 159-161° C.

Anal. Calcd for $C_{26}H_{31}N_5O_3 \cdot H_2O_{1/4}$: C, 67.00; H, 6.81; N, 15.03. Found: C, 66.91; H, 6.95; N, 15.08.

Example 8

N-{[4-Amino-7-(benzyloxy)-1-(tetrahydro-2H-pyran-4-ylmethyl)-1H-imidazo[4,5-c]quinolin-2-yl]methyl}-N-methoxymethanesulfonamide

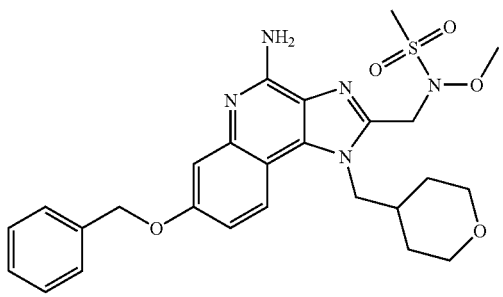

To a solution of 7-(benzyloxy)-2-(chloromethyl)-1-(tetrahydro-2H-pyran-4-ylmethyl)-1H-imidazo[4,5-c]quinolin-4-amine (0.70 g, 1.56 mmol) and triethylamine (0.30 g, 3.12 mmol) in dichloromethane (6 mL) was added methanesulfonyl chloride (0.20 g, 1.72 mmol) dropwise. The brown solution was stirred at ambient temperature for 18 hours, and then concentrated under reduced pressure. The crude material was purified by column chromatography using a HORIZON HPFC system equipped with a FLASH 25+M silica cartridge eluting with dichloromethane:methanol in a gradient from 100:0 to 90:10. The resulting product (0.35 g) was recrystallized from acetonitrile (43 mL), and the crystals were isolated by filtration, washed with acetonitrile, and dried overnight in a vacuum oven at 65° C. to provide 0.19 g of N-{[4-amino-7-(benzyloxy)-1-(tetrahydro-2H-pyran-4-ylmethyl)-1H-imidazo[4,5-c]quinolin-2-yl]methyl}-N-methoxymethanesulfonamide as a yellow, crystalline solid, mp 195-197° C.

Anal. Calcd for $C_{26}H_{31}N_5O_5S$: C, 59.41; H, 5.94; N, 13.32. Found: C, 59.78; H, 5.80; N, 13.61.

Example 9

1-Isobutyl-2-[(methoxyamino)methyl]-6,7-dimethyl-1H-imidazo[4,5-c]pyridin-4-amine

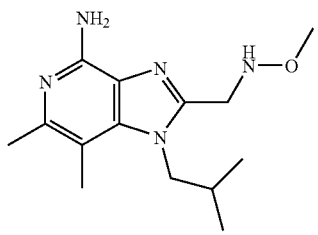

Part A

A solution of 2,4-dichloro-5,6-dimethyl-3-nitropyridine (40.0 g, 181 mmol), triethylamine (26.5 mL, 190 mmol), and isobutyl amine (18.9 mL, 190 mmol) in N,N-dimethylformamide (500 mL) was stirred at room temperature over night. The solvent was removed under reduced pressure. The residue was dissolved in ethyl acetate (500 mL) and washed with water (3×80 mL) and brine (40 mL). The aqueous was extracted with ethyl acetate (3×50 mL) and the back-extracts washed with water (3×40 mL) and brine (30 mL). The combined organics were dried over magnesium sulfate, filtered, and concentrated under reduced pressure. The crude product was purified by HPFC eluting with a gradient of 10-30% ethyl acetate in hexanes to give 25.8 g of 2-chloro-N-isobutyl-5,6-dimethyl-3-nitropyridin-4-amine as a yellow oil.

Part B

2-Chloro-N-isobutyl-5,6-dimethyl-3-nitropyridin-4-amine (25.8 g, 100 mmol) was combined with 5% platinum on carbon (2.58 g) and ethyl acetate (200 mL) in a pressure vessel and hydrogenated at 50 psi (3.4×10⁵ Pa) for 2.5 hours on a Parr apparatus. The reaction mixture was filtered through CELITE filter agent, which was rinsed with ethyl acetate and methanol afterwards. The filtrate was concentrated to give 2-chloro-$N^4$-isobutyl-5,6-dimethylpyridine-3,4-diamine and was used directly in the next step.

Part C

Under a nitrogen atmosphere, the material from part B was dissolved in dichloromethane (400 mL) and cooled to 0° C. Ethoxyacetyl chloride (14.7 g, 120 mmol) dissolved in dichloromethane (100 mL) was added dropwise through an addition funnel and the solution was stirred at room temperature over night. The solvent was removed under reduced pressure and the white solid used directly in the next step.

Part D

The material from part C was suspended in ethanol (500 mL), and sodium hydroxide (10.0 g, 250 mmol) was added. The mixture was heated to reflux under a nitrogen atmosphere for four hours. The heat was removed and the solution allowed to stir at room temperature over night. The solvent was removed under reduced pressure and the residue dissolved in dichloromethane (500 mL), washed with water (100 mL) and brine (60 mL), dried over sodium sulfate, filtered and concentrated under reduced pressure to give 29.6 g of 4-chloro-2-(ethoxymethyl)-1-isobutyl-6,7-dimethyl-1H-imidazo[4,5-c]pyridine as a yellow oil.

Part E

A 500 mL round bottom flask was charged with 4-chloro-2-(ethoxymethyl)-1-isobutyl-6,7-dimethyl-1H-imidazo[4,5-c]pyridine (10.0 g, 33.8 mmol) and dichloromethane (250 mL) under a nitrogen atmosphere. The solution was cooled to 0° C. and boron tribromide (101 mL of 1M in dichloromethane, 101 mmol) was added through an addition funnel over 30 minutes. The reaction mixture was allowed to warm to room temperature and was stirred over night. Methanol was added slowly until no more fizzing occurred, then the solvent was partially removed under reduced pressure. More methanol was added (100 mL) as well as 6N hydrochloric acid (100 mL) and the solution was heated at reflux for 1 hour. The reaction mixture was then allowed to cool to room temperature and stirred over night. The solvent was partially removed under reduced pressure until a solid precipitated, which was isolated by filtration and washed with water, then triturated with ethyl acetate and hexanes to give 6.15 g of (4-chloro-1-isobutyl-6,7-dimethyl-1H-imidazo[4,5-c]pyridin-2-yl)methanol as an off-white solid.

Part F

A solution of 4-chloro-1-isobutyl-6,7-dimethyl-1H-imidazo[4,5-c]pyridin-2-yl)methanol (1.50 g, 5.60 mmol), 4-methoxybenzylamine (3.66 mL, 28 mmol) and pyridine hydrochloride (1.74 g, 11.2 mmol) in 2,2,2-trifluoroethanol (11.2 mL) was heated to 150° C. in a microwave oven for 2.5 hours. The mixture was allowed to cool to room temperature, then poured into water (75 mL) and stirred for 30 minutes. The precipitate was isolated by filtration and washed with water to give 1.86 g of {1-isobutyl-4-[(4-methoxybenzyl)amino]-6,7-dimethyl-1H-imidazo[4,5-c]pyridin-2-yl}methanol.

Part G

{1-Isobutyl-4-[(4-methoxybenzyl)amino]-6,7-dimethyl-1H-imidazo[4,5-c]pyridin-2-yl}methanol (3.08 g, 8.36 mmol) was dissolved in trifluoroacetic acid (31 mL) and stirred at room temperature over night. The solvent was removed under reduced pressure and concentrated hydrochloric acid (5 mL) was added. The suspension was stirred for 2 hours, the solid was isolated by filtration and washed with water to give 1.95 g of (4-amino-1-isobutyl-6,7-dimethyl-1H-imidazo[4,5-c]pyridin-2-yl)methanol as a tan powder.

Part H

A solution of (4-amino-1-isobutyl-6,7-dimethyl-1H-imidazo[4,5-c]pyridin-2-yl)methanol (1.95 g, 7.85 mmol) and thionyl chloride (1.72 mL, 23.6 mmol) in chloroform (80 mL) was heated at reflux for 2 hours. The solvent was removed under reduced pressure and the residue triturated with chloroform to give 1.53 g of 2-(chloromethyl)-1-isobutyl-6,7-dimethyl-1H-imidazo[4,5-c]pyridin-4-amine hydrochloride as an off-white powder.

Part I 2-(chloromethyl)-1-isobutyl-6,7-dimethyl-1H-imidazo[4,5-c]pyridin-4-amine hydrochloride (1.53 g, 5.05 mmol) was dissolved in 10 mL of DMF in a pressure tube under a nitrogen atmosphere. Methoxylamine hydrochloride (1.27 g, 15.15 mmol) and triethylamine (4.22 mL, 30.3 mmol) were added, the tube was sealed and the contents heated to 50° C. for two hours, then to 60° C. for five hours. The mixture was then stored in the refrigerator over the weekend. The contents were poured into water (60 mL) and stirred for 20 minutes. The solution was extracted with chloroform (3×70 mL) and the organics were washed with water (4×40 mL) and brine (30 mL), dried over sodium sulfate, filtered and concentrated under reduced pressure. The crude product was purified by HPFC eluting with a gradient of 0-30% CMA (80/18/2 v/v/v chloroform/methanol/concentrated ammonium hydroxide) in chloroform and then recrystallized from acetonitrile to provide 1-isobutyl-2-[(methoxyamino)methyl]-6,7-dimethyl-1H-imidazo[4,5-c]pyridin-4-amine as a white powder, mp 154.0-156.0° C.

Anal. Calcd for $C_{14}H_{23}N_5O$ C, 60.62; H, 8.36; N, 25.25. Found: C, 60.63; H, 8.33; N, 25.35.

Example 10

1-Isobutyl-2-{[methoxy(methyl)amino]methyl}-6,7-dimethyl-1H-imidazo[4,5-c]pyridin-4-amine

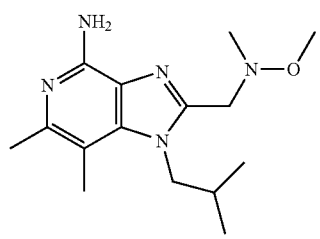

1-Isobutyl-2-{[methoxy(methyl)amino]methyl}-6,7-dimethyl-1H-imidazo[4,5-c]pyridin-4-amine was prepared and purified according to the general methods of Example 9 using N,O-dimethyl hydroxylamine hydrochloride in lieu of methoxylamine hydrochloride in Part I. The pure product was obtained as a white powder, mp 132.0-134.0° C. Anal. Calcd for $C_{15}H_{25}N_5O$ C., 61.83; H, 8.65; N, 24.03. Found: C, 61.63; H, 8.88; N, 24.02.

Example 11

N-[(4-Amino-1-isobutyl-6,7-dimethyl-1H-imidazo[4,5-c]pyridin-2-yl)methyl]-N-methoxycyclopropanecarboxamide

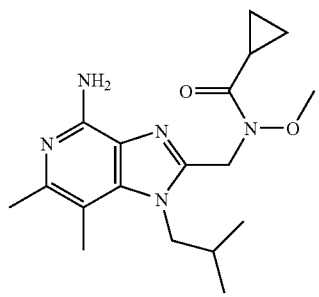

Under a nitrogen atmosphere, 1-isobutyl-2-[(methoxyamino)methyl]-6,7-dimethyl-1H-imidazo[4,5-c]pyridin-4-amine (0.53 g, 1.91 mmol) was dissolved in dichloromethane (19 mL) and cooled to −5° C. Triethylamine (293 uL, 2.10 mmol) was added followed by dropwise addition of cyclopropane carbonyl chloride (173 uL, 1.91 mmol). The solution was allowed to stir at RT for 2 hours, then cooled back to −5° C. More triethylamine (38 uL, 0.27 mmol) and cyclopropane carbonyl chloride (23 uL, 0.25 mmol) were added and the reaction was allowed to stir at 0° C. for 45 minutes. More cyclopropane carbonyl chloride (5 uL, 0.06 mmol) was added and stirring continued for another 30 minutes. Dichloromethane (100 mL) was added and the solution was washed successively with saturated aqueous sodium bicarbonate (30 mL), water (3×25 mL), and brine (20 mL), dried over sodium sulfate, filtered and concentrated under reduced pressure. The crude product was purified by HPFC eluting with a gradient of 0-35% CMA in chloroform and then recrystallized from ethyl acetate/hexanes to provide 292 mg of pure product as an off-white powder, mp 135.0-137.0° C. Anal. Calcd for $C_{18}H_{27}N_5O_2$ C, 62.59; H, 7.88; N, 20.27. Found: C, 62.68; H, 7.82; N, 19.93.

Example 12

1-({4-Amino-2-[(methoxyamino)methyl]-1H-imidazo[4,5-c]quinolin-1-yl}methyl)cyclobutanol

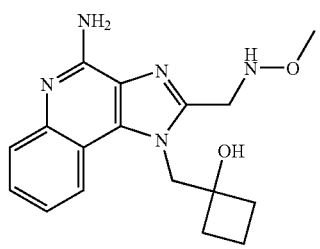

1-({4-Amino-2-[(methoxyamino)methyl]-1H-imidazo[4,5-c]quinolin-1-yl}methyl)cyclobutanol was prepared according to the general methods of Part I of Example 9 using 1-{[4-amino-2-(chloromethyl)-1H-imidazo[4,5-c]quinolin-1-yl]methyl}cyclobutanol in lieu of 2-(chloromethyl)-1-isobutyl-6,7-dimethyl-1H-imidazo[4,5-c]pyridin-4-amine hydrochloride. The crude product was purified by HPFC eluting with a gradient of 0-35% CMA in chloroform and then recrystallized from acetonitrile to provide pure product as a white powder, mp 178.0-181.0° C. Anal. Calcd for $C_{17}H_{21}N_5O_2$ C, 62.37; H, 6.47; N, 21.39. Found: C, 62.35; H, 6.51; N, 21.26.

Example 13

1-[(4-Amino-2-{[methoxy(methyl)amino]methyl}-1H-imidazo[4,5-c]quinolin-1-yl)methyl]cyclobutanol

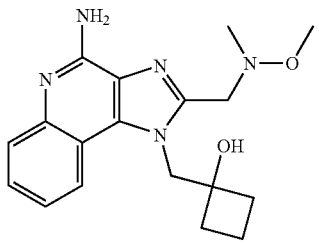

1-[(4-Amino-2-{[methoxy(methyl)amino]methyl}-1H-imidazo[4,5-c]quinolin-1-yl)methyl]cyclobutanol was prepared according to the general methods of Part I of Example 9 using N,O-dimethyl hydroxylamine hydrochloride in lieu of methoxylamine hydrochloride and using 1-{[4-amino-2-(chloromethyl)-1H-imidazo[4,5-c]quinolin-1-yl]methyl}cyclobutanol in lieu of 2-(chloromethyl)-1-isobutyl-6,7-dimethyl-1H-imidazo[4,5-c]pyridin-4-amine hydrochloride. The crude product was purified by HPFC eluting with a gradient of 0-35% CMA in chloroform and then recrystallized from acetonitrile to provide pure product as a white powder, mp 219.0-221.0° C. Anal. Calcd for $C_{18}H_{23}N_5O_2$ C, 63.32; H, 6.79; N, 20.51. Found: C, 63.12; H, 6.56; N, 20.16.

Example 14

4-Amino-1-isobutyl-6,7-dimethyl-1H-imidazo[4,5-c]pyridine-2-carbaldehyde O-methyloxime

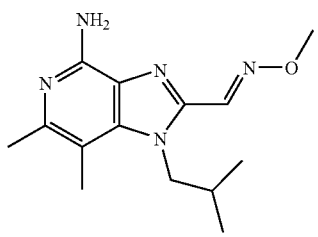

Part A

Under a nitrogen atmosphere {1-isobutyl-4-[(4-methoxybenzyl)amino]-6,7-dimethyl-1H-imidazo[4,5-c]pyridin-2-yl}methanol (2.00 g, 5.43 mmol, prepared as in Parts A-F of Example 9) was dissolved in dichloromethane (20 mL) and dimethylsulfoxide (10 mL). Triethylamine (2.27 mL, 16.3 mmol) was added and the solution was cooled to 0° C. Sulfur trioxide pyridine complex (2.60 g, 16.3 mmol) was then added in four portions and the solution was stirred at 0° C. for another 2 hours. The solution was then poured into saturated aqueous ammonium chloride (70 mL) and extracted with diethyl ether (3×80 mL). The organics were washed with water (2×30 mL) and brine (20 mL), dried over magnesium sulfate, filtered, and concentrated under reduced pressure to give 1.84 g of 1-isobutyl-4-[(4-methoxybenzyl)amino]-6,7-dimethyl-1H-imidazo[4,5-c]pyridine-2-carbaldehyde as a yellow residue.

Part B

The material from part A was dissolved in methanol (50 mL), and methoxylamine hydrochloride (0.63 g, 7.53 mmol) was added. Sodium hydroxide (1.42 mL of a 6N solution, 8.54 mmol) was added dropwise and the solution was stirred at room temperature overnight. Water (40 mL) was added and the solution was extracted with chloroform (3×80 mL). The organics were washed with saturated aqueous sodium bicarbonate (2×40 mL) and brine (30 mL), dried over magnesium sulfate, filtered, and concentrated under reduced pressure to give 1.90 g of 1-isobutyl-4-[(4-methoxybenzyl)amino]-6,7-dimethyl-1H-imidazo[4,5-c]pyridine-2-carbaldehyde O-methyloxime as a yellow oil.

Part C

1-Isobutyl-4-[(4-methoxybenzyl)amino]-6,7-dimethyl-1H-imidazo[4,5-c]pyridine-2-carbaldehyde O-methyloxime (1.60 g, 4.05 mmol) was dissolved in trifluoroacetic acid (16 mL) and stirred at room temperature over night. The solvent was removed under reduced pressure and concentrated hydrochloric acid (5 mL) was added, The suspension was stirred for 2 hours, then dichloromethane was added (10 mL) and the solution was cooled to 0° C. Sodium hydroxide (6N) was added until the solution was basic. More water (20 mL) was added and the solution was extracted with dichloromethane (2×100 mL). The organics were washed with brine (30 mL), dried over magnesium sulfate, filtered, and concentrated under reduced pressure. The crude product was purified by HPFC eluting with a gradient of 0-30% CMA in chloroform and then recrystallized from dichloromethane/hexanes. The solid was triturated with 1N sodium hydroxide to provide 256 mg of pure product as a white powder, mp 179.0-181.0° C. Anal. Calcd for $C_{14}H_{21}N_5O$ C, 61.07; H, 7.69; N, 25.43. Found: C, 61.16; H, 7.64; N, 25.69.

Example 15

1-(2-Hydroxy-2-methylpropyl)-2-{[methoxy(methyl)amino]methyl}-1H-imidazo[4,5-c]quinolin-4-amine

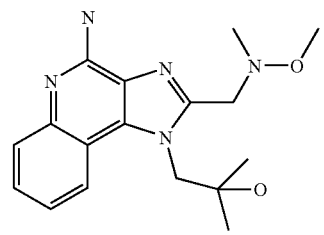

Triethylamine (0.747 g, 1.03 mL, 7.38 mmol) and N,O-dimethylhydroxylamine hydrochloride (0.480 g, 4.92 mmol) were added to a stirring suspension of 2-chloromethyl-1-(2-hydroxy-2-methylpropyl)-1H-imidazo[4,5-c]quinolin-4- amine (0.750 g, 2.46 mmol) in DMF (5 mL). The resulting suspension was heated to 50° C. and stirred for 17 hours. The reaction mixture was cooled to room temperature and poured into water (100 mL). A solid was removed by filtration and discarded. The filtrate was extracted with ethyl acetate (3×100 mL). The combined organic fractions were dried over magnesium sulfate, filtered and concentrated under reduced pressure. The residue was purified by column chromatography using a HORIZON HPFC system (silica cartridge, eluting with 5-20% methanol in dichloromethane). The resulting oil was crystallized from dichloromethane and isolated by filtration to yield 132 mg of 1-(2-Hydroxy-2-methylpropyl)-2-{[methoxy(methyl)amino]methyl}-1H-iidazo[4,5-c]quinolin-4-amine as a white solid, mp 220-222° C.

Anal. calcd for $C_{17}H_{23}N_5O_2$: C, 61.99; H, 7.04; N, 21.26. Found: C, 61.97; H, 7.10; N, 21.38.

Example 16

1-(2-Hydroxy-2-methylpropyl)-2-{[methoxylamino]methyl}-1H-imidazo[4,5-c]quinolin-4-amine; hydrochloride

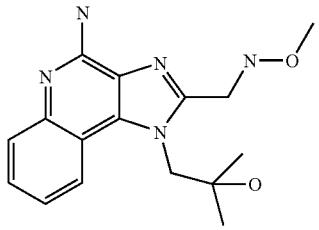

Triethylamine (1.49 g, 2.1 mL, 14.8 mmol) and methoxylamine hydrochloride (0.822 g, 9.84 mmol) were added to a stirring suspension of 2-chloromethyl-1-(2-hydroxy-2-methylpropyl)-1H-imidazo[4,5-c]quinolin-4-amine (1.50 g, 4.92 mmol) in DMF (10 mL). The resulting suspension was heated to 50° C. and stirred for 17 hours. The reaction mixture was cooled to room temperature and poured into water (20 mL). The aqueous layer was extracted with ethyl acetate (3×50 mL) and dichloromethane (3×50 mL). A significant amount of the desired product remained in the aqueous layer thus the organic fractions were combined with the aqueous fraction and concentrated under reduced pressure. The residue was purified by column chromatography using a HORIZON HPFC system (silica cartridge, eluting with 10-25% methanol in dichloromethane) and triturated with dichloromethane to provide 760 mg of 1-(2-Hydroxy-2-methylpropyl)-2-{[methoxylamino]methyl}-1H-imidazo[4,5-c]quinolin-4-amine; hydrochloride as a tan solid, mp 255-257° C.

Anal. calcd for $C_{16}H_{21}N_5O_2 \cdot HCl \cdot 0.5H_2O$: C, 53.26; H, 6.42; N, 19.41. Found: C, 53.57; H, 6.43; N, 19.34.

Example 17

2-[(Methoxyamino)methyl]-1-(tetrahydro-2H-pyran-4-ylmethyl)-1H-imidazo[4,5-c]quinoline

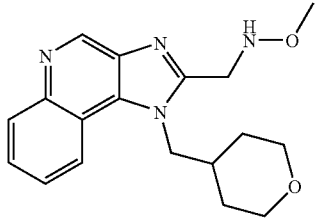

2-(Chloromethyl)-1-(tetrahydro-2H-pyran-4-ylmethyl)-1H-imidazo[4,5-c]quinoline (prepared according to the method described in parts A-C of Example 6 using 4-chloro-3-nitroquinoline in lieu of 7-(benzyloxy)-4-chloro-3-nitroquinoline) was converted to 2-[(methoxyamino)methyl]-1-(tetrahydro-2H-pyran-4-ylmethyl)-1H-imidazo[4,5-c]quinoline using the method detailed in part E of Example 6. The product was provided as 0.11 g of a light yellow glass, Mp 58-63° C.

Anal. calcd for $C_{18}H_{22}N_4O_2$: C, 66.24; H, 6.79; N, 17.17. Found: C, 66.19; H, 6.60; N, 17.06.

Example 18

2-{[Methoxy(methyl)amino]methyl}-1-(tetrahydro-2H-pyran-4-ylmethyl)-1H-imidazo[4,5-c]quinoline

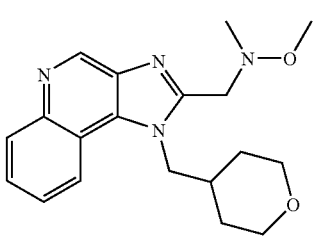

2-(Chloromethyl)-1-(tetrahydro-2H-pyran-4-ylmethyl)-1H-imidazo[4,5-c]quinoline (prepared according to the method described in parts A-C of Example 6 using 4-chloro-3-nitroquinoline in lieu of 7-(benzyloxy)-4-chloro-3-nitroquinoline) was converted 2-{[methoxy(methyl)amino]methyl}-1-(tetrahydro-2H-pyran-4-ylmethyl)-1H-imidazo[4,5-c]quinoline using the method detailed in Example 7. The product was provided as 0.09 g of a white solid, mp 142-144° C.

Anal. calcd for $C_{19}H_{24}N_4O_2$: C, 67.04; H, 7.11; N, 16.46. Found: C, 67.16; H, 7.17; N, 16.49.

Example 19

2-[(Methoxyamino)methyl]-1-(tetrahydro-2H-pyran-4-ylmethyl)-1H-imidazo[4,5-c]quinolin-4-amine

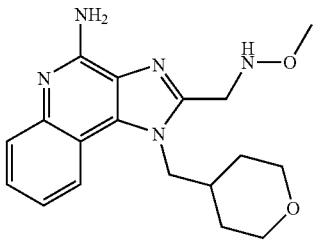

2-[(Methoxyamino)methyl]-1-(tetrahydro-2H-pyran-4-ylmethyl)-1H-imidazo[4,5-c]quinolin-4-amine was prepared according to the methods described in parts A-E of Example 6 using 4-chloro-3-nitroquinoline in lieu of 7-(benzyloxy)-4-chloro-3-nitroquinoline. The product was provided as 0.16 g of a yellow solid, mp 169-171° C.

Anal. calcd for $C_{18}H_{23}N_5O_2$: C, 63.32; H, 6.79; N, 20.51. Found: C, 63.48; H, 6.62; N, 20.69.

Example 20

2-{[Methoxy(methyl)amino]methyl}-1-(tetrahydro-2H-pyran-4-ylmethyl)-1H-imidazo[4,5-c]quinolin-4-amine

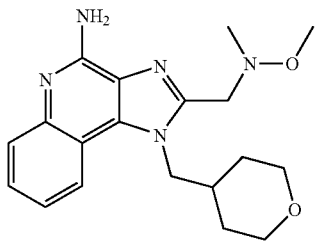

2-(Chloromethyl)-1-(tetrahydro-2H-pyran-4-ylmethyl)-1H-imidazo[4,5-c]quinolin-4-amine (prepared according to the method described in parts A-D of Example 6 using 4-chloro-3-nitroquinoline in lieu of 7-(benzyloxy)-4-chloro-3-nitroquinoline) was converted to 2-{[methoxy(methyl)amino]methyl}-1-(tetrahydro-2H-pyran-4-ylmethyl)-1H-imidazo[4,5-c]quinolin-4-amine using the method detailed in Example 7. The product was provided as 0.16 g of a yellow solid, mp 223-226° C.

Anal. calcd for $C_{19}H_{25}N_5O_2$: C, 64.20; H, 7.09; N, 19.70. Found: C, 64.08; H, 7.06; N, 19.74.

Example 21

1-{4-Amino-7-bromo-2-[(methoxyamino)methyl]-1H-imidazo[4,5-c][1,5]naphthyridin-1-yl}-2-methylpropan-2-ol

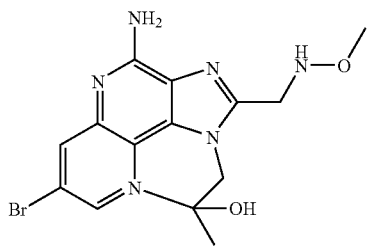

1-{4-Amino-7-bromo-2-[(methoxyamino)methyl]-1H-imidazo[4,5-c][1,5]naphthyridin-1-yl}-2-methylpropan-2-ol was prepared according to the method described in Example 6, parts A-D, using 7-bromo-4-chloro-3-nitro[1,5]naphthyridine and 1-amino-2-methylpropan-2-ol in lieu of 7-(benzyloxy)-4-chloro-3-nitroquinoline and 1-tetrahydro-2H-pyran-4-ylmethanamine, respectively. The product was provided as 0.58 g of a yellow solid, mp 167-168° C.

Anal. calcd for $C_{15}H_{19}BrN_6O_2$: C, 45.58; H, 4.85; N, 21.26. Found: C, 45.81; H, 4.72; N, 21.45.

Example 22

1-{4-Amino-2-[(methoxyamino)methyl]-7-(pyridin-3-yl)-1H-imidazo[4,5-c][1,5]naphthyridin-1-yl}-2-methylpropan-2-ol

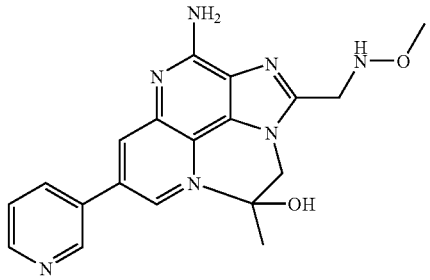

A stream of nitrogen was bubbled through a stirring suspension of 1-{4-amino-7-bromo-2-[(methoxyamino)methyl]-1H-imidazo[4,5-c][1,5]naphthyridin-1-yl}-2-methylpropan-2-ol (0.590 g, 1.49 mmol), 3-pyridineboronic acid (0.220 g, 1.79 mmol), and potassium carbonate (0.681 g, 4.93 mmol) in ethylene glycol dimethyl ether (10 mL) and water (5 mL) in a pressure vessel for 5 minutes. Dichlorobis(triphenylphosphine)palladium(III) (0.031 g, 0.045 mmol) was added and nitrogen was bubbled through for an additional 5 minutes. The pressure vessel was capped and placed in a 110° C. oil bath for 10 minutes. The resulting solution was cooled to ambient temperature and concentrated. The residue was purified by column chromatography using a HORIZON HPFC system (silica cartridge, eluting with 5-25% 1M ammonia/methanol in dichloromethane). The resulting yellow solid was crystallized from acetonitrile and isolated by filtration to yield 167 mg of 1-{4-amino-2-[(methoxyamino)methyl]-7-(pyridin-3-yl)-1H-imidazo[4,5-c][1,5]naphthyridin-1-yl}-2-methylpropan-2-ol as a light yellow solid, mp 195-197° C.

Anal. calcd for $C_{20}H_{23}N_7O_2$: C, 61.05; H, 5.89; N, 24.92. Found: C, 60.71; H, 5.91; N, 24.66.

Example 23

1-(4-Amino-7-bromo-2-{[methoxy(methyl)amino]methyl}-1H-imidazo[4,5-c][1,5]naphthyridin-1-yl)-2-methylpropan-2-ol

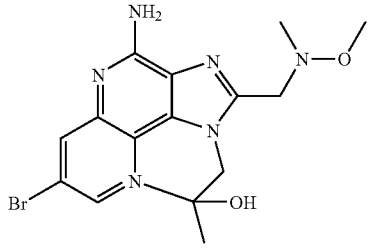

1-(4-Amino-7-bromo-2-{[methoxy(methyl)amino]methyl}-1H-imidazo[4,5-c][1,5]naphthyridin-1-yl)-2-methylpropan-2-ol was prepared according to the methods described in Example 6 parts A-D (using 7-bromo-4-chloro-3-nitro[1,5]naphthyridine and 1-amino-2-methylpropan-2-ol in lieu of 7-(benzyloxy)-4-chloro-3-nitroquinoline and 1-tetrahydro-2H-pyran-4-ylmethanamine, respectively) and Example 7. The product was provided as 0.63 g of a white solid, mp 190-192° C.

Anal. calcd for $C_{16}H_{21}BrN_6O_2$: C, 46.95; H, 5.17; N, 20.53. Found: C, 47.10; H, 4.91; N, 20.70.

Example 24

1-(4-Amino-2-{[methoxy(methyl)amino]methyl}-7-(pyridin-3-yl)-1H-imidazo[4,5-c][1,5]naphthyridin-1-yl)-2-methylpropan-2-ol

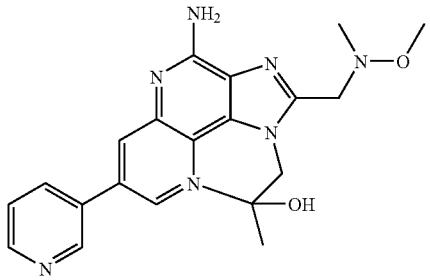

1-(4-Amino-7-bromo-2-{[methoxy(methyl)amino]methyl}-1H-imidazo[4,5-c][1,5]naphthyridin-1-yl)-2-methylpropan-2-ol was converted to 1-(4-amino-2-{[methoxy(methyl)amino]methyl}-7-(pyridin-3-yl)-1H-imidazo[4,5-c][1,5]naphthyridin-1-yl)-2-methylpropan-2-ol according to the method described in Example 22. The product was provided as 0.23 g of a tan solid, mp 187-189° C.

Anal. calcd for $C_{21}H_{25}N_7O_2$: C, 61.90; H, 6.18; N, 24.06. Found: C, 62.02; H, 6.14; N, 24.37.

Exemplary Compounds

Certain exemplary compounds, including some of those described above in the Examples, have the following Formulas (IIa, IIIa, IVa, or Va) and the following $R_1$ and $R_2$ substituents, wherein each line of the table is matched with Formula Ia, IIIa, IVa, or Va to represent a specific embodiment of the invention.

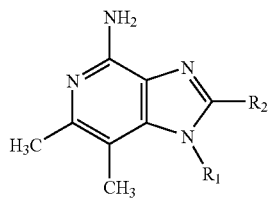

IIa

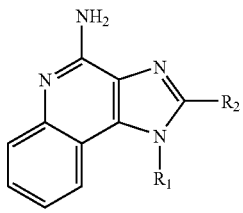

IIIa

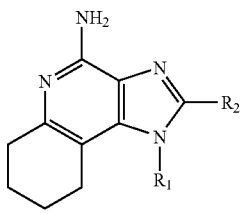

IVa

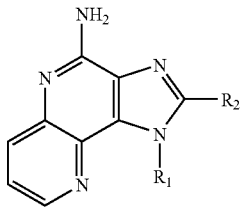

Va

| $R_1$ | $R_2$ |
|---|---|
| 2-methylpropyl | —CH=N—OH |
| 2-hydroxy-2-methylpropyl | —CH=N—OH |

-continued

| | |
|---|---|
| 2-methyl-2-[(methylsulfonyl)amino]propyl | —CH=N—OH |
| 4-[(methylsulfonyl)amino]butyl | —CH=N—OH |
| 2-methylpropyl | —CH=N—OCH₃ |
| 2-hydroxy-2-methylpropyl | —CH=N—OCH₃ |
| 2-methyl-2-[(methylsulfonyl)amino]propyl | —CH=N—OCH₃ |
| 4-[(methylsulfonyl)amino]butyl | —CH=N—OCH₃ |
| 2-methylpropyl | —CH₂—NH—OH |
| 2-hydroxy-2-methylpropyl | —CH₂—NH—OH |
| 2-methyl-2-[(methylsulfonyl)amino]propyl | —CH₂—NH—OH |
| 4-[(methylsulfonyl)amino]butyl | —CH₂—NH—OH |
| 2-methylpropyl | —CH₂—N(CH₃)—OH |
| 2-hydroxy-2-methylpropyl | —CH₂—N(CH₃)—OH |
| 2-methyl-2-[(methylsulfonyl)amino]propyl | —CH₂—N(CH₃)—OH |
| 4-[(methylsulfonyl)amino]butyl | —CH₂—N(CH₃)—OH |
| 2-methylpropyl | —CH₂—NH—OCH₃ |
| 2-hydroxy-2-methylpropyl | —CH₂—NH—OCH₃ |
| 2-methyl-2-[(methylsulfonyl)amino]propyl | —CH₂—NH—OCH₃ |
| 4-[(methylsulfonyl)amino]butyl | —CH₂—NH—OCH₃ |
| 2-methylpropyl | —CH₂—N(CH₃)—OCH₃ |
| 2-hydroxy-2-methylpropyl | —CH₂—N(CH₃)—OCH₃ |
| 2-methyl-2-[(methylsulfonyl)amino]propyl | —CH₂—N(CH₃)—OCH₃ |
| 4-[(methylsulfonyl)amino]butyl | —CH₂—N(CH₃)—OCH₃ |
| 2-methylpropyl | —CH₂—N(—C(O)—CH₃)—OH |
| 2-hydroxy-2-methylpropyl | —CH₂—N(—C(O)—CH₃)—OH |
| 2-methyl-2-[(methylsulfonyl)amino]propyl | —CH₂—N(—C(O)—CH₃)—OH |
| 4-[(methylsulfonyl)amino]butyl | —CH₂—N(—C(O)—CH₃)—OH |
| 2-methylpropyl | —CH₂—N(—C(O)—CH₃)—OCH₃ |
| 2-hydroxy-2-methylpropyl | —CH₂—N(—C(O)—CH₃)—OCH₃ |
| 2-methyl-2-[(methylsulfonyl)amino]propyl | —CH₂—N(—C(O)—CH₃)—OCH₃ |
| 4-[(methylsulfonyl)amino]butyl | —CH₂—N(—C(O)—CH₃)—OCH₃ |
| 2-methylpropyl | —CH₂—N(—S(O)₂—CH₃)—OH |
| 2-hydroxy-2-methylpropyl | —CH₂—N(—S(O)₂—CH₃)—OH |
| 2-methyl-2-[(methylsulfonyl)amino]propyl | —CH₂—N(—S(O)₂—CH₃)—OH |
| 4-[(methylsulfonyl)amino]butyl | —CH₂—N(—S(O)₂—CH₃)—OH |
| 2-methylpropyl | —CH₂—N(—S(O)₂—CH₃)—OCH₃ |
| 2-hydroxy-2-methylpropyl | —CH₂—N(—S(O)₂—CH₃)—OCH₃ |
| 2-methyl-2-[(methylsulfonyl)amino]propyl | —CH₂—N(—S(O)₂—CH₃)—OCH₃ |
| 4-[(methylsulfonyl)amino]butyl | —CH₂—N(—S(O)₂—CH₃)—OCH₃ |
| 2-methylpropyl | —CH₂—N(—C(O)—NH—CH₃)—OH |
| 2-hydroxy-2-methylpropyl | —CH₂—N(—C(O)—NH—CH₃)—OH |
| 2-methyl-2-[(methylsulfonyl)amino]propyl | —CH₂—N(—C(O)—NH—CH₃)—OH |
| 4-[(methylsulfonyl)amino]butyl | —CH₂—N(—C(O)—NH—CH₃)—OH |
| 2-methylpropyl | —CH₂—N(—C(O)—NH—CH₃)—OCH₃ |
| 2-hydroxy-2-methylpropyl | —CH₂—N(—C(O)—NH—CH₃)—OCH₃ |
| 2-methyl-2-[(methylsulfonyl)amino]propyl | —CH₂—N(—C(O)—NH—CH₃)—OCH₃ |
| 4-[(methylsulfonyl)amino]butyl | —CH₂—N(—C(O)—NH—CH₃)—OCH₃ |

Certain exemplary compounds, including some of those described above in the Examples, have the following Formulas (IIa, IIIa, IVa, or Va) and the following $R_1$ and $R_2$ substituents, wherein each line of the table is matched with Formula IIa, IIIa, IVa, or Va to represent a specific embodiment of the invention.

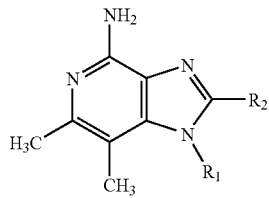

IIa

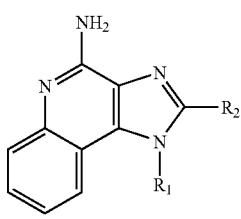

IIIa

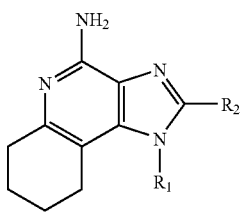

IVa

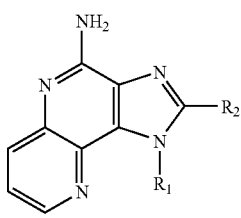

Va

| $R_1$ | $R_2$ |
|---|---|
| (1-hydroxycyclobuyty)methyl | —CH=N—OH |
| (1-hydroxycyclopentyl)methyl | —CH=N—OH |
| (1-hydroxycyclohexyl)methyl | —CH=N—OH |
| tetrahydro-2H-pyran-4-ylmethyl | —CH=N—OH |
| (1-hydroxycyclobutyl)methyl | —CH=N—OCH$_3$ |
| (1-hydroxycyclopentyl)methyl | —CH=N—OCH$_3$ |
| (1-hydroxycyclohexyl)methyl | —CH=N—OCH$_3$ |
| tetrahydro-2H-pyran-4-ylmethyl | —CH=N—OCH$_3$ |
| (1-hydroxycyclobutyl)methyl | —CH$_2$—NH—OH |
| (1-hydroxycyclopentyl)methyl | —CH$_2$—NH—OH |
| (1-hydroxycyclohexyl)methyl | —CH$_2$—NH—OH |
| tetrahydro-2H-pyran-4-ylmethyl | —CH$_2$—NH—OH |
| (1-hydroxycyclobutyl)methyl | —CH$_2$—N(CH$_3$)—OH |
| (1-hydroxycyclopentyl)methyl | —CH$_2$—N(CH$_3$)—OH |
| (1-hydroxycyclohexyl)methyl | —CH$_2$—N(CH$_3$)—OH |
| tetrahydro-2H-pyran-4-ylmethyl | —CH$_2$—N(CH$_3$)—OH |
| (1-hydroxycyclobutyl)methyl | —CH$_2$—NH—OCH$_3$ |
| (1-hydroxycyclopentyl)methyl | —CH$_2$—NH—OCH$_3$ |
| (1-hydroxycyclohexyl)methyl | —CH$_2$—NH—OCH$_3$ |
| tetrahydro-2H-pyran-4-ylmethyl | —CH$_2$—NH—OCH$_3$ |
| (1-hydroxycyclobutyl)methyl | —CH$_2$—N(CH$_3$)—OCH$_3$ |
| (1-hydroxycyclopentyl)methyl | —CH$_2$—N(CH$_3$)—OCH$_3$ |
| (1-hydroxycyclohexyl)methyl | —CH$_2$—N(CH$_3$)—OCH$_3$ |
| tetrahydro-2H-pyran-4-ylmethyl | —CH$_2$—N(CH$_3$)—OCH$_3$ |
| (1-hydroxycyclobutyl)methyl | —CH$_2$—N(—C(O)—CH$_3$)—OH |
| (1-hydroxycyclopentyl)methyl | —CH$_2$—N(—C(O)—CH$_3$)—OH |
| (1-hydroxycyclohexyl)methyl | —CH$_2$—N(—C(O)—CH$_3$)—OH |

| | -continued |
|---|---|
| tetrahydro-2H-pyran-4-ylmethyl | —CH₂—N(—C(O)—CH₃)—OH |
| (1-hydroxycyclobutyl)methyl | —CH₂—N(—C(O)—CH₃)—OCH₃ |
| (1-hydroxycyclopentyl)methyl | —CH₂—N(—C(O)—CH₃)—OCH₃ |
| (1-hydroxycyclohexyl)methyl | —CH₂—N(—C(O)—CH₃)—OCH₃ |
| tetrahydro-2H-pyran-4-ylmethyl | —CH₂—N(—C(O)—CH₃)—OCH₃ |
| (1-hydroxycyclobutyl)methyl | —CH₂—N(—S(O)₂—CH₃)—OH |
| (1-hydroxycyclopentyl)methyl | —CH₂—N(—S(O)₂—CH₃)—OH |
| (1-hydroxycyclohexyl)methyl | —CH₂—N(—S(O)₂—CH₃)—OH |
| tetrahydro-2H-pyran-4-ylmethyl | —CH₂—N(—S(O)₂—CH₃)—OH |
| (1-hydroxycyclobutyl)methyl | —CH₂—N(—S(O)₂—CH₃)—OCH₃ |
| (1-hydroxycyclopentyl)methyl | —CH₂—N(—S(O)₂—CH₃)—OCH₃ |
| (1-hydroxycyclohexyl)methyl | —CH₂—N(—S(O)₂—CH₃)—OCH₃ |
| tetrahydro-2H-pyran-4-ylmethyl | —CH₂—N(—S(O)₂—CH₃)—OCH₃ |
| (1-hydroxycyclobuytyl)methyl | —CH₂—N(—C(O)—NH—CH₃)—OH |
| (1-hydroxycyclopentyl)methyl | —CH₂—N(—C(O)—NH—CH₃)—OH |
| (1-hydroxycyclohexyl)methyl | —CH₂—N(—C(O)—NH—CH₃)—OH |
| tetrahydro-2H-pyran-4-ylmethyl | —CH₂—N(—C(O)—NH—CH₃)—OH |
| (1-hydroxycyclobutyl)methyl | —CH₂—N(—C(O)—NH—CH₃)—OCH₃ |
| (1-hydroxycyclopentyl)methyl | —CH₂—N(—C(O)—NH—CH₃)—OCH₃ |
| (1-hydroxycyclohexyl)methyl | —CH₂—N(—C(O)—NH—CH₃)—OCH₃ |
| tetrahydro-2H-pyran-4-ylmethyl | —CH₂—N(—C(O)—NH—CH₃)—OCH₃ |

Certain exemplary compounds, including some of those described above in the Examples, have the following Formulas (IIId, or Vd) and the following $R_1$ and $R_2$ substituents, wherein each line of the table is matched with Formula IIId or Vd to represent a specific embodiment of the invention.

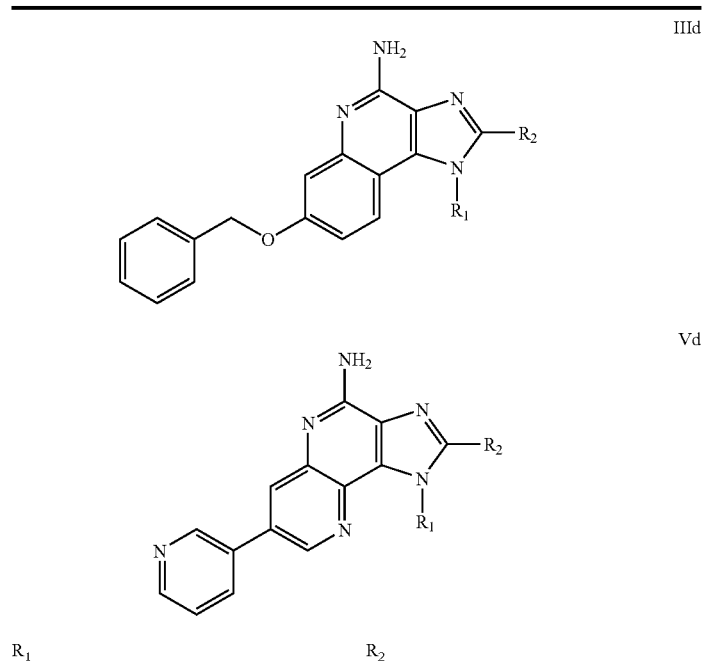

| $R_1$ | $R_2$ |
|---|---|
| 2-methylpropyl | —CH=N—OH |
| 2-hydroxy-2-methylpropyl | —CH=N—OH |
| 2-methyl-2-[(methylsulfonyl)amino]propyl | —CH=N—OH |
| 4-[(methylsulfonyl)amino]butyl | —CH=N—OH |
| (1-hydroxycyclobutyl)methyl | —CH=N—OH |
| (1-hydroxycyclopentyl)methyl | —CH=N—OH |
| (1-hydroxycyclohexyl)methyl | —CH=N—OH |
| tetrahydro-2H-pyran-4-ylmethyl | —CH=N—OH |
| 2-methylpropyl | —CH=N—OCH₃ |
| 2-hydroxy-2-methylpropyl | —CH=N—OCH₃ |
| 2-methyl-2-[(methylsulfonyl)amino]propyl | —CH=N—OCH₃ |
| 4-[(methylsulfonyl)amino]butyl | —CH=N—OCH₃ |
| (1-hydroxycyolobutyl)methyl | —CH=N—OCH₃ |
| (1-hydroxycyclopentyl)methyl | —CH=N—OCH₃ |
| (1-hydroxycyclohexyl)methyl | —CH=N—OCH₃ |

-continued

| | |
|---|---|
| tetrahydro-2H-pyran-4-ylmethyl | —CH=N—OCH₃ |
| 2-methylpropyl | —CH₂—NH—OH |
| 2-hydroxy-2-methylpropyl | —CH₂—NH—OH |
| 2-methyl-2-[(methylsulfonyl)amino]propyl | —CH₂—NH—OH |
| 4-[(methylsulfonyl)amino]butyl | —CH₂—NH—OH |
| (1-hydroxycyclobutyl)methyl | —CH₂—NH—OH |
| (1-hydroxycyclopentyl)methyl | —CH₂—NH—OH |
| (1-hydroxycyclohexyl)methyl | —CH₂—NH—OH |
| tetrahydro-2H-pyran-4-ylmethyl | —CH₂—NH—OH |
| 2-methylpropyl | —CH₂—N(CH₃)—OH |
| 2-hydroxy-2-methylpropyl | —CH₂—N(CH₃)—OH |
| 2-methyl-2-[(methylsulfonyl)amino]propyl | —CH₂—N(CH₃)—OH |
| 4-[(methylsulfonyl)amino]butyl | —CH₂—N(CH₃)—OH |
| (1-hydroxycyclobutyl)methyl | —CH₂—N(CH₃)—OH |
| (1-hydroxycyclopentyl)methyl | —CH₂—N(CH₃)—OH |
| (1-hydroxycyclohexyl)methyl | —CH₂—N(CH₃)—OH |
| tetrahydro-2H-pyran-4-ylmethyl | —CH₂—N(CH₃)—OH |
| 2-methylpropyl | —CH₂—NH—OCH₃ |
| 2-hydroxy-2-methylpropyl | —CH₂—NH—OCH₃ |
| 2-methyl-2-[(methylsulfonyl)amino]propyl | —CH₂—NH—OCH₃ |
| 4-[(methylsulfonyl)amino]butyl | —CH₂—NH—OCH₃ |
| (1-hydroxycyclobutyl)methyl | —CH₂—NH—OCH₃ |
| (1-hydroxycyclopentyl)methyl | —CH₂—NH—OCH₃ |
| (1-hydroxycyclohexyl)methyl | —CH₂—NH—OCH₃ |
| tetrahydro-2H-pyran-4-ylmethyl | —CH₂—NH—OCH₃ |
| 2-methylpropyl | —CH₂—N(CH₃)—OCH₃ |
| 2-hydroxy-2-methylpropyl | —CH₂—N(CH₃)—OCH₃ |
| 2-methyl-2-[(methylsulfonyl)amino]propyl | —CH₂—N(CH₃)—OCH₃ |
| 4-[(methylsulfonyl)amino]butyl | —CH₂—N(CH₃)—OCH₃ |
| (1-hydroxycyclobutyl)methyl | —CH₂—N(CH₃)—OCH₃ |
| (1-hydroxycyclopentyl)methyl | —CH₂—N(CH₃)—OCH₃ |
| (1-hydroxycyclohexyl)methyl | —CH₂—N(CH₃)—OCH₃ |
| tetrahydro-2H-pyran-4-ylmethyl | —CH₂—N(CH₃)—OCH₃ |
| 2-methylpropyl | —CH₂—N(—C(O)—CH₃)—OH |
| 2-hydroxy-2-methylpropyl | —CH₂—N(—C(O)—CH₃)—OH |
| 2-methyl-2-[(methylsulfonyl)amino]propyl | —CH₂—N(—C(O)—CH₃)—OH |
| 4-[(methylsulfonyl)amino]butyl | —CH₂—N(—C(O)—CH₃)—OH |
| (1-hydroxycyclobutyl)methyl | —CH₂—N(—C(O)—CH₃)—OH |
| (1-hydroxycyclopentyl)methyl | —CH₂—N(—C(O)—CH₃)—OH |
| (1-hydroxycyclohexyl)methyl | —CH₂—N(—C(O)—CH₃)—OH |
| tehydro-2H-pyran-4-ylmethyl | —CH₂—N(—C(O)—CH₃)—OH |
| 2-methylpropyl | —CH₂—N(—C(O)—CH₃)—OCH₃ |
| 2-hydroxy-2-methylpropyl | —CH₂—N(—C(O)—CH₃)—OCH₃ |
| 2-methyl-2-[(methylsulfonyl)amino]propyl | —CH₂—N(—C(O)—CH₃)—OCH₃ |
| 4-[(methylsulfonyl)amino]butyl | —CH₂—N(—C(O)—CH₃)—OCH₃ |
| (1-hydroxycyclobutyl)methyl | —CH₂—N(—C(O)—CH₃)—OCH₃ |
| (1-hydoxycyclopentyl)methyl | —CH₂—N(—C(O)—CH₃)—OCH₃ |
| (1-hydroxycyclohexyl)methyl | —CH₂—N(—C(O)—CH₃)—OCH₃ |
| tetrahydro-2H-pyran-4-ylmethyl | —CH₂—N(—C(O)—CH₃)—OCH₃ |
| 2-methylpropyl | —CH₂—N(—S(O)₂—CH₃)—OH |
| 2-hydroxy-2-methylpropyl | —CH₂—N(—S(O)₂—CH₃)—OH |
| 2-methyl-2-[(methylsulfonyl)amino]propyl | —CH₂—N(—S(O)₂—CH₃)—OH |
| 4-[(methylsulfonyl)amino]butyl | —CH₂—N(—S(O)₂—CH₃)—OH |
| (1-hydroxycyclobutyl)methyl | —CH₂—N(—S(O)₂—CH₃)—OH |
| (1-hydroxycyclopentyl)methyl | —CH₂—N(—S(O)₂—CH₃)—OH |
| (1-hydroxycyclohexyl)methyl | —CH₂—N(—S(O)₂—CH₃)—OH |
| tetrahydro-2H-pyran-4-ylmethyl | —CH₂—N(—S(O)₂—CH₃)—OH |
| 2-methylpropyl | —CH₂—N(—S(O)₂—CH₃)—OCH₃ |
| 2-hydroxy-2-methylpropyl | —CH₂—N(—S(O)₂—CH₃)—OCH₃ |
| 2-methyl-2-[(methylsulfonyl)amino]propyl | —CH₂—N(—S(O)₂—CH₃)—OCH₃ |
| 4-[(methylsulfonyl)amino]butyl | —CH₂—N(—S(O)₂—CH₃)—OCH₃ |
| (1-hyclroxycyclobutyl)methyl | —CH₂—N(—S(O)₂—CH₃)—OCH₃ |
| (1-hydroxycyclopentyl)methyl | —CH₂—N(—S(O)₂—CH₃)—OCH₃ |
| (1-hydroxycyclohexyl)methyl | —CH₂—N(—S(O)₂—CH₃)—OCH₃ |
| tetrahydro-2H-pyran-4-ylmethyl | —CH₂—N(—S(O)₂—CH₃)—OCH₃ |
| 2-methylpropyl | —CH₂—N(—C(O)—NH—CH₃)—OH |
| 2-hydroxy-2-methylpropyl | —CH₂—N(—C(O)—NH—CH₃)—OH |
| 2-methyl-2-[(methylsulfonyl)amino]propyl | —CH₂—N(—C(O)—NH—CH₃)—OH |
| 4-[(methylsulfonyl)amino]butyl | —CH₂—N(—C(O)—NH—CH₃)—OH |
| (1-hydroxycyclobutyl)methyl | —CH₂—N(—C(O)—NH—CH₃)—OH |
| (1-hydroxycyclopentyl)methyl | —CH₂—N(—C(O)—NH—CH₃)—OH |
| (1-hydroxycyclohexyl)methyl | —CH₂—N(—C(O)—NH—CH₃)—OH |
| tetrahydro-2H-pyran-4-ylmethyl | —CH₂—N(—C(O)—NH—CH₃)—OH |
| 2-methylpropyl | —CH₂—N(—C(O)—NH—CH₃)—OCH₃ |
| 2-hydroxy-2-methylpropyl | —CH₂—N(—C(O)—NH—CH₃)—OCH₃ |
| 2-methyl-2-[(methylsulfonyl)amino]propyl | —CH₂—N(—C(O)—NH—CH₃)—OCH₃ |
| 4-[(methylsulfonyl)amino]butyl | —CH₂—N(—C(O)—NH—CH₃)—OCH₃ |
| (1-hydroxycyclobutyl)methyl | —CH₂—N(—C(O)—NH—CH₃)—OCH₃ |

-continued

| | |
|---|---|
| (1-hydroxycyclopentyl)methyl | —CH$_2$—N(—C(O)—NH—CH$_3$)—OCH$_3$ |
| (1-hydroxycyclohexyl)methyl | —CH$_2$—N(—C(O)—NH—CH$_3$)—OCH$_3$ |
| tetrahydro-2H-pyran-4-ylmethyl | —CH$_2$—N(—C(O)—NH—CH$_3$)—OCH$_3$ |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10$^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is 2×10$^6$ cells/mL. The plates are covered with sterile plastic lids, mixed gently and then incubated for 18 hours to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30° C. to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AEC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10⁶ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30 µM-0.014 µM) and the DMSO concentration to 0.4%. The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30° C. to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α a capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above-mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (1 molar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I:

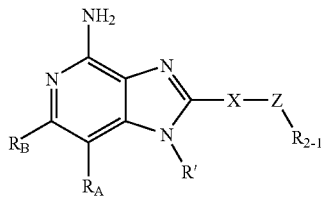

wherein:
Z is selected from the group consisting of:
—C(=N—O—$R_{2-2}$)— and
—C($R_{2-4}$)(—N(—O$R_{2-2}$)—Y—$R_{2-3}$)—;
X is selected from the group consisting of a bond, $C_{1-4}$ alkylene and $C_{2-4}$ alkenylene;
$R_{2-1}$, $R_{2-2}$, and $R_{2-3}$ are independently selected from the group consisting of:
hydrogen,
alkyl,
alkenyl,
aryl,
arylalkylenyl,
heteroaryl,
heteroarylalkylenyl,
heterocyclyl, and
heterocyclylalkylenyl, and
alkyl, alkenyl, aryl, arylalkylenyl, heteroaryl, hetoroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$$R_{2-5}$,
—NH—S(O)$_2$—$R_{2-5}$,
haloalkoxy,
halogen,
cyano,
nitro,
—$N_3$,
aryl,
heteroaryl,
heterocyclyl,
aryloxy,
arylalkyleneoxy,
—C(O)—O-alkyl,
—C(O)—N($R_8$)$_2$,
—N($R_8$)—C(O)—$R_{2-5}$,
—NH—C(O)—NH—$R_{2-5}$,
—NH—C(O)—NH$_2$,
—O—(CO)-alkyl, and
—C(O)-alkyl;
with the proviso that $R_{2-2}$ is other than alkenyl wherein the carbon atom bonded to —O— is doubly bonded to another carbon atom;
$R_{2-4}$ is selected from the group consisting of hydrogen, $C_{1-4}$alkyl, and phenyl;
$R_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —$N_3$;
Y is selected from the group consisting of:
a bond,
—C($R_6$)—,
—S(O)$_2$—,
—S(O)$_2$—N($R_8$)—,

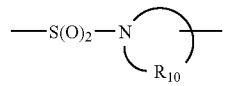

—C(O)—O—,
—C($R_6$)—N($R_8$)—,
—C(O)—N($R_8$)—S(O)$_2$—,
—C($R_6$)—N($R_8$)—C(O)—,

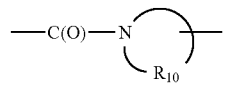

—C(O)—C(O)—,
—C(O)—C(O)—O—, and
—C(=NH)—N($R_8$)—;
$R_A$ and $R_B$ taken together form a fused benzene ring unsubstituted or substituted by one or more R''' groups, wherein the one or more R''' groups are one $R_3$— group, or one $R_3$ group and one R group, or one, two, three, or four R groups;
$R_3$ is selected from the group consisting of:
—Z'—$R_4$,
—Z'—X'—$R_4$,
—Z'—X'—Y'—$R_4$,
—Z'—X'—Y'—X'—Y'—$R_4$, and
—Z'—X'—$R_5$;
X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;
Y' is selected from the group consisting of:
—O—
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

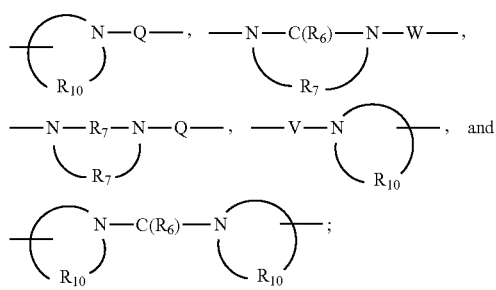

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

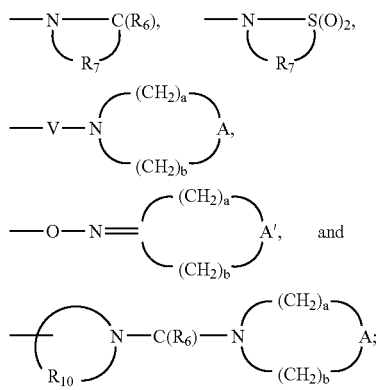

R is selected from the group consisting of:
halogen,
hydroxy,
alkyl,
alkenyl,
haloalkyl,
alkoxy,
alkylthio, and
—N($R_9$)$_2$;

R' is $R_1$; wherein $R_1$ is selected from the group consisting of:
—$R_4$',
—X"—$R_4$',
—X"—Y"—$R_4$',
—X"—Y"—X"—Y"—$R_4$', and
—X"—$R_5$';

wherein:
X" is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y" is selected from the group consisting of:
—O—,
—S(O)$_{0-2}$,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)—O—,
—O—N=C($R_4$)—,
—C(=N—O—$R_8$)—,
—CH(—N(—O—$R_8$)-Q-$R_4$)—,

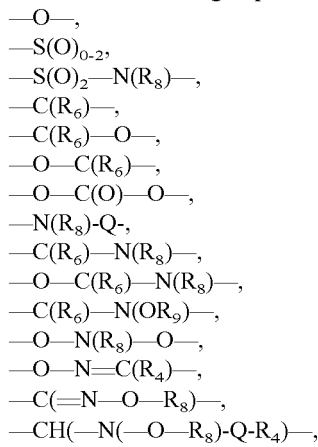

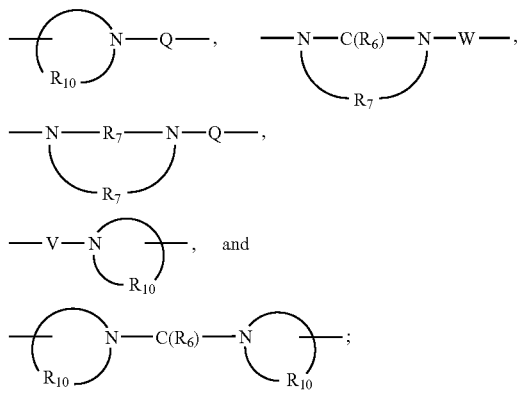

$R_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$' is selected from the group consisting of:

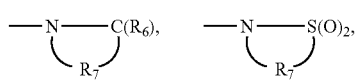

-continued

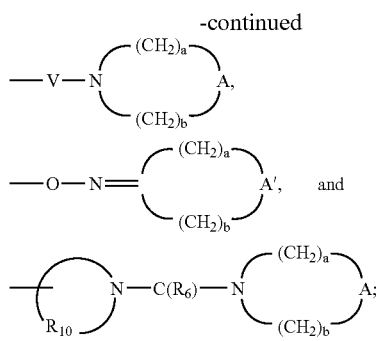

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, hydroxy-C$_{1-10}$ alkylenyl, heteroaryl-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(—O—R$_4$)—,
A' is selected from the group consisting of —O—, —S(O)$_{0-2}$—, N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

2. The compound of claim 1, wherein Formula I is Formula III:

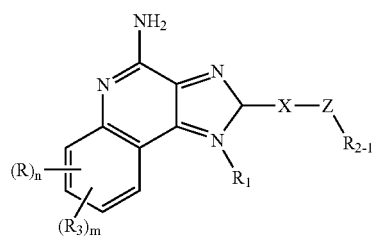

wherein:
Z is selected from the group consisting of:
—C(=N—O—R$_{2-2}$)— and
—C(R$_{2-4}$)(—N(—OR$_{2-2}$)—Y—R$_{2-3}$)—;
X is selected from the group consisting of a bond, C$_{1-4}$ alkylene and C$_{2-4}$ alkenylene;
R$_{2-1}$, R$_{2-2}$, and R$_{2-3}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, and heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$R$_{2-5}$,
—NH—S(O)$_2$—R$_{2-5}$,
haloalkoxy,
halogen,
cyano,
nitro,
—N$_3$,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)—R$_{2-5}$,
—NH—C(O)—NH—R$_{2-5}$,
—NH—C(O)—NH$_2$,
—O—(CO)-alkyl, and
—C(O)-alkyl;
with the proviso that R$_{2-2}$ is other than alkenyl wherein the carbon atom bonded to —O— is doubly bonded to another carbon atom;
R$_{2-4}$ is selected from the group consisting of hydrogen, C$_{1-4}$alkyl, and phenyl;
R$_{2-5}$ is selected from the group consisting of alkyl, aryl, arylalkylenyl, heteroaryl, and heteroarylalkylenyl, each of which is unsubstituted or substituted by one or more substituents selected from the group consisting of halogen, cyano, nitro, alkoxy, dialkylamino, alkylthio, haloalkyl, haloalkoxy, alkyl, and —N$_3$;
Y is selected from the group consisting of:
a bond,
—C(R$_6$)—,
—S(O)$_2$—,
—S(O)$_2$—N(R$_8$)—,

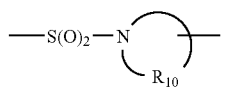

—C(O)—O—,
—C(R$_6$)—N(R$_8$)—,
—C(O)—N(R$_8$)—S(O)$_2$—,
—C(R$_6$)—N(R$_8$)—C(O)—,

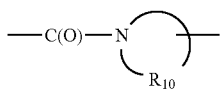

—C(O)—C(O)—,
—C(O)—C(O)—O—, and
—C(=NH)—N(R$_8$)—,

R is selected from the group consisting of:
  halogen,
  hydroxy,
  alkyl,
  alkenyl,
  haloalkyl,
  alkoxy,
  alkylthio, and
  —N(R$_9$)$_2$;

n is an integer from 0 to 4;

R$_1$ is selected from the group consisting of:
  —R$_4$',
  —X"—R$_4$',
  —X"—Y"—R$_4$',
  —X"—Y"—X"—Y"—R$_4$' and
  —X"—R$_5$';

wherein:
  X" is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y" is selected from the group consisting of:
    —O—,
    —S(O)$_{0-2}$—,
    —S(O)$_2$—N(R$_8$)—,
    —C(R$_6$)—,
    —C(R$_6$)—O—,
    —O—C(R$_6$)—,
    —O—C(O)—O—,
    —N(R$_8$)-Q-,
    —C(R$_6$)—N(R$_8$)—,
    —O—C(R$_6$)—N(R$_8$)—,
    —C(R$_6$)—N(OR$_9$)—,
    —O—N(R$_8$)-Q-,
    —O—N=C(R$_4$)—,
    —C(=N—O—R$_8$)—,
    —CH(—N(—O—R$_8$)-Q-R$_4$)—,

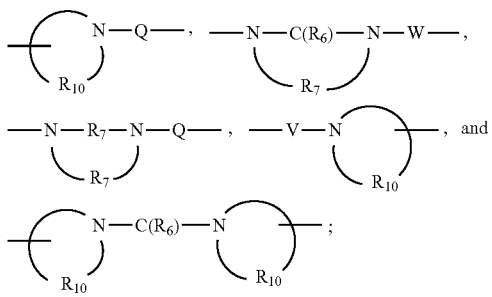

R$_4$' is selected from the group consisting or hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, alkylamino, dialkylamino, (dialkylamino)alkyleneoxy, and in the case of alkyl, alkenyl, alkynyl, and heterocyclyl, oxo;

R$_5$' is selected from the group consisting of:

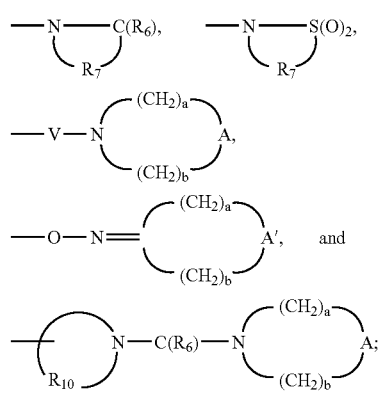

R$_3$ is selected from the group consisting of:
  —Z'—R$_4$,
  —Z'—X'—R$_4$,
  —Z'—X'—Y'—X'—Y'—R$_4$, and
  —Z'—X'—R$_5$;

m is 0 or 1, with the proviso that when m is 1 than n is 0 or 1;

X' is selected from the group consisting of alkylene, alkenylene, alkynylene, arylene, heteroarylene, and heterocyclylene, wherein the alkylene, alkenylene, and alkynylene groups can be optionally interrupted or terminated by arylene, heteroarylene or heterocyclylene and optionally interrupted by one or more —O— groups;

Y' is selected from the group consisting of:
  —O—,
  —S(O)$_{0-2}$—,
  —S(O)$_2$—N(R$_8$)—,
  —C(R$_6$)—,
  —C(R$_6$)—O—,
  —O—C(R$_6$)—
  —O—C(O)—O—,
  —N(R$_8$)-Q-,
  —C(R$_6$)—N(R$_8$)—,
  —O—C(R$_6$)—N(R$_8$)—,
  —C(R$_6$)—N(OR$_9$)—,
  —O—N(R$_8$)-Q-,
  —O—N=C(R$_4$)—,
  —C(=N—O—R$_8$)—,
  —CH(—N(—O—R$_8$)-Q-R$_4$)—,

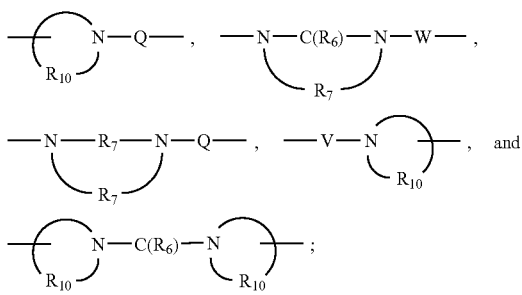

Z' is a bond or —O—;

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

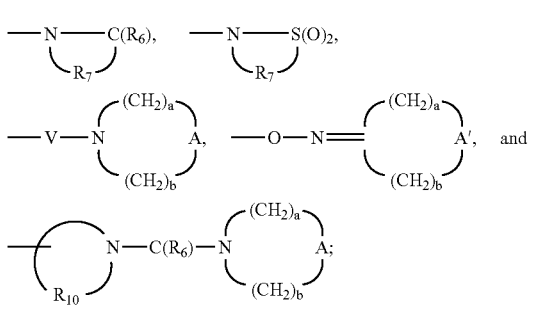

R₆ is selected from the group consisting of =O and =S;
R₇ is C₂₋₇ alkylene;
R₈ is selected from the group consisting of hydrogen, C₁₋₁₀ alkyl, C₂₋₁₀ alkenyl, C₁₋₁₀ alkoxy-C₁₋₁₀ alkylenyl, hydroxy-C₁₋₁₀ alkylenyl, heteroaryl-C₁₋₁₀ alkylenyl, and aryl-C₁₋₁₀ alkylenyl;
R₉ is selected from the group consisting of hydrogen and alkyl;
R₁₀ is C₃₋₈ alkylene;
A is selected from the group consisting of —O—, —C(O)—, —S(O)₀₋₂—, —CH₂—, and —N(-Q-R₄)—,
A' is selected from the group consisting of —O—, —S(O)₀₋₂—, —N(-Q-R₄)—, and —CH₂—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, —C(R₆)—S—, and —C(R₆)—N (OR₉)—;
V is selected from the group consisting of —C(R₆)—, —O—C(R₆)—, N(R₈)—C(R₆)—, and —S(O)₂—;

W is selected from the group consisting of a bond, —C(O)—, and —S(O)₂—; and
a and b are independently integers from 1 to 6 with the proviso that a+b is ≦7; or a pharmaceutically acceptable salt thereof.

3. The compound or salt of claim 2 wherein R is halogen or hydroxy.

4. The compound or salt of claim 2, wherein n is 0.

5. The compound or salt of claim 1 or 2, wherein R₃ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(N,N-dimethylaminocarbonyl)phenyl.

6. The compound or salt of claim 1 or 2, wherein R₃ is benzyloxy.

7. The compound or salt of claim 2, wherein m is 0.

8. The compound or salt of claim 1 or 2 wherein Z is —C(=N—O—R₂₋₂)—.

9. The compound or salt of claim 1 or 2 wherein X is a bond or C₁₋₄alkylene.

10. The compound or salt of claim 1 or 2 wherein:
R₁ is selected from the group consisting of alkyl, arylalkylenyl, aryloxyalkylenyl, hydroxyalkyl, dihydroxyalkyl, alkylsulfonylalkylenyl, X"—Y"—R₄', —X"—R₅', and heterocyclylalkylenyl; wherein the heterocyclyl of the heterocyclylalkylenyl group is optionally substituted by one or more alkyl groups; and wherein:
X" is alkylene;
Y" is —N(R₈)—C(O)—, —N(R₈)—S(O)₂—, —N(R₈)—C(O)—N(R₈)—, or

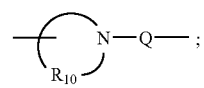

R₄' is alkyl, aryl, or heteroaryl; and
R₅ is

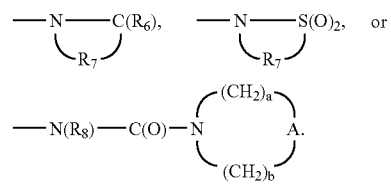

11. The compound or salt of claim 10 wherein R₁ is selected from the group consisting of 2-hydroxy-2-methylpropyl, 2-methylpropyl, propyl, ethyl, methyl, 2,3-dihydroxypropyl, 2-phenoxyethyl, 4-[(methylsulfonyl)amino]butyl, 2-methyl-2-[(methylsulfonyl)amino]propyl, 2-(acetylamino)-2-methylpropyl, 2-{[(isopropylamino)carbonyl]amino}-2-methylpropyl, 4-{[(isopropylamino)carbonyl]amino}butyl, 4-I1,1-dioxidoisothiazolidin-2-yl)butyl, tetrahydro-2H-pyran-4-ylmethyl, and (2,2-dimethyl-1,3-dioxolan-4-yl)methyl.

12. The compound or salt of claim 10 wherein R₁ is selected from the group consisting of (1-hydroxycyclobutyl)methyl, (1-hydroxycyclopentyl)methyl, and (1-hydroxycyclohexyl)methyl.

13. A pharmaceutical composition comprising a therapeutically effective amount of a compound or salt of claim 1 or 2 and a pharmaceutically acceptable carrier.

14. The compound or salt of claim 1 or 2, wherein Z is —C($R_{2-4}$)(—N(O$R_{2-2}$)—Y—$R_{2-3}$)—.

15. The compound or salt of claim 14, wherein $R_{2-4}$ is hydrogen.

16. The compound or salt of claim 14, wherein Y is a bond.

17. The compound or salt of claim 14, wherein $R_{2-3}$ is selected from the group consisting of hydrogen and alkyl.

18. The compound or salt of claim 14, wherein Y is selected from the group consisting of —C(O)—, —S(O)$_2$—, —C(O)—NH—, and $R_{2-3}$ is alkyl.

19. The compound or salt of claim 8, wherein $R_{2-2}$ is selected from the group consisting of hydrogen, alkyl, arylalkylenyl, and heteroarylalkylenyl.

20. The compound or salt of claim 19, wherein $R_{2-2}$ is hydrogen, $C_{1-4}$alkyl, benzyl, or pyridin-2-ylmethyl.

21. The compound or salt of claim 1 or 2, wherein $R_{2-1}$ is selected from the group consisting of hydrogen, alkyl, and aryl.

22. The compound or salt of claim 21, wherein $R_{2-1}$ is hydrogen, $C_{1-4}$alkyl, or phenyl.

23. The compound or salt of claim 9, wherein X is a bond, methylene, or ethylene.

* * * * *